(12) United States Patent
Wang et al.

(10) Patent No.: US 10,365,434 B2
(45) Date of Patent: Jul. 30, 2019

(54) INTEGRATED TARGET WAVEGUIDE DEVICES AND SYSTEMS FOR OPTICAL COUPLING

(71) Applicant: Pacific Biosciences of California, Inc., Menlo Park, CA (US)

(72) Inventors: Shang Wang, San Carlos, CA (US); Mathieu Foquet, Newark, CA (US); Paul Lundquist, San Francisco, CA (US); Aaron Rulison, Los Altos, CA (US); Mark McDonald, Milpitas, CA (US); Ariel Herrmann, San Francisco, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

(21) Appl. No.: 15/180,016

(22) Filed: Jun. 11, 2016

(65) Prior Publication Data

US 2016/0363728 A1    Dec. 15, 2016

Related U.S. Application Data

(60) Provisional application No. 62/175,139, filed on Jun. 12, 2015.

(51) Int. Cl.
*G02B 6/34* (2006.01)
*G02B 6/124* (2006.01)
(Continued)

(52) U.S. Cl.
CPC ............ *G02B 6/124* (2013.01); *G01N 21/03* (2013.01); *G01N 21/648* (2013.01);
(Continued)

(58) Field of Classification Search
CPC . G02B 6/34; G02B 6/124; G02B 6/30; G02B 2006/12107; G02B 6/12014
See application file for complete search history.

(56) References Cited

U.S. PATENT DOCUMENTS

| 3,674,335 | A | | 7/1972 | Ashkin et al. |
| 3,916,182 | A | * | 10/1975 | Dabby ................. G02B 6/021 385/123 |

(Continued)

FOREIGN PATENT DOCUMENTS

| EP | 1105529 B1 | 11/2005 |
| EP | 1871902 B1 | 10/2006 |

(Continued)

OTHER PUBLICATIONS

Abbas et al. (2011) Sens. Actuators B Chem. 156:169-175.

(Continued)

*Primary Examiner* — Jennifer Doan
(74) *Attorney, Agent, or Firm* — VLP Law Group LLP

(57) ABSTRACT

Integrated target waveguide devices and optical analytical systems comprising such devices are provided. The target devices include an optical coupler that is optically coupled to an integrated waveguide and that is configured to receive optical input from an optical source through free space, particularly through a low numerical aperture interface. The devices and systems are useful in the analysis of highly multiplexed optical reactions in large numbers at high densities, including biochemical reactions, such as nucleic acid sequencing reactions. The devices provide for the efficient and reliable coupling of optical excitation energy from an optical source to the optical reactions. Optical signals emitted from the reactions can thus be measured with high sensitivity and discrimination. The devices and systems are well suited for miniaturization and high throughput.

28 Claims, 44 Drawing Sheets

(51) Int. Cl.
  *G01N 21/03* (2006.01)
  *G01N 21/64* (2006.01)
  *G01N 21/77* (2006.01)
  *G02B 6/42* (2006.01)
  *G02B 6/12* (2006.01)

(52) U.S. Cl.
  CPC ..... *G01N 21/6452* (2013.01); *G01N 21/6486* (2013.01); *G01N 21/774* (2013.01); *G02B 6/34* (2013.01); *G01N 21/7703* (2013.01); *G01N 2021/0346* (2013.01); *G02B 6/4221* (2013.01); *G02B 2006/12135* (2013.01)

(56) References Cited

U.S. PATENT DOCUMENTS

| | | | |
|---|---|---|---|
| 4,645,523 A | 2/1987 | Howard et al. | |
| 5,082,629 A | 1/1992 | Burgess, Jr. et al. | |
| 5,094,517 A | 3/1992 | Franke | |
| 5,132,843 A | 7/1992 | Aoyama et al. | |
| 5,135,876 A | 8/1992 | Andrade et al. | |
| 5,157,262 A | 10/1992 | Marsoner et al. | |
| 5,159,661 A | 10/1992 | Ovshinsky et al. | |
| 5,173,747 A | 12/1992 | Boiarski et al. | |
| 5,192,502 A | 3/1993 | Attridge et al. | |
| 5,195,152 A * | 3/1993 | Gupta | B41J 2/465 369/121 |
| 5,233,673 A | 8/1993 | Vali et al. | |
| 5,239,178 A | 8/1993 | Derndinger et al. | |
| 5,439,647 A * | 8/1995 | Saini | G01N 21/431 250/227.14 |
| 5,446,534 A | 8/1995 | Goldman | |
| 5,470,710 A | 11/1995 | Weiss et al. | |
| 5,502,781 A | 3/1996 | Li et al. | |
| 5,545,531 A | 8/1996 | Rava et al. | |
| 5,578,832 A | 11/1996 | Trulson et al. | |
| 5,605,662 A | 2/1997 | Heller et al. | |
| 5,631,734 A | 5/1997 | Stern et al. | |
| 5,677,196 A | 10/1997 | Herron et al. | |
| 5,695,934 A | 12/1997 | Brenner | |
| 5,744,305 A | 4/1998 | Fodor et al. | |
| 5,812,709 A | 9/1998 | Arai et al. | |
| 5,821,058 A | 10/1998 | Smith et al. | |
| 5,832,165 A | 11/1998 | Reichert et al. | |
| 5,867,266 A | 2/1999 | Craighead et al. | |
| 5,919,712 A | 7/1999 | Herron et al. | |
| 6,002,520 A | 12/1999 | Hoch et al. | |
| 6,071,748 A | 6/2000 | Modlin et al. | |
| 6,192,168 B1 | 2/2001 | Feldstein et al. | |
| 6,210,896 B1 | 4/2001 | Chan | |
| 6,236,945 B1 | 5/2001 | Simpson et al. | |
| 6,263,286 B1 | 7/2001 | Gilmanshin et al. | |
| 6,304,706 B1 | 10/2001 | Sugita et al. | |
| 6,325,977 B1 | 12/2001 | Theil | |
| 6,388,788 B1 | 5/2002 | Harris et al. | |
| 6,437,345 B1 | 8/2002 | Bruno-Raumandi et al. | |
| 6,438,279 B1 | 8/2002 | Craighead et al. | |
| 6,603,537 B1 | 8/2003 | Dietz et al. | |
| 6,611,634 B2 | 8/2003 | Herron et al. | |
| 6,690,002 B2 | 2/2004 | Kuroda et al. | |
| 6,699,655 B2 | 3/2004 | Nikiforov et al. | |
| 6,760,499 B2 | 7/2004 | Pezeshki et al. | |
| 6,784,982 B1 | 8/2004 | Blumenfeld et al. | |
| 6,800,860 B2 | 10/2004 | Dietz et al. | |
| 6,818,395 B1 | 11/2004 | Quake et al. | |
| 6,847,748 B2 | 1/2005 | Benzoni et al. | |
| 6,856,751 B2 | 2/2005 | Oaknin et al. | |
| 6,867,851 B2 | 3/2005 | Blumenfeld et al. | |
| 6,917,726 B2 | 7/2005 | Levene et al. | |
| 6,919,211 B1 | 7/2005 | Fodor et al. | |
| 6,973,232 B2 | 12/2005 | Betty et al. | |
| 6,979,830 B2 | 12/2005 | Dietz et al. | |
| 6,982,146 B1 | 1/2006 | Schneider et al. | |
| 6,987,613 B2 | 1/2006 | Pocius et al. | |
| 7,013,054 B2 | 3/2006 | Levene et al. | |
| 7,022,515 B2 | 4/2006 | Herron et al. | |
| 7,056,661 B2 | 6/2006 | Korlach et al. | |
| 7,057,832 B2 | 6/2006 | Wu et al. | |
| 7,058,261 B2 | 6/2006 | Ghiron et al. | |
| 7,058,275 B2 | 6/2006 | Sezerman et al. | |
| 7,065,272 B2 | 6/2006 | Taillaert et al. | |
| 7,075,695 B2 | 7/2006 | Gronbach | |
| 7,081,954 B2 | 7/2006 | Sandstrom | |
| 7,083,914 B2 | 8/2006 | Seul et al. | |
| 7,129,470 B2 * | 10/2006 | MacDougall | G01B 11/165 250/227.14 |
| 7,130,041 B2 | 10/2006 | Bouzid et al. | |
| 7,135,667 B2 | 11/2006 | Oldham et al. | |
| 7,139,074 B2 | 11/2006 | Reel | |
| 7,145,645 B2 | 12/2006 | Blumenfeld et al. | |
| 7,150,997 B2 | 12/2006 | Kovacs | |
| 7,162,124 B1 | 1/2007 | Gunn et al. | |
| 7,170,050 B2 | 1/2007 | Turner et al. | |
| 7,175,811 B2 | 2/2007 | Bach et al. | |
| 7,181,122 B1 | 2/2007 | Levene et al. | |
| 7,189,361 B2 | 3/2007 | Carson | |
| 7,194,166 B1 | 3/2007 | Gunn | |
| 7,197,196 B2 | 3/2007 | Lin et al. | |
| 7,199,357 B1 | 4/2007 | Oldham et al. | |
| 7,209,836 B1 | 4/2007 | Schermer et al. | |
| 7,227,128 B2 | 6/2007 | Sagatelyan | |
| 7,245,803 B2 | 7/2007 | Gunn et al. | |
| RE39,772 E | 8/2007 | Herron et al. | |
| 7,257,141 B2 | 8/2007 | Chua | |
| 7,265,840 B2 | 9/2007 | Cheng | |
| 7,283,705 B2 | 10/2007 | Paek et al. | |
| 7,298,941 B2 | 11/2007 | Palen et al. | |
| 7,302,348 B2 | 11/2007 | Ghosh et al. | |
| 7,315,019 B2 | 1/2008 | Turner et al. | |
| 7,323,681 B1 | 1/2008 | Oldham et al. | |
| 7,376,308 B2 | 5/2008 | Cheben et al. | |
| 7,400,380 B2 | 7/2008 | Hahn | |
| 7,486,865 B2 | 2/2009 | Foquet et al. | |
| 7,499,094 B2 | 3/2009 | Kuriyama | |
| 7,537,734 B2 | 5/2009 | Reichert et al. | |
| 7,684,660 B2 | 3/2010 | Braunisch et al. | |
| 7,709,808 B2 | 5/2010 | Reel et al. | |
| 7,767,441 B2 | 8/2010 | Chiou et al. | |
| 7,792,402 B2 | 9/2010 | Peng | |
| 7,811,810 B2 | 10/2010 | Chiou et al. | |
| 7,817,281 B2 | 10/2010 | Kiesel et al. | |
| 7,820,983 B2 | 10/2010 | Lundquist et al. | |
| 7,826,697 B2 | 11/2010 | Presley et al. | |
| 7,834,329 B2 | 11/2010 | Lundquist et al. | |
| 7,838,847 B2 | 11/2010 | Lundquist et al. | |
| 7,907,800 B2 | 3/2011 | Foquet et al. | |
| 8,053,742 B2 | 11/2011 | Lundquist et al. | |
| 8,207,509 B2 | 6/2012 | Lundquist et al. | |
| 8,247,216 B2 | 8/2012 | Zaccarin et al. | |
| 8,274,040 B2 | 9/2012 | Zhong et al. | |
| 8,411,375 B2 | 4/2013 | Lenchenkov | |
| 8,447,150 B2 | 5/2013 | Kopp | |
| 8,465,699 B2 | 6/2013 | Fehr et al. | |
| 8,467,061 B2 | 6/2013 | McCaffrey et al. | |
| 8,471,219 B2 | 6/2013 | Lundquist et al. | |
| 8,594,503 B2 | 11/2013 | Roelkens et al. | |
| 8,618,507 B1 | 12/2013 | Lundquist et al. | |
| 8,865,077 B2 | 10/2014 | Chiou et al. | |
| 8,883,018 B2 | 11/2014 | Doerr | |
| 8,899,848 B2 | 12/2014 | Rossetto | |
| 8,906,320 B1 | 12/2014 | Eltoukhy et al. | |
| 9,029,802 B2 | 5/2015 | Lundquist et al. | |
| 9,223,084 B2 | 12/2015 | Grot et al. | |
| 9,372,308 B1 | 6/2016 | Saxena et al. | |
| 2002/0034457 A1 | 3/2002 | Reichert et al. | |
| 2002/0110839 A1 | 8/2002 | Bach et al. | |
| 2002/0113213 A1 | 8/2002 | Amirkhanian et al. | |
| 2002/0146047 A1 | 10/2002 | Bendett et al. | |
| 2003/0044781 A1 | 3/2003 | Korlach et al. | |
| 2003/0132406 A1 | 7/2003 | Waldhausl et al. | |
| 2003/0138180 A1 | 7/2003 | Kondo | |
| 2003/0174324 A1 | 9/2003 | Sandstrom | |
| 2003/0174992 A1 | 9/2003 | Levene et al. | |
| 2004/0040868 A1 | 3/2004 | Denuzzio et al. | |

(56) References Cited

U.S. PATENT DOCUMENTS

| | | |
|---|---|---|
| 2004/0046128 A1 | 3/2004 | Abel et al. |
| 2004/0156590 A1 | 8/2004 | Gunn et al. |
| 2004/0197793 A1 | 10/2004 | Hassibi et al. |
| 2004/0249227 A1 | 12/2004 | Klapproth et al. |
| 2005/0006607 A1 | 1/2005 | Winter et al. |
| 2005/0014178 A1 | 1/2005 | Holm-Kennedy |
| 2005/0018970 A1 | 1/2005 | Tseng et al. |
| 2005/0135974 A1 | 6/2005 | Harvey et al. |
| 2005/0175273 A1 | 8/2005 | Iida et al. |
| 2005/0201899 A1 | 9/2005 | Weisbuch |
| 2005/0206895 A1 | 9/2005 | Salmelainen |
| 2006/0060766 A1 | 3/2006 | Turner et al. |
| 2006/0083469 A1 | 4/2006 | Faid et al. |
| 2006/0103850 A1 | 5/2006 | Alphonse et al. |
| 2006/0180750 A1 | 8/2006 | Gollier et al. |
| 2007/0036511 A1 | 2/2007 | Lundquist et al. |
| 2007/0099212 A1 | 5/2007 | Harris |
| 2007/0134128 A1 | 6/2007 | Korlach |
| 2007/0146701 A1 | 6/2007 | Kiesel et al. |
| 2007/0188746 A1 | 8/2007 | Kraus et al. |
| 2007/0196815 A1 | 8/2007 | Lappe et al. |
| 2008/0002929 A1 | 1/2008 | Bowers et al. |
| 2008/0020938 A1 | 1/2008 | Kaplan |
| 2008/0039339 A1 | 2/2008 | Hassibi et al. |
| 2008/0056950 A1 | 3/2008 | Weisbuch et al. |
| 2008/0161195 A1 | 7/2008 | Turner et al. |
| 2008/0176769 A1 | 7/2008 | Rank et al. |
| 2008/0212960 A1 | 9/2008 | Lundquist et al. |
| 2009/0146076 A1 | 6/2009 | Chiou et al. |
| 2009/0181396 A1 | 7/2009 | Luong et al. |
| 2009/0208957 A1 | 8/2009 | Korlach et al. |
| 2009/0247414 A1 | 10/2009 | Obradovic |
| 2009/0311774 A1 | 12/2009 | Chiou et al. |
| 2009/0317074 A1 | 12/2009 | Tan et al. |
| 2010/0065726 A1 | 3/2010 | Zhong et al. |
| 2010/0099100 A1 | 4/2010 | Zaccarin et al. |
| 2010/0121582 A1 | 5/2010 | Pan et al. |
| 2010/0163521 A1 | 7/2010 | Balamane et al. |
| 2010/0255488 A1 | 10/2010 | Kong et al. |
| 2010/0256918 A1 | 10/2010 | Chen et al. |
| 2010/0295083 A1 | 11/2010 | Celler |
| 2011/0117637 A1 | 5/2011 | Gray et al. |
| 2011/0183409 A1 | 7/2011 | Newby et al. |
| 2011/0210094 A1 | 9/2011 | Gray et al. |
| 2011/0222179 A1 | 9/2011 | Monadgemi |
| 2011/0223590 A1 | 9/2011 | Chiou et al. |
| 2011/0257040 A1 | 10/2011 | Turner et al. |
| 2011/0306039 A1 | 12/2011 | Chiou et al. |
| 2012/0014837 A1 | 1/2012 | Fehr et al. |
| 2012/0019828 A1 | 1/2012 | McCaffrey et al. |
| 2012/0021525 A1 | 1/2012 | Fehr et al. |
| 2012/0052506 A1 | 3/2012 | Yue et al. |
| 2012/0058469 A1 | 3/2012 | Shen et al. |
| 2012/0058473 A1 | 3/2012 | Yue et al. |
| 2012/0058482 A1 | 3/2012 | Shen et al. |
| 2012/0077189 A1 | 3/2012 | Shen et al. |
| 2012/0085894 A1 | 4/2012 | Zhong et al. |
| 2012/0156100 A1 | 6/2012 | Tsai et al. |
| 2013/0043552 A1 | 2/2013 | Lazarov et al. |
| 2013/0148682 A1 | 6/2013 | Zhang et al. |
| 2014/0177995 A1 | 6/2014 | Mohammed et al. |
| 2014/0193115 A1 | 7/2014 | Popovic |
| 2014/0193331 A1 | 7/2014 | Naczynski et al. |
| 2014/0241682 A1 | 8/2014 | Sandhu et al. |
| 2014/0287964 A1 | 9/2014 | Lundquist et al. |
| 2014/0348462 A1 | 11/2014 | Yabre |
| 2014/0353577 A1 | 12/2014 | Agarwal et al. |
| 2015/0001175 A1 | 1/2015 | Rabiei |
| 2015/0141267 A1 | 5/2015 | Rothberg et al. |
| 2015/0286060 A1 | 10/2015 | Roh et al. |
| 2016/0061740 A1 | 3/2016 | Grot et al. |
| 2016/0084761 A1 | 3/2016 | Rothberg et al. |
| 2016/0154165 A1 | 6/2016 | Grot et al. |
| 2016/0273034 A1 | 9/2016 | Lundquist et al. |

FOREIGN PATENT DOCUMENTS

| | | |
|---|---|---|
| EP | 2362209 A2 | 8/2011 |
| KR | 10-2005-0088782 A | 9/2005 |
| WO | WO 1991006678 A1 | 5/1991 |
| WO | WO 2000052518 A1 | 9/2000 |
| WO | WO 2001016375 A2 | 3/2001 |
| WO | WO 2004100068 A2 | 11/2004 |
| WO | WO 2006116726 A2 | 2/2006 |
| WO | WO 2006135782 A2 | 12/2006 |
| WO | WO 2007002367 A2 | 1/2007 |
| WO | WO 2007011549 A1 | 1/2007 |
| WO | WO 2008002765 A2 | 1/2008 |
| WO | WO 2009056065 A1 | 5/2009 |
| WO | WO 2009131535 A1 | 10/2009 |
| WO | WO 2009149125 A2 | 12/2009 |
| WO | WO 2010051773 A1 | 5/2010 |
| WO | WO 2010102567 A1 | 9/2010 |
| WO | WO 2011076132 A2 | 6/2011 |
| WO | WO 2011126718 A1 | 10/2011 |
| WO | WO 2012064472 A2 | 5/2012 |
| WO | WO 2013037900 A1 | 3/2013 |
| WO | WO 2014031157 A1 | 2/2014 |

OTHER PUBLICATIONS

Barrios (2006) IEEE Photon Technol. Lett. 18:2419.
Barrios et al. (2007) Optics Letters 32:3080.
Barrios et al. (2008) Optics Letters 33:708.
Bernini et al. (2005) Proc. SPIE 5728:101-111.
Boiarski et al. (1992) Proc. SPIE 1793:199-211.
Budach et al. (1999) Anal. Chem. 71(16):3347-3355.
Chen et al. (2012) Optics Letters 37:2814.
Cottier et al. (2002) Proc. SPIE 4616:53-63.
Deopura, M. et al. (2001) Optics Lett 26(15):1197-1199.
Duveneck et al. (2002) Anal Chem Acta 469:49-61.
Eid et al. (2009) Science 323:133.
Feldstein et al. (1999) J. Biomed Microdev. 1:139-153.
Feng et al. (2006) IEEE J. Quantum Electron. 42:885.
Feng et al. (2007) Optics Letters 32:2131.
Fink, Y. et al. (1998) Science 282:1679-1682.
Fonollosa et al. (2006) Proceedings of SPIE 61860R-1: 61860R-11.
Fujikura Ltd. (2014) Introduction of PANDA Fibers 1-57.
Heng (2011) Phys Org 6 "Silicon Waveguide that Converts Polarization Mode of Light Could Speed Up Photonic Circuits Operation".
Herron et al. (2003) Biopolymers at Interfaces 2nd Ed, Surfactant Science Series vol. 110, Marcel Dekker, NY pp. 115-163.
Laurell et al. (2012) Optics Express 20:22308.
Levene, M.J. et al. (2003) Science 299:682-686.
Li et al. (2004) Electronic Components and Technology Conference 1925-1928 "Photolithography of 3D Topology in Si Optical Bench for Self-aligned Placement of Laser Dies".
Mortazavi et al. (1994) Optics Letters 19:1290.
Nava et al. (2010) Electronics Letters 46:1686.
Pan et al. (2011) Optics Communications 284:429.
Psaltis et al. (2006) Nature 442:381.
Robinson et al. (2008) Optics Express 16:4296.
Romero-Garcia (2013) Optics Express 21(12):14036-14046.
Sahin et al. (2011) J. Nanophoton. 5:051812.
Salama et al. (2004) Biosensors & Bioelectronics 19:1377-1386.
Song et al. (2012) Optics Express 20:22290.
Sun et al. (2007) Optics Express 15:17967.
Tuma et al. (1995) NASA Lewis Research Center 1-13 "Calculated Coupling Efficiency Between an Elliptical-core Optical Fiber and a Silicon Oxynitride Rib Waveguide".
Van Laere et al. (2006) Photonics "Compact Focusing Grating Couplers Between Optical Fibers and Silicon-on-Insulator Photonic Wire Waveguides".
Van Laere et al. (2007) Journal of Lightwave Technology 25(1):151-156.
Waldhausl et al. (1997) Applied Optics 36(36):9383-9390.
Weissman et al. (1999) Proc. SPIE 3596:210-216.
Wu et al. (2006) Biosensors and Bioelectronics 21:1252-1263.

(56) References Cited

OTHER PUBLICATIONS

Yao et al. (2012) Nonlinear Optics and Solid-State Lasers, Springer-Verlag Berlin Heidelberg, Chapter 5.
Yariv, A. et al. (1977) IEEE J Quantum Elec QE-13(4):233-253.
Zhang et al. (2010) Optics Express 18(24):25264-25270.
International Search Report and Written Opinion dated Sep. 9, 2016 for related PCT/US2016/037106.
Franc et al. (2006) Proceedings of SPIE 6185:61851F (DOI: 10.1117/12.666710).
Kempen et al. (1997) Sensors and Actuators B 39:295 (DOI: 10.1016/S0925-4005(97)80222-5).
Supplementary partial European search report and opinion dated Oct. 17, 2018 in related European Application No. EP 16 808488.7.

* cited by examiner

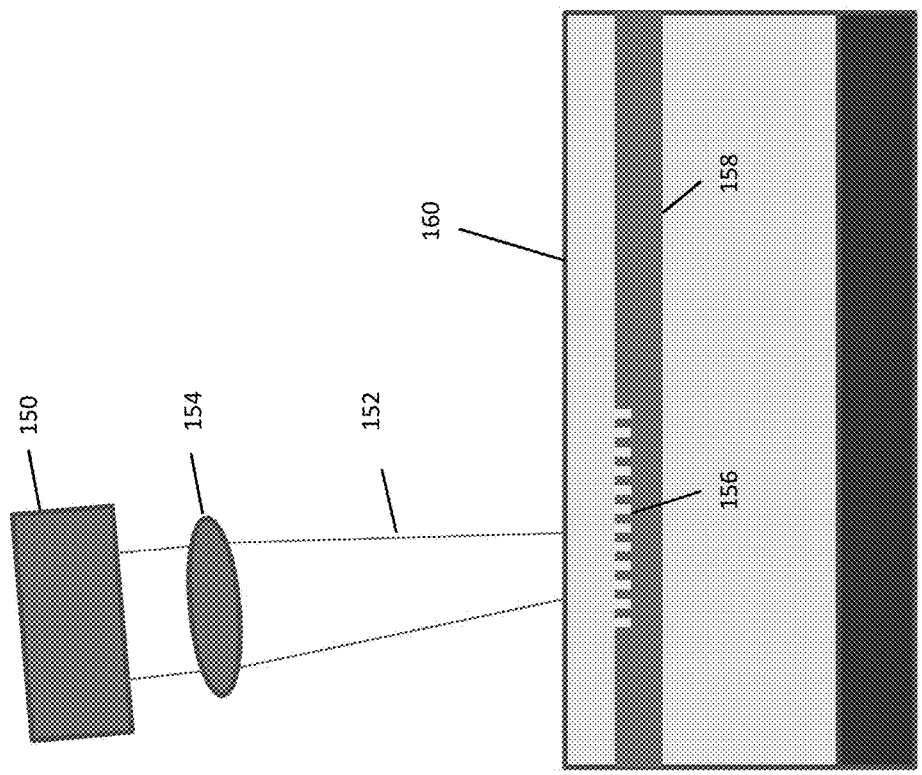
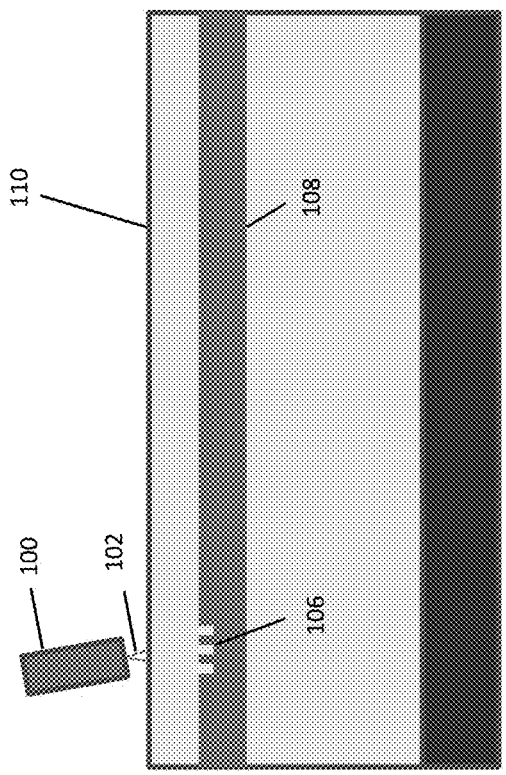
FIG. 1B
FIG. 1A

Bottom side etched
$\eta_{max} \sim 21\%$

Double side etched
$\eta_{max} \sim 53\%$

SiN overlay layer $\eta_{max} \sim 40\%$
SiC overlay layer $\eta_{max} \sim 57\%$ SiC overlay layer, double side etched
$\eta_{max} \sim 65\%$

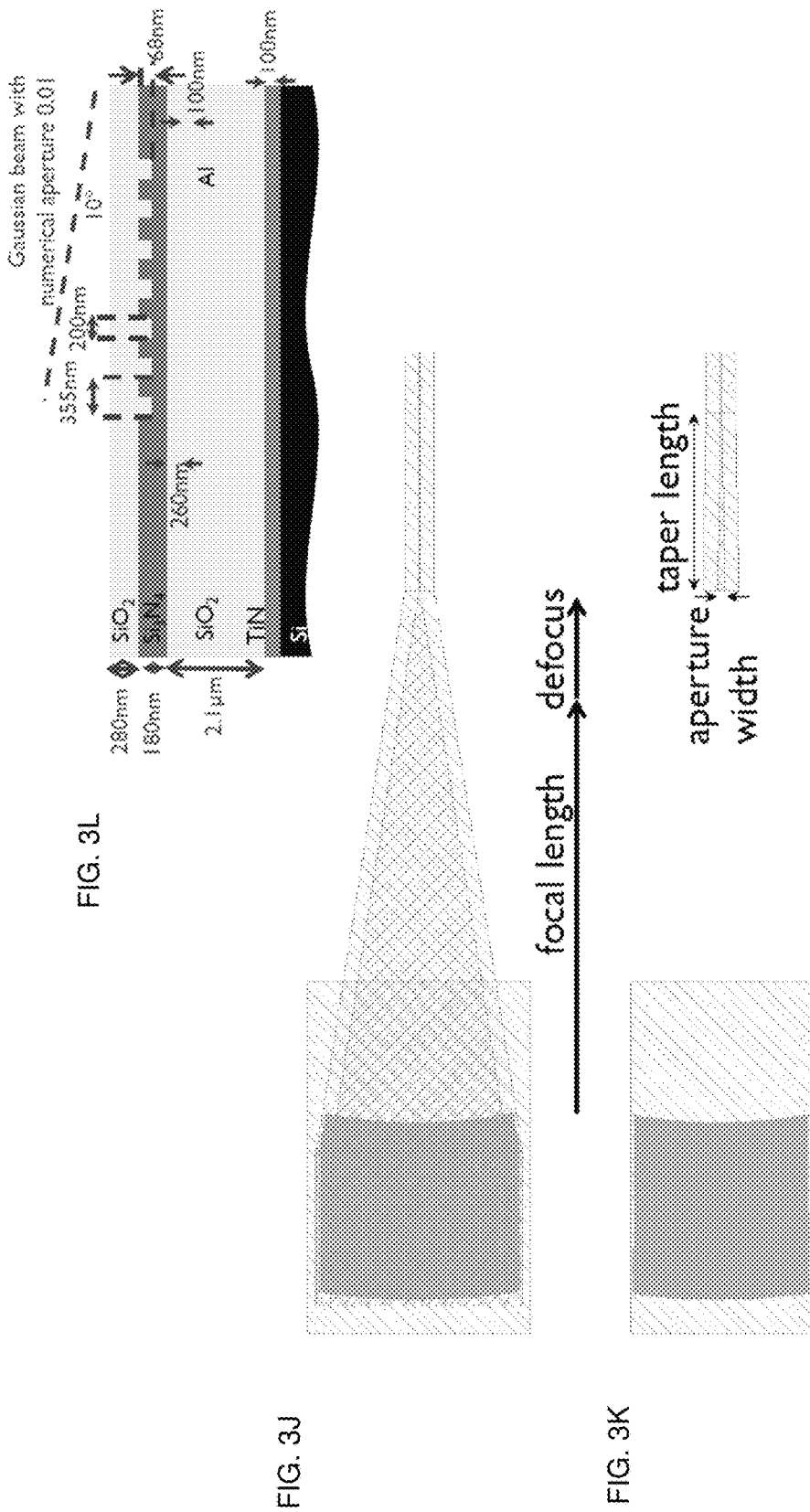

34, 11.4, and 30.5 microns for a, b, and c, respectively

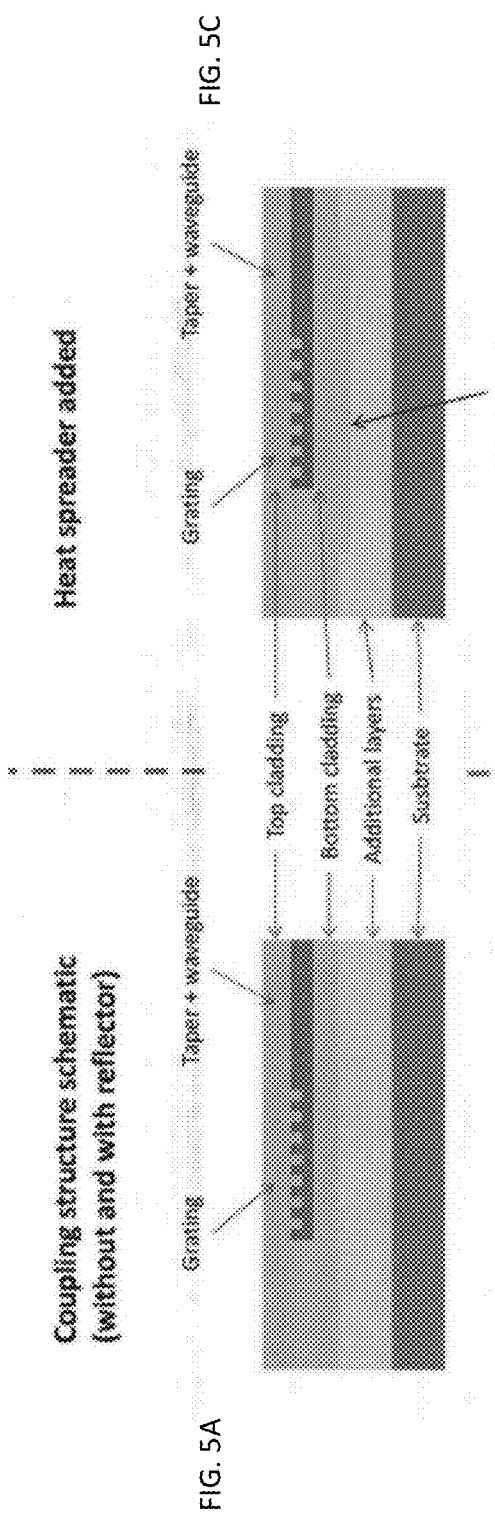

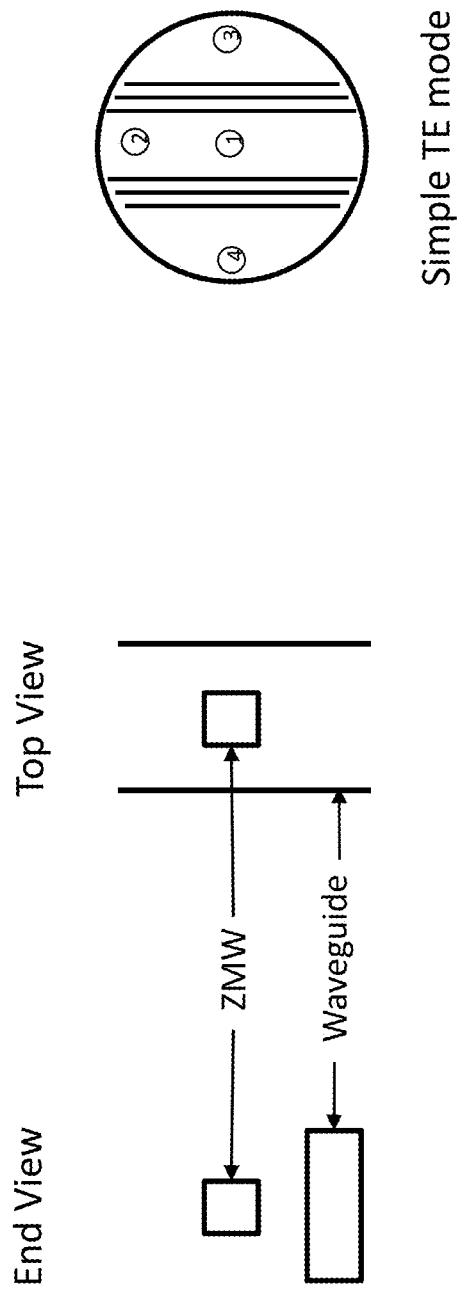
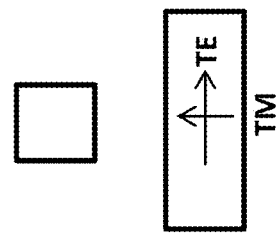
FIG. 9
FIG. 10

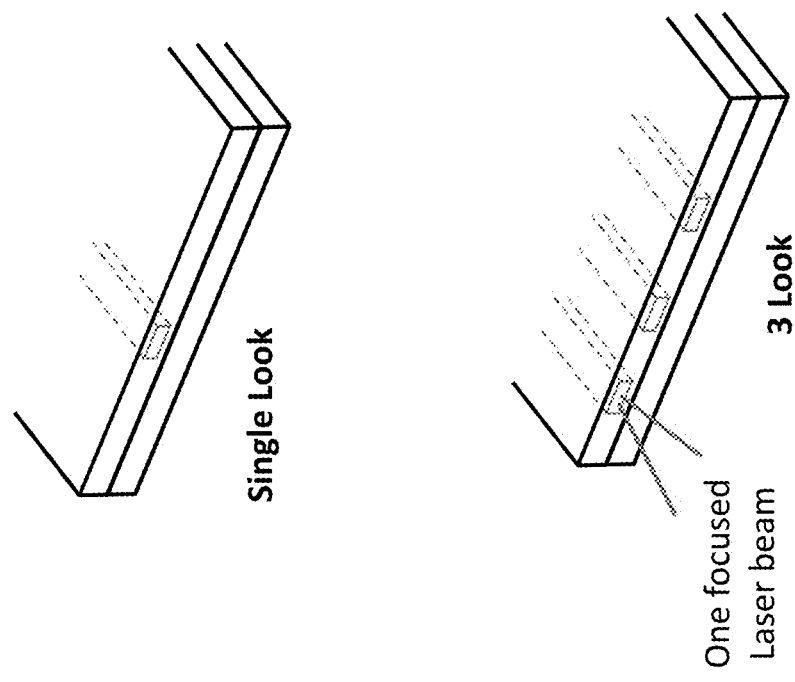
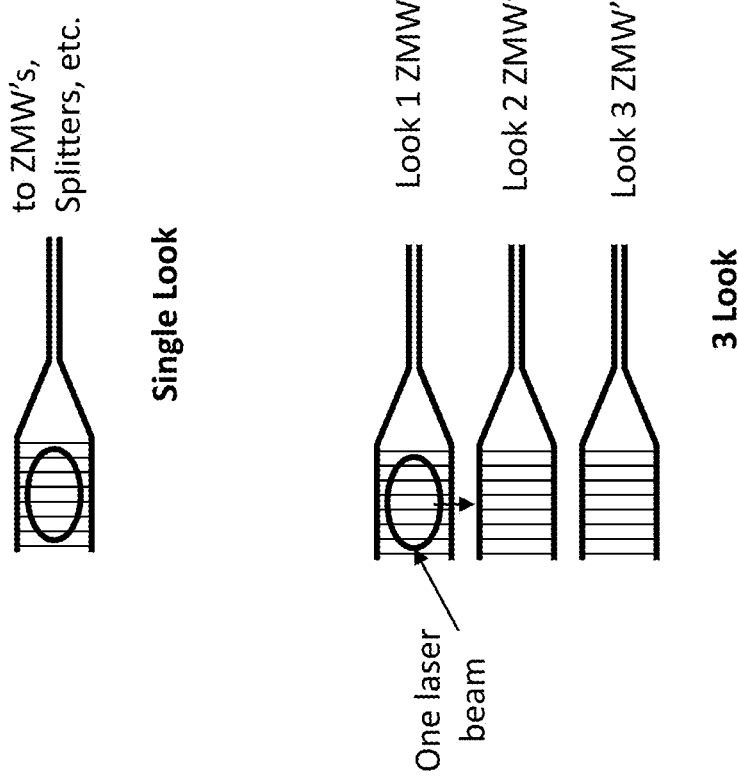

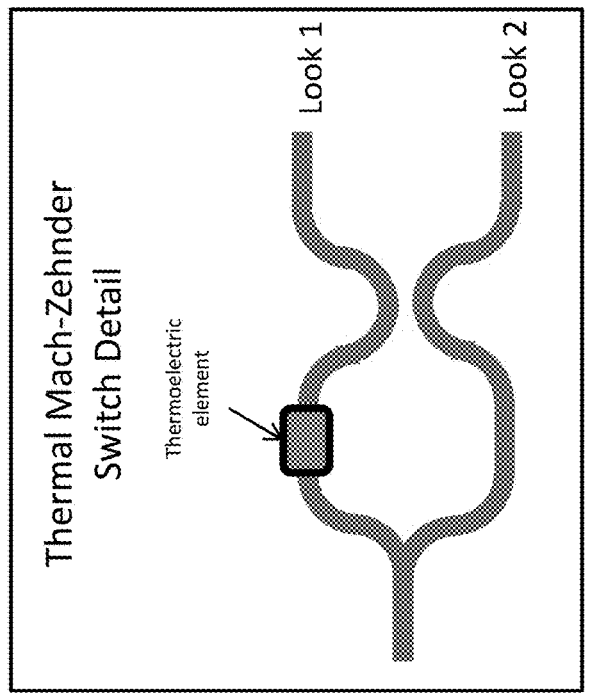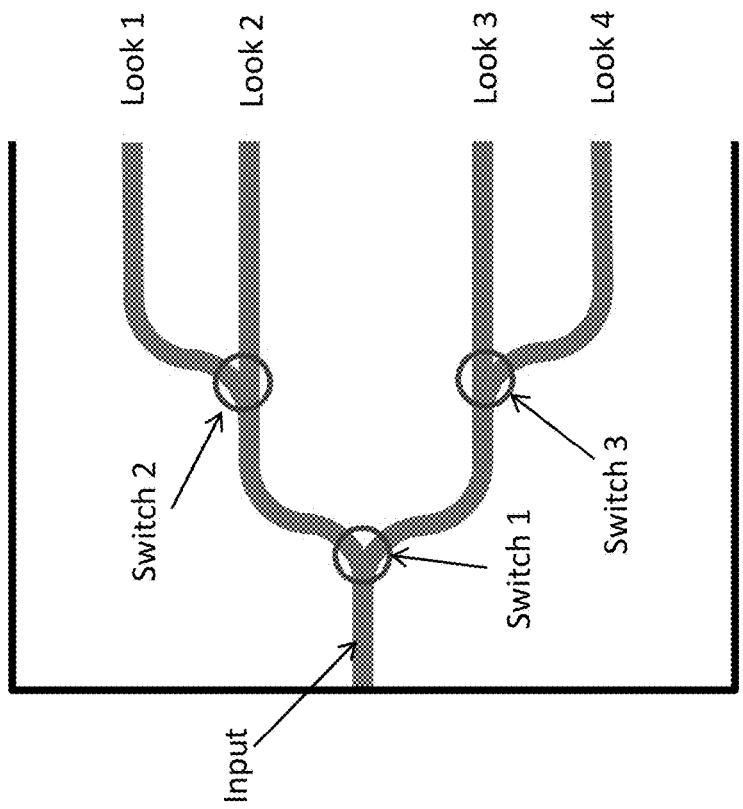
FIG. 13

| Designs | Top oxide thk (um) | Bot oxide thk (um) | grating teeth pair # | Period (nm) | Duty cycle | Top etch depth (nm) | Bot etch Bot etch depth (nm) | grating shift to | Overlay thk (nm) | Overlay etch width (nm) | Overlay index |
|---|---|---|---|---|---|---|---|---|---|---|---|
| Top side etch | 800 | 2.155 | 10 | 377.5 | 0.515 | 152.4 | | | - | - | - |
| Top side etch | 800 | 2.149 | 20 | 378 | 0.516 | 147.2 | | | - | - | - |
| Top side etch | 800 | 2.129 | 20 | 374.6 | 0.484 | 157.4 | | | - | - | - |
| Bot side etch | 800 | 1.964 | 10 | 334.5 | 0.447 | | 160 | | - | - | - |
| Bot side etch, top centered | 800 | 1.954 | 10 | 336 | 0.413 | | 166.9 | | - | - | - |
| 2-side etch | 800 | 2.124 | 10 | 383 | 0.467 | 103.9 | 103.9 | | - | - | - |
| 2-side etch, shifted | 800 | 2.147 | 10 | 387 | 0.523 | 107.1 | 57.6 | 0.899 | - | - | - |
| SiN overlay, top side etch | 800 | 2.14 | 10 | 363.7 | 0.52 | 137.6 | | | 23.6 | 230 | 1.9085 |
| SiC overlay, top side etch | 800 | 2.08 | 10 | 308 | 0.43 | 97 | | | 57.8 | 113.9 | 2.6 |
| SiC overlay, 2-side etch, shifted | 800 | 2.235 | 10 | 317.9 | 0.524 | 8 | 160 | 0.795 | 200 | 38.8 | 2.6 |
| SiC overlay, 2-side etch, shifted | 800 | 2.066 | 10 | 340 | 0.42 | 87 | 308 | 0.9 | 108 | 108 | 2.6 |

FIG. 18

| Designs | Large GC, NA=0.13 | Large GC, NA=0.05 | Large GC, NA=0.015 | Large GC, NA=0.01 |
|---|---|---|---|---|
| waveguide core thk (nm) | 180 | 180 | 180 | 180 |
| Top oxide thk (nm) | 800 | 800 | 800 | 800 |
| Bottom oxide thk (um) | 2.11 | 2.11 | 2.11 | 2.11 |
| beam waist specified in Lumerical (um) | 1.303 | 3.387 | 11.289 | 16.934 |
| recommended source size by calculation (um) | 5.21 | 13.55 | 45.16 | 67.74 |
| Actual source size in Lumerical (um) | 6.00 | 15.00 | 45.00 | 68.00 |
| recommended grating size by calculation (um) | 3.91 | 10.16 | 33.87 | 50.80 |
| grating size in lumerical simulation (um) | 3.66 | 10.95 | 18.65 | 29.84 |
| | | | | |
| | | | | |
| | | | | |
| | | | | |
| index, nitride core | 1.9085 | 1.9085 | 1.9085 | 1.9085 |
| index, oxide clad | 1.46 | 1.46 | 1.46 | 1.46 |
| index, silicon substrate | Lum model | Lum model | Lum model | Lum model |
| | | | | |

FIG. 19

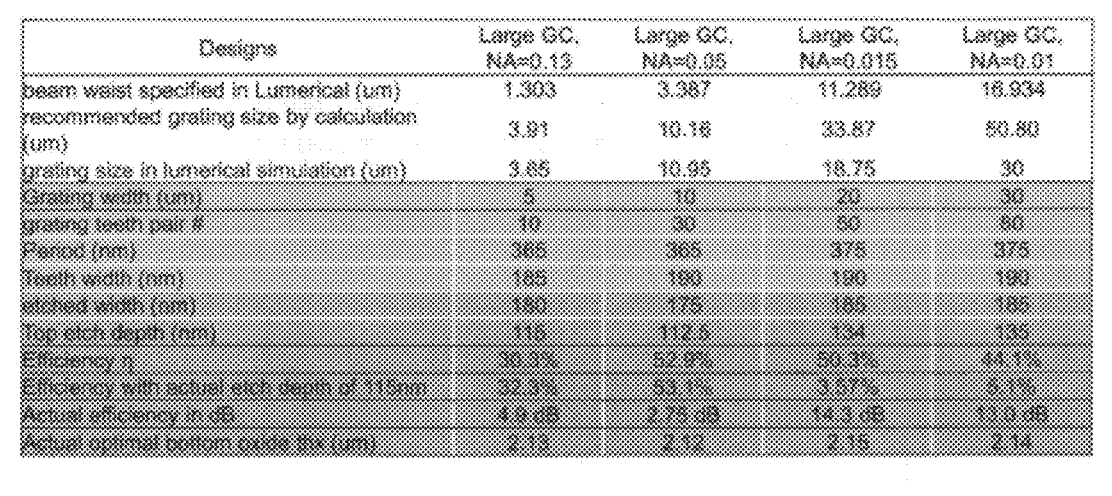

| Designs | Large GC, NA=0.13 | Large GC, NA=0.05 | Large GC, NA=0.015 | Large GC, NA=0.01 |
|---|---|---|---|---|
| beam waist specified in Lumerical (um) | 1.303 | 3.387 | 11.289 | 16.934 |
| recommended grating size by calculation (um) | 3.91 | 10.16 | 33.87 | 50.80 |
| grating size in Lumerical simulation (um) | 3.85 | 10.95 | 18.75 | 30 |

FIG. 22

FIG. 29A  FIG. 29B
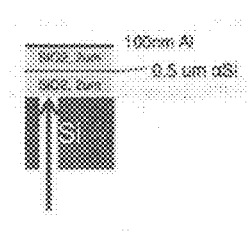 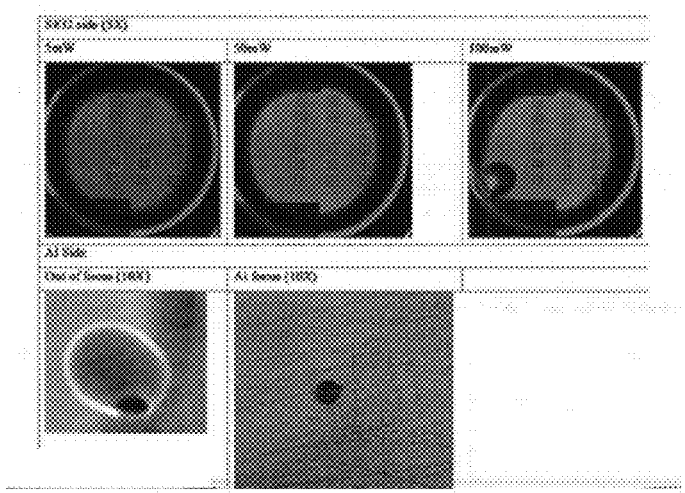
FIG. 29C  FIG. 29D
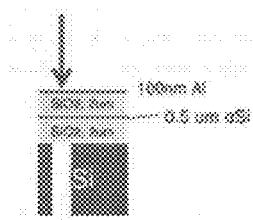 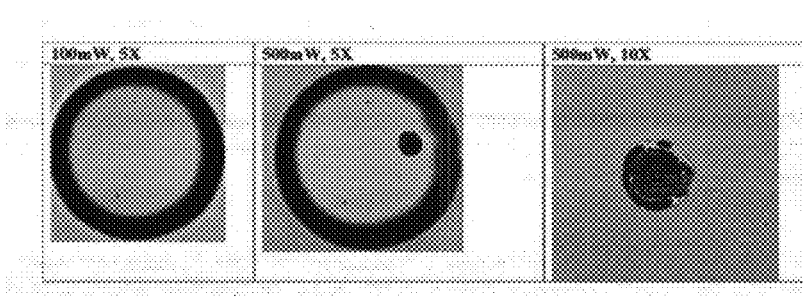

INTEGRATED TARGET WAVEGUIDE DEVICES AND SYSTEMS FOR OPTICAL COUPLING

CROSS-REFERENCE TO RELATED APPLICATIONS

This application claims the benefit of U.S. Provisional Application No. 62/175,139, filed on Jun. 12, 2015, the disclosure of which is incorporated herein by reference in its entirety.

BACKGROUND OF THE INVENTION

As multiplexed optical analytical systems continue to be miniaturized in size, expanded in scale, and increased in power, the need to develop improved systems capable of delivering optical energy to such systems becomes more important. For example, highly multiplexed analytical systems comprising integrated waveguides for the illumination of nanoscale samples are described in U.S. Patent Application Publication Nos. 2008/0128627 and 2012/0085894. Further optical systems for the analysis of nanoscale samples, including the illumination and detection of such samples, are described in U.S. Patent Application Publication Nos. 2012/0014837, 2012/0021525, and 2012/0019828. Additional nanoscale illumination systems for highly multiplexed analysis are described in U.S. Patent Application Publication Nos. 2014/0199016 and 2014/0287964.

In conventional optical systems, optical trains are typically employed to direct, focus, filter, split, separate, and detect light to and from the sample materials. Such systems typically employ an assortment of different optical elements to direct, modify, and otherwise manipulate light entering and leaving a reaction site. Such systems are frequently complex and costly and tend to have significant space requirements. For example, typical systems employ mirrors and prisms in directing light from its source to a desired destination. Additionally, such systems can include light-splitting optics such as beam-splitting prisms to generate two or more beams from a single original beam.

Alternatives to the conventional optical systems have been described, in particular alternative systems having integrated optical components designed and fabricated within highly confined environments. For example, planar lightwave circuits (PLCs) comprising fiber interfaces, wavelength filters or combiners, phase-delayed optical interferometers, optical isolators, polarization control, and/or taps have been developed for use in telecommunications applications. In some cases these devices additionally include one or more laser sources and one or more optical detectors. The devices, which are sometimes also referred to as fiber spacing concentrators (FSCs), use integrated optical waveguides to route photons through an optical circuit, in much the same way as electrons are routed through an electrical circuit. They are fabricated using standard semiconductor fabrication techniques, and they can accordingly integrate both passive components, such as optical filters and fiber pigtail connectors, and active elements, such as optical switches and attenuators, during the fabrication process. As used in telecommunications equipment, they typically serve to couple and/or split optical signals from fiber optic cores, for the purpose of, for example, multiplexing/demultiplexing, optical branching, and/or optical switching. The devices thus provide the functionality of a more traditional optical train, while at the same time being significantly less expensive, more compact, and more robust.

In the just-described optical systems, an optical source and its target device are typically closely and permanently associated with one another within the system. For example, PLCs used in telecommunications applications are typically mechanically aligned and bonded to their laser light source and to their associated photodetectors during the manufacturing process. Such close and irreversible associations between an optical source and its target device are thus not well suited for use in analytical systems having a removable sample holder, where the optical output from an optical source, such as a traditional optical train, is normally coupled to the target sample holder through free space. In systems optically coupled through free space, the optical signal from an optical source needs to be aligned with a target device each time the target device is replaced, and the alignment can even need to be monitored and maintained during the course of an analysis, due to mechanical, thermal, and other interfering factors associated with the optical system. In addition, the integrated optical circuits typically used in telecommunications applications are not designed to carry the intensity of optical energy necessary to analyze the large numbers of nanoscale samples present in the highly-multiplexed analytical systems described above, nor are they designed for use with optical sources having wavelengths suitable for use in optical systems with standard biological reagents.

Another consideration in the design of an optical analytical system is the method of coupling of light from the optical source into the target device. For example, where a target device comprises an integrated optical waveguide for routing the optical energy through the device, launching of the optical energy into the waveguide can be unreliable and inefficient. Various optical couplers have been described to achieve this purpose, including the use of direct "endfire" coupling into a polished end of the waveguide, the use of a prism coupler to direct light into the waveguide, and the use of a grating coupler to direct light into the waveguide. Depending on the implementation, however, each approach has limitations with respect to efficiency, reliability, applicability, cost, and the like.

There is thus a continuing need to improve the performance and properties of integrated optical waveguide devices, particularly those that are reversibly coupled to external light sources. There is also a need to improve the performance and properties of optical analytical systems containing such integrated waveguide devices.

SUMMARY OF THE INVENTION

The present disclosure addresses these and other needs by providing in one aspect an integrated target waveguide device comprising an optical coupler and an integrated waveguide optically coupled to the optical coupler. In this device, the optical coupler is a low numerical aperture coupler and is at least 100 $\mu m^2$ in size.

In another aspect, the disclosure provides an integrated target waveguide device comprising an optical coupler, an integrated waveguide optically coupled to the optical coupler, and at least one alignment feature. In this device, the optical coupler is also a low numerical aperture coupler and is also at least 100 $\mu m^2$ in size.

In yet another aspect, the disclosure provides an optical analytical system comprising an optical source and any of the integrated target waveguide devices disclosed herein. In this system, the optical source is optically coupled to the optical coupler of the target waveguide device through free space at a distance of at least 1 mm.

BRIEF DESCRIPTION OF THE DRAWINGS

FIGS. 1A-1C illustrate differences between coupling from an optical source with high numerical aperture, such as a fiber tip, and coupling from an optical source with low numerical aperture through free space to a target waveguide device.

FIGS. 3C to 3L show alternative optical grating coupler designs and structural features.

FIGS. 5A-5D illustrate exemplary grating couplers. FIG. 5A shows a basic grating coupler. FIG. 5B shows a structure that includes an optical reflective layer directly below the coupler. FIG. 5C shows a structure with a heat spreading layer directly below the coupler. FIG. 5D shows a structure with both a reflective layer and a heat spreading layer below the coupler.

FIG. 9 shows the effect of excitation with different TE modes on targets at different locations in a nanowell/ZMW.

FIG. 10 shows the pattern of TE, TM, and TEM modes in a rectangular waveguide

FIGS. 11A-11B illustrate single-look and multi-look coupling with grating-coupled waveguide devices (A) and endfire-coupled waveguide devices (B).

FIG. 13 illustrates the use of thermal Mach-Zehnder switches to control multi-look illumination in an endfire-coupled target device.

FIG. 18 provides a comparison of coupling efficiencies for various binary grating coupler designs.

FIG. 19 provides a comparison of coupling efficiencies for various binary grating coupler designs with different numerical aperture values.

FIG. 22 summarizes the simulated efficiencies of exemplary couplers designed and simulated using the parameters shown.

FIGS. 29A-29G show the results of testing samples containing a heat-spreading layer.

DETAILED DESCRIPTION OF THE INVENTION

Optical Analytical Systems

Figure 1C:
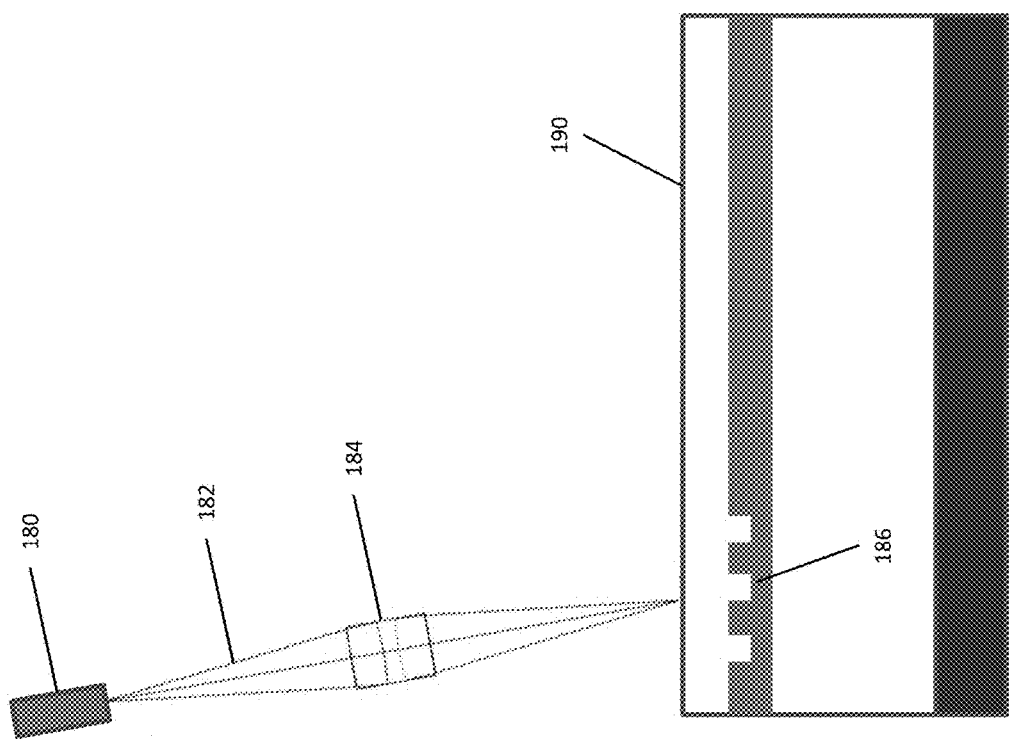

Multiplexed optical analytical systems are used in a wide variety of different applications. Such applications can include the analysis of single molecules, and can involve observing, for example, single biomolecules in real time as they interact with one another. For ease of discussion, such multiplexed systems are discussed herein in terms of a preferred application: the analysis of nucleic acid sequence information, and particularly, in single-molecule nucleic acid sequence analysis. Although described in terms of a particular application, however, it should be appreciated that the devices and systems described herein are of broader application.

In the context of single-molecule nucleic acid sequencing analyses, a single immobilized nucleic acid synthesis complex, comprising a polymerase enzyme, a template nucleic acid whose sequence is being elucidated, and a primer sequence that is complementary to a portion of the template sequence, is observed analytically in order to identify individual nucleotides as they are incorporated into the extended primer sequence. Incorporation is typically monitored by observing an optically detectable label on the nucleotide, prior to, during, or following its incorporation into the extended primer. In some cases, such single molecule analyses employ a "one base at a time approach", whereby a single type of labeled nucleotide is introduced to and contacted with the complex at a time. In some cases, unincorporated nucleotides are washed away from the complex following the reaction, and the labeled incorporated nucleotides are detected as a part of the immobilized complex. In other cases, it is possible to monitor the incorporation of nucleotides in real time without washing away unincorporated nucleotides.

In order to obtain the volumes of sequence information that can be desired for the widespread application of genetic sequencing, e.g., in research and diagnostics, higher throughput systems are desired. By way of example, in order to enhance the sequencing throughput of the system, multiple complexes are typically monitored, where each complex sequences a separate DNA template. In the case of genomic sequencing or sequencing of other large DNA components, these templates typically comprise overlapping fragments of genomic DNA. By sequencing each fragment, a contiguous sequence can thus be assembled using the overlapping sequence data from the separate fragments.

A single template/DNA polymerase-primer complex of such a sequencing system can be provided, typically immobilized, within a nanoscale, optically-confined region on or near the surface of a transparent substrate, optical waveguide, or the like. Such an approach is described in U.S. Pat. No. 7,056,661, which is incorporated by reference herein in its entirety. These optically-confined regions are preferably fabricated as nanoscale sample wells, also known as nanoscale reaction wells, nanowells, or zero mode waveguides (ZMWs), in large arrays on a suitable substrate in order to achieve the scale necessary for genomic or other large-scale DNA sequencing approaches. Such arrays preferably also include an associated optical source or sources, to provide excitation energy, an associated emission detector or detectors, to collect optical energy emitted from the samples, and associated electronics. Together, the components thus comprise a fully operational optical analytical device or system. Examples of analytical devices and systems useful in single-molecule nucleic acid sequence analysis include those described in U.S. Pat. Nos. 6,917,726, 7,170,050, and 7,935,310; U.S. Patent Application Publication Nos. 2012/0014837, 2012/0019828, and 2012/0021525; and U.S. patent application Ser. No. 13/920,037, which are each incorporated by reference herein in their entireties.

In embodiments, the instant optical analytical systems comprise an optical source that is coupled to a target device, typically an integrated target waveguide device. As will be described in more detail below, the optical source and the associated target device are configured for efficient coupling through free space, for example at a distance of at least 1 mm, at least 2 mm, at least 3 mm, at least 5 mm, at least 10 mm, at least 20 mm, at least 30 mm, at least 50 mm, or even at least 100 mm.

As will also be described in more detail below, it can be advantageous in the efficient coupling of optical energy from the optical source to the target device for the optical devices to be configured with low numerical aperture. By "low numerical aperture" it is meant that the numerical aperture is lower than the numerical aperture of near-field coupled optical devices. Specifically, it is meant that the numerical aperture is no more than 0.1. Accordingly, in some system embodiments, the optical source and the associated target device have numerical apertures of no more than 0.1, no more than 0.08, no more than 0.05, no more than 0.03, no more than 0.02, or even no more than 0.01. Furthermore, in some embodiments, the optical source is configured to illuminate a spot on the associated target device with a surface area per spot of at least 100 $\mu m^2$, at least 144 $\mu m^2$, at least 225 $\mu m^2$, at least 400 $\mu m^2$, at least 625 $\mu m^2$, at least 900 $\mu m^2$, at least 1600 $\mu m^2$, at least 2500 $\mu m^2$, at least 4900

µm², at least 10,000 µm², or even higher. In other embodiments, the optical source is configured to illuminate a spot on the associated target device with a surface area per spot of at most 250,000 µm², at most 62,500 µm², at most 22,500 µm², at most 10,000 µm², at most 6400 µm², at most 3600 µm², or at most 2500 µm². In still other embodiments, the optical source is configured to illuminate a spot on the associated target device with a surface area per spot of from 100 µm² to 250,000 µm², from 225 µm² to 62,500 µm², from 400 µm² to 22,500 µm², from 625 µm² to 10,000 µm², from 900 µm² to 6400 µm², or even from 1600 µm² to 3600 µm².

In some system embodiments, the optical source is configured to illuminate a spot on the associated target device with a power of at least 1 mW, at least 2 mW, at least 3 mW, at least 5 mW, at least 10 mW, at least 20 mW, at least 30 mW, at least 50 mW, or at least 100 mW per spot.

In some system embodiments, the optical source emits a plurality of light beams. The separate light beams are preferably arranged to illuminate a corresponding plurality of optical input couplers on the associated target device. Separating the optical energy into multiple beams can be advantageous in decreasing the input energy per beam and thus decreasing the requirement to dissipate heat energy on the target device. In some embodiments, the optical source emits at least four light beams. In specific embodiments, the optical source emits at least eight light beams or even at least twelve light beams.

In some embodiments, the optical source emits at least one sample excitation beam and at least one alignment beam. As will be described in more detail below, the sample excitation beam is directed through free space to an input coupler on the target waveguide device and from there is directed—typically through an array of integrated waveguides—to nanoscale sample wells arrayed on the device. The alignment beam is directed through free space to an alignment feature on the target waveguide device and serves to align the target device and the optical source or to maintain such alignment, as will be described in further detail below. In specific embodiments, the alignment beam is of a lower output power than the sample excitation beam. In some embodiments, the alignment beam has no more than 10% of the output power of the sample excitation beam. More specifically, the alignment beam has no more than 5% of the output power of the sample excitation beam or even no more than 1% of the output power of the sample excitation beam.

Accordingly, in some system embodiments, the target device comprises an alignment feature, and the optical system further comprises an alignment detector. The combination of an alignment feature on the target device and an alignment light beam and alignment detector within the system is particularly useful in systems where the target device is designed to be removable. In such a system, when a new target device is installed into the system, the alignment feature or features on the target device can be used by the alignment detector to adjust the position of the target device relative to other components of the system, particularly with respect to the optical source, and can thus optimize the coupling of optical energy from the optical source to the target device.

For example, in systems where the optical source emits multiple optical beams, such as in some of the integrated optical delivery devices described in co-owned U.S. Patent Application No. 62/133,965, filed on Mar. 16, 2015, and U.S. patent application Ser. No. 15/072,146, filed on Mar. 16, 2016, the disclosures of which are incorporated by reference herein in their entireties, it can be difficult to achieve optimal alignment of the multiple beams with the multiple input couplers of a target device and to maintain that alignment during the course of a measurement. The alignment beams and associated alignment features of the instant systems overcome those difficulties both by facilitating the initial alignment of the optical source and the target device within the optical system and by maintaining that alignment during the course of an analytical assay.

In particular, the process of aligning an optical source with the target device can include a coarse alignment process, a fine alignment process, or both coarse and fine alignment processes. During the alignment process, the target waveguide device itself can be moved relative to the optical source, the optical source can be moved relative to the target waveguide device, or both devices can be moved relative to one another. In preferred system embodiments, the alignment detector provides for the dynamic alignment of the integrated target waveguide device and the optical source, such that alignment between the components is maintained during an assay. In some system embodiments, the alignment detector is a camera.

As was described in U.S. Patent Application No. 62/133,965 and Ser. No. 15/072,146, the optical source of the instant systems can provide a modulated optical signal. In specific embodiments, the modulated optical signal can be amplitude modulated, phase modulated, frequency modulated, or a combination of such modulations.

In certain embodiments, the optical source of the instant optical systems is one or more lasers, including vertical-cavity surface-emitting lasers, one or more light-emitting diodes, or one or more other comparable optical devices. In specific embodiments, the optical source is one or more lasers.

As already noted, in the analysis of genomic sequence information, it can be advantageous for the target devices of the instant optical analytical systems to include arrays with large numbers of nanoscale sample wells. In order to achieve such scale, the arrays can be fabricated at ultra-high density, providing anywhere from 1000 nanowells per cm², to 10,000,000 nanowells per cm², or even higher density. Thus, at any given time, it can be desirable to analyze the reactions occurring in 100, 1000, 3000, 5000, 10,000, 20,000, 50,000, 100,000, 1 Million, 5 Million, 10 Million, or even more nanowells or other sample regions within a single analytical system, and preferably on a single suitable substrate.

In order to achieve the ultra-high density of nanowells necessary for such arrays, the dimensions of each nanowell must be relatively small. For example, the length and width of each nanowell is typically in the range of from 50 nm to 600 nm, ideally in the range of from 100 nm to 300 nm. It should be understood that smaller dimensions allow the use of smaller volumes of reagents and can, in some cases, help to minimize background signals from reagents outside the reaction zone and/or outside the illumination volume. Accordingly, in some embodiments, the depth of the nanowell can be in the range of 50 nm to 600 nm, more ideally in the range of 100 nm to 500 nm, or even more ideally in the range of 150 to 300 nm.

It should also be understood that the shape of a nanowell will be chosen according to the desired properties and methods of fabrication. For example, the shape of the nanowell can be circular, elliptical, square, rectangular, or any other desired shape. Furthermore, the walls of the nanowell can be fabricated to be vertical, or the walls of the nanowell can be fabricated to slope inward or outward if so desired. In the case of a circular nanowell, an inward or outward slope would result in, for example, a cone-shaped or inverted cone-shaped nanowell.

Using the foregoing systems, simultaneous targeted illumination of thousands, tens of thousands, hundreds of thousands, millions, or even tens of millions of nanowells in an array is possible. As the desire for multiplex increases, and as the density of nanowells on an array accordingly increases, the ability to provide targeted illumination of such arrays also increases in difficulty, as issues of nanowell cross-talk (signals from neighboring nanowells contaminating each other as they exit the array), decreased signal:noise ratios and increased requirements for dissipation of thermal energy at higher levels of denser illumination, and the like, increase. The target waveguide devices and optical analytical systems of the instant specification address some of these issues by providing improved illumination of the waveguides optically coupled to the arrayed nanowells.

Accordingly, the instant disclosure provides optical analytical systems comprising an optical source, such as a laser or another suitable optical source, and an integrated target waveguide device, such as a multiplexed integrated DNA sequencing chip, where the optical source and the target device are optically coupled to one another.

In some system embodiments, particularly where, as described below, the target waveguide device comprises a heat spreading layer, the instant optical analytical systems further comprise a heat sink, wherein the heat sink is in thermal contact with the heat spreading layer of the target device. The heat sink thus receives thermal energy from the heat spreading layer and thereby prevents the optical couplers on the target device from overheating. Such a heat sink may optionally contain fins or the like, in order to maximize surface area and thus heat exchange with the surrounding environment. The heat sink may alternatively, or in addition, contain a refrigerant, or other appropriate liquid, to further improve the efficiency and heat capacity of the device. The heat sink may optionally still further include a fan or other such circulating device for still further improvement of thermal transfer.

Target Waveguide Devices

As mentioned above, the optical analytical systems of the instant specification comprise a target device that, in some embodiments, comprises a plurality of integrated optical waveguides to deliver excitation energy to an array of samples within the device. The use of integrated optical waveguides to deliver excitation illumination is advantageous for numerous reasons. For example, because the illumination light is applied in a spatially focused manner, e.g., confined in at least one lateral and one orthogonal dimension, using efficient optical systems, e.g., fiber optics, waveguides, multilayer dielectric stacks (e.g., dielectric reflectors), etc., the approach provides an efficient use of illumination (e.g., laser) power. For example, illumination of a device comprising an array of nanowells using waveguide arrays as described herein can reduce the illumination power ~10- to 1000-fold as compared to illumination of the same substrate using a free space illumination scheme comprising, for example, separate illumination (e.g., via laser beams) of each reaction site. In general, the higher the multiplex (i.e., the more surface regions to be illuminated on the substrate), the greater the potential energy savings offered by waveguide illumination. In addition, if the optical energy, for example from a laser source, is efficiently coupled into the optical analytical system, waveguide illumination need not pass through a free space optical train prior to reaching the surface region to be illuminated, and the illumination power can be further reduced.

In addition, because illumination of samples is provided from within the confined regions of the target device itself (e.g., optical waveguides), issues of illumination of background or non-relevant regions, e.g., illumination of non-relevant materials in solutions, autofluorescence of substrates, and/or other materials, reflection of illumination radiation, etc., are substantially reduced.

In addition to mitigating autofluorescence of substrate materials within a target device, the coupling of excitation illumination to integrated waveguides can substantially mitigate autofluorescence associated with an optical train. In particular, in typical fluorescence spectroscopy, excitation light is directed at a reaction of interest through at least a portion of the same optical train used to collect signal fluorescence, e.g., the objective and other optical train components. As such, autofluorescence of such components will contribute to the detected fluorescence level and can provide signal noise in the overall detection. Because the systems provided herein typically direct excitation light into the device through a different path, e.g., through a grating coupler, or the like, optically connected to the waveguide in the target device, this source of autofluorescence is eliminated.

Waveguide-mediated illumination is also advantageous with respect to alignment of illumination light with surface regions to be illuminated. In particular, substrate-based analytical systems, and particularly those that rely upon fluorescent or fluorogenic signals for the monitoring of reactions, typically employ illumination schemes whereby each analyte region must be illuminated by optical energy of an appropriate wavelength, e.g., excitation illumination. While bathing or flooding the substrate with excitation illumination serves to illuminate large numbers of discrete regions, such illumination may suffer from the myriad complications described above. To address those issues, targeted excitation illumination can serve to selectively direct separate beams of excitation illumination to individual reaction regions or groups of reaction regions, e.g. using waveguide arrays. When a plurality, e.g., hundreds, thousands, millions or tens of millions, of analyte regions are disposed upon a substrate, alignment of a separate illumination beam with each analyte region becomes technically more challenging and the risk of misalignment of the beams and analyte regions increases. Alignment of the illumination sources and analyte regions can be built into the system, however, by integration of the illumination pattern and reaction regions into the same component of the system, e.g., a target waveguide device. In some cases, optical waveguides are fabricated into a substrate at defined regions of the substrate, and analyte regions are disposed upon the area(s) of the device occupied by the waveguides.

Finally, in some aspects, substrates used in the target waveguide devices are provided from rugged materials, e.g., silicon, glass, quartz or polymeric or inorganic materials that have demonstrated longevity in harsh environments, e.g., extremes of cold, heat, chemical compositions, e.g., high salt, acidic or basic environments, vacuum, and zero gravity. As such, they provide rugged capabilities for a wide range of applications.

Waveguide devices used in the analytical systems of the present specification generally include a matrix, e.g., a silica-based matrix, such as silicon, glass, quartz or the like, polymeric matrix, ceramic matrix, or other solid organic or inorganic material conventionally employed in the fabrication of waveguide substrates, and one or more waveguides disposed upon or within the matrix, where the waveguides are configured to be optically coupled through free space to an optical energy source, e.g., a laser, optionally through an intervening optical fiber, a PLC, one or more lenses, prisms, mirrors, or the like. Waveguides of the instant integrated devices can be in various conformations, including but not limited to planar waveguides and channel waveguides. Some preferred embodiments of the waveguides comprise an array of two or more waveguides, e.g., discrete channel waveguides, and such waveguides are also referred to herein as waveguide arrays. Further, channel waveguides can have different cross-sectional dimensions and shapes, e.g., rectangular, circular, oval, lobed, and the like; and in certain embodiments, different conformations of waveguides, e.g., channel and/or planar, can be present in a single waveguide device.

In typical embodiments, a waveguide in a target waveguide device comprises an optical core and a waveguide cladding adjacent to the optical core, where the optical core has a refractive index sufficiently higher than the refractive index of the waveguide cladding to promote containment and propagation of optical energy through the core. In general, the waveguide cladding refers to a portion of the substrate that is adjacent to and partially, substantially, or completely surrounds the optical core. The waveguide cladding layer can extend throughout the matrix, or the matrix can comprise further "non-cladding" layers. A "substrate-enclosed" waveguide or region thereof is entirely surrounded by a non-cladding layer of matrix; a "surface-exposed" waveguide or region thereof has at least a portion of the waveguide cladding exposed on a surface of the substrate; and a "core-exposed" waveguide or region thereof has at least a portion of the core exposed on a surface of the substrate. Further, a waveguide array can comprise discrete waveguides in various conformations, including but not limited to, parallel, perpendicular, convergent, divergent, entirely separate, branched, end-joined, serpentine, and combinations thereof. In general, a waveguide that is "disposed on" a substrate in one of the instant devices, for example, a target waveguide device, can include any of the above configurations or combinations thereof.

A surface or surface region of a waveguide device is generally a portion of the device in contact with the space surrounding the device, and such space can be fluid-filled, e.g., an analytical reaction mixture containing various reaction components. In certain preferred embodiments, substrate surfaces are provided in apertures that descend into the substrate, and optionally into the waveguide cladding and/or the optical core. As discussed above, in certain specific embodiments, such apertures are very small, e.g., having dimensions on the micrometer or nanometer scale.

The waveguides of the subject target devices provide illumination via an evanescent field produced by the escape of optical energy from the optical core. The evanescent field is the optical energy field that decays exponentially as a function of distance from the waveguide surface when optical energy passes through the waveguide. As such, in order for an analyte of interest to be illuminated by the waveguide, it must be disposed near enough to the optical core to be exposed to the evanescent field. In preferred embodiments, such analytes are immobilized, directly or indirectly, on a surface of the target waveguide device. For example, immobilization can take place on a surface-exposed waveguide, or within a nanowell etched in the surface of the device. In some preferred aspects, the nanowells extend through the device to bring the analyte regions closer to the optical core. Such nanowells can extend through a waveguide cladding surrounding the optical core, or can extend into the core of the waveguide itself. Examples of using optical waveguides to illuminate analytical samples in nanoscale reaction volumes are provided in U.S. Pat. No. 7,820,983 and U.S. Patent Application Publication No. 2012/0085894, which are incorporated by reference herein in their entirety.

Target Waveguide Devices with Low Numerical Aperture

Because the target waveguide devices of the instant disclosure are designed to be removable from an optical analytical system, and because the tolerances between an optical source and its associated target waveguide device must therefore be relatively relaxed, the optical input, or inputs, of the instant integrated target waveguide devices are configured to receive an optical signal, or signals, through free space from an optical source. In particular, the optical couplers of the instant target devices are configured for coupling from the optical source through free space at a distance of at least 1 mm, at least 2 mm, at least 3 mm, at least 5 mm, at least 10 mm, at least 20 mm, at least 30 mm, at least 50 mm, at least 100 mm, or even longer distances. In some embodiments, the devices are configured for optical coupling from the optical source through free space at a distance of at least 5 mm. More specifically, the coupling can be at a distance of at least 10 mm. Even more specifically, the coupling can be at a distance of at least 20 mm.

The instant devices can be configured to receive optical energy through free space in a variety of ways. In particular, the dimensions, shape, orientation, composition, and other properties of the optical components of the devices are chosen to provide such optical coupling through free space, as described in more detail below and in the Examples section. In some embodiments, the optical couplers of the target device are diffractive grating couplers, although other optical couplers, such as endfire couplings, prism couplings, or any other suitable optical input, can be usefully coupled to the integrated waveguides in the instant devices. Furthermore, the instant target waveguide devices preferably have multiple optical inputs, so that the optical energy is coupled into multiple independent waveguide pathways arrayed within the device.

These and other features distinguish the instant devices and systems from those typically used for optical transmission and coupling in telecommunications and other related applications, where optical sources are typically coupled to their targets through extremely short distances. Indeed, the distances typically coupled in an integrated telecommunications optical device are on the order of 10 µm or even less. For example, U.S. Patent Application Publication No. 2014/0177995 discloses devices for optical coupling from an integrated device to an external optical fiber, where the outputs include couplers that comprise an integrated waveguide structure, a mirror structure, and a tapered vertical waveguide, where the vertical waveguide has apertures in the range of 0.1 to 10 µm and typical heights of 5-30 µm. These couplers, also known as vertical spot size converters, are designed for direct or nearly direct connection between the integrated waveguide structure and an associated output fiber. The devices optionally include a microlens of diameter less than 1 mm fabricated within the vertical waveguide. Another example of the direct, or nearly direct, coupling between an integrated waveguide device and an associated target optical fiber is provided in U.S. Patent Application Publication No. 2015/0001175, which discloses the use of cylinder-shaped or sphere-shaped microlenses to facilitate optical coupling. The lenses are fabricated with radii roughly the same as the ~10 µm mode size of a typical telecommunications optical fiber, where the fiber is directly abutted with the microlens. These couplers are thus also designed for direct or nearly direct connection between the integrated waveguide structure and the target fiber at the time of device manufacture.

The target devices of the instant disclosure thus comprise an optical coupler and an integrated waveguide that is optically coupled to the optical coupler. In some embodiments, the optical coupler of the instant devices is a low numerical aperture coupler, and in some embodiments, the optical coupler is a diffraction grating coupler.

Grating couplers and their use in coupling light, typically light from optical fibers, to waveguide devices are known in the art. For example, U.S. Pat. No. 3,674,335 discloses reflection and transmission grating couplers suitable for routing light into a thin film waveguide. In addition, U.S. Pat. No. 7,245,803 discloses improved grating couplers comprising a plurality of elongate scattering elements. The couplers preferably have a flared structure with a narrow end and a wide end. The structures are said to provide enhanced efficiency in coupling optical signals in and out of planar waveguide structures. U.S. Pat. No. 7,194,166 discloses waveguide grating couplers suitable for coupling wavelength division multiplexed light to and from single mode and multimode optical fibers. The disclosed devices include a group of waveguide grating couplers disposed on a surface that are all illuminated by a spot of light from the fiber. At least one grating coupler within the group of couplers is tuned to each channel in the light beam, and the group of couplers thus demultiplexes the channels propagating in the fiber. Additional examples of grating couplers are disclosed in U.S. Pat. No. 7,792,402 and PCT International Publication Nos. WO 2011/126718 and WO 2013/037900. A combination of prism coupling and grating coupling of a multi-wavelength optical source into an integrated waveguide device is disclosed in U.S. Pat. No. 7,058,261.

FIGS. 1A-1C provide a general comparison between target waveguide devices that are coupled directly, or nearly directly, to an optical source with a high numerical aperture, and those, as disclosed herein, where coupling is through free space to an optical source with a low numerical aperture. As shown in FIG. 1A, where light is coupled from an optical fiber (100) or other optical source with high numerical aperture to a target waveguide device (110), the optical beam (102) travels a relatively short distance and thus displays a relatively small beam radius. As shown, the optical beam illuminates a grating coupler (106) that is optically connected to an integrated waveguide (108) within the target device. For comparison, as shown in FIG. 1B, the target waveguide devices of the instant disclosure (e.g., 160) are illuminated by an optical beam (152) that travels a longer distance from the optical source (150) and displays a larger beam radius than the system shown in FIG. 1A. The larger beam, after optionally passing through a lens element (154) or the like, illuminates a relatively larger grating coupler (156) and is then launched into the optically coupled integrated waveguide (158) associated with the coupler.

FIG. 1C illustrates an alternative embodiment of this type of optical system. Specifically, in this system, one or more optical elements (e.g., 184) are positioned between an optical source (e.g., 180) and a target waveguide device (e.g., 190). Such optical elements can serve to focus, collimate, or otherwise modify an optical beam (e.g., 182) before it illuminates the target waveguide device. The optical element can, for example, modulate the focus of the beam to more closely match the numerical aperture (NA) of the grating coupler (e.g., 186) on the target device, as would be understood by those of ordinary skill in the art. The optical element can likewise, for example, modulate the size of the footprint of the beam on the grating coupler, as desired. As should be understood from this example, the NA of the optical output of the optical source need not exactly match the NA of the input coupler on the target device, since an intervening lens or other optical element can be used to modulate the optical properties of the beam between the optical source and the target waveguide device.

In one aspect, the instant disclosure therefore provides target waveguide devices with one or more optical inputs that are configured to couple light through free space from an optical source or sources. The optical source can be delivered to the target device through an intermediate optical component, for example through a PLC or the like, such as the PLCs disclosed in co-owned U.S. Patent Application No. 62/133,965 and Ser. No. 15/072,146. According to some embodiments, the numerical aperture (NA) of the optical inputs in the target waveguide devices is modulated in order to facilitate and optimize coupling into the target device in various ways. As is understood by those of ordinary skill in the optical arts, NA is related to the range of angles within which light, in particular a light source approximating a Gaussian light beam, can be accepted or emitted from a lens, a fiber, a waveguide, a grating coupler, or the like. It is a dimensionless value that, in the case of a Gaussian beam impinging on an objective lens, can be calculated using the following equation:

$$NA = n \sin \theta_{max}$$

where n is the index of refraction of the medium through which the beam is propagated and $\theta_{max}$ is the maximum acceptance angle of the lens. This angle corresponds to the half-angle of the lens's acceptance cone, i.e., the cone of light capable of entering or exiting the lens.

In the case of a multi-mode optical fiber, the numerical aperture depends on $n_{core}$, the refractive index of the core, and $n_{clad}$, the refractive index of the cladding, according to the following equation:

$$NA = \sqrt{n_{core}^2 - n_{clad}^2}$$

The NA of an optical device, such as a fiber or an integrated waveguide, thus can depend on the optical properties of the materials used to fabricate the device (e.g., the core and the cladding of a fiber or waveguide) and the size and geometry of the device. The NA also depends on the wavelength of light being propagated through the device. It should thus be understood that the NA of a particular optical device can be usefully modulated to obtain suitable behavior of the device for a particular application and purpose.

From a practical standpoint, the NA of a given optical device can also be determined empirically, for example by measuring the characteristics of propagated light emitted by the device at a certain distance from the end of the device, for example using a direct far field scanner according to specification EIA/TIA-455-47. Such measurements provide empirical values of the mode field diameter (MFD), effective area, and numerical aperture of the optical device. In the case of a single-mode fiber, the MFD is related to the spot size of the fundamental mode and represents a far-field power distribution of the optical output of the fiber. The relationship between NA and MFD for a Gaussian beam is provided by the following equation, where $\lambda$ is the wavelength of propagated light:

$$MFD = \frac{2}{\pi} \times \frac{\lambda}{NA}$$

Table 1 shows the relationship between NA and beam diameter for light of 532 nm, where the Gaussian beam profile is truncated at three different power levels: $1/e^2$, $1/e^3$, and $1/e^4$. The listed beam diameters at a power truncation of $1/e^2$ correspond to the MFD of the beam for each value of NA. The listed beam diameters at a power truncation of $1/e^3$ provide a useful estimation in designing the size of an optical coupler on a target device. More specifically, a coupler of the cross-sectional size shown in this column will capture most of the energy from the transmitted beam.

Figure 2A:
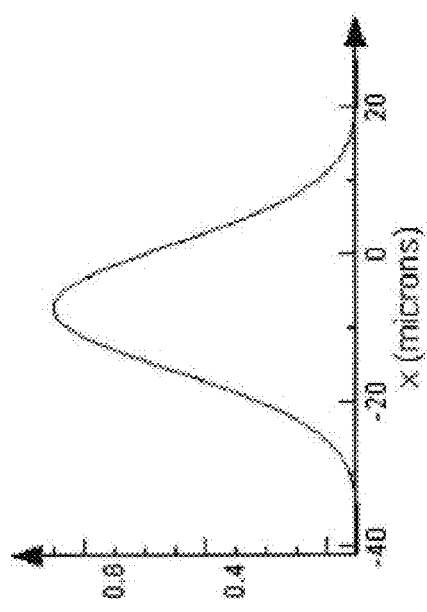
FIG. 2A shows a plot of the intensity of a Gaussian beam as a function of distance from the beam axis.

As is known in the art, single mode fiber devices are commonly used in a variety of optical devices for the transmission and coupling of optical signals, particularly in the telecommunications industry. Such devices typically display NA values of 0.12 or greater. As shown in Table 1, such NAs, for example NAs of 0.12 and 0.13, result in relatively narrow beam sizes at this wavelength of light: 2.82 µm and 2.61 µm, respectively. By comparison, a Gaussian beam of 532 nm light with an NA of 0.01 displays a beam size of approximately 34 µm—over 10 times larger. FIG. 2A shows the 2-dimensional profile of such a Gaussian beam (NA equal to 0.01). As just noted, the beam size is determined by the truncation of beam profile at the $1/e^2$ power level.

TABLE 1

Power-truncated beam profiles for light of 532 nm as a function of NA.

| NA | $1/e^2$ (µm) | $1/e^3$ (µm) | $1/e^4$ (µm) |
|---|---|---|---|
| 0.13 | 2.61 | 3.91 | 5.21 |
| 0.12 | 2.82 | 4.23 | 5.64 |
| 0.05 | 6.77 | 10.16 | 13.55 |
| 0.015 | 22.58 | 33.87 | 45.16 |
| 0.01 | 33.87 | 50.80 | 67.74 |
| 0.005 | 67.74 | 101.60 | 135.47 |

It should also be understood that the diameter of a Gaussian beam will vary along the beam axis due to beam divergence. More specifically, for a divergent Gaussian beam propagated in free space, the beam radius, w, varies as a function of distance, z, along the length of the beam axis according to the equation:

$$w(z) = w_0 \sqrt{1 + \left(\frac{z}{z_R}\right)^2}$$

where $w_0$ is the minimum beam radius, i.e., the "waist radius", that occurs at a particular location along the beam axis known as the "beam waist", z is the distance from the beam waist along the beam axis, and $Z_R$ is the Rayleigh length, a constant for a given beam that depends on the waist radius and the wavelength of light, λ, according to:

$$z_R = \frac{\pi w_0^2}{\lambda}$$

Accordingly, at a distance along the beam axis of $z_R$ from the beam waist, the beam radius is equal to $w_0\sqrt{2}$. In view of the above, it also follows that the Rayleigh length and the numerical aperture are related to one another according to the following equation:

$$NA = \frac{w_0}{z_R}$$

Figure 2B:
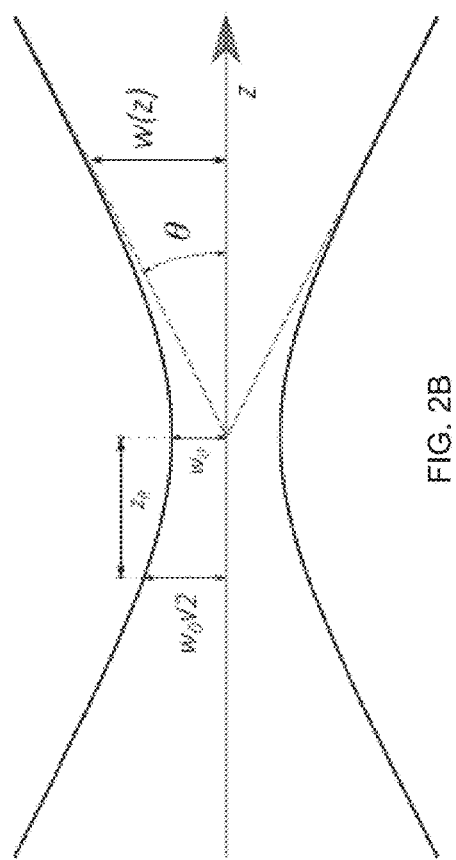
FIG. 2B illustrates the shape of a divergent Gaussian beam of radius w(z).

The above parameters are illustrated graphically in FIG. 2B, which represents a divergent Gaussian beam of radius w.

In accordance with the above description, lenses, fibers, and waveguides with relatively large NA values are typically used to illuminate target surfaces over short distances through free space, and the spot size of such illumination is typically small. These distinctions are apparent in the exemplary systems illustrated graphically in FIGS. 1A and 1B. Specifically, the optical device (100) of the system shown in FIG. 1A (e.g., an optical fiber) has a high NA, and is best suited for illuminating a small-diameter coupler at close proximity to the target waveguide device (110). By comparison, the optical source (150) and lens (154) of the system shown in FIG. 1B has a low NA, and, as described herein, is well suited for illuminating a large-diameter coupler at a large free-space coupling distance. As mentioned above, FIG. 1C shows an alternative design that permits the optical footprint of the output beam to be re-imaged with a target magnification, for example using an intervening optical element, to provide a beam waist of a preferred size at the surface of the target device. It should be further noted here that the illustrations provided throughout the disclosure are not necessarily intended to represent accurately the dimensions, angles, or other specific design features of the devices illustrated, in particular any representation of divergence angles, beam radii, layer thicknesses, waveguide bend radii, specific routing paths, and so forth.

Free-space coupling, as disclosed in the devices and systems herein, provides several advantages relative to the direct, or nearly direct, coupling typically used in telecommunications and related systems. First, coupling through free space avoids near-surface fiber tip to chip operation and is thus much easier for installation and operation and much less vulnerable to chip-surface dust and contamination and tip damage due to mis-operation of optical analytical systems with removable target waveguide devices. Second, as illustrated in FIGS. 1B and 1C, coupling with low NA delivery devices through free space allows larger beam diameters on the target waveguide device, thus relieving thermal constraints on the target chip due to the injection of high laser power. Third, larger grating coupler size also greatly alleviates optical source-to-chip alignment difficulties and minimizes the impact of dust and other contaminants on the coupler surface. Fourth, free-space coupling allows easier chip packaging solutions for the target chip, which, for example in a multiplexed DNA sequencing chip, needs to accommodate all the packaging interface requirements such as electrical, thermal, mechanical, and fluidics components. Use of larger couplers is particularly advantageous in applications where surface-area constraints are not of overriding importance, for example in some applications using commercial CMOS chips. In view of the above, it should be apparent that the input NA of the instant target waveguide devices can thus be modulated in order to improve and optimize optical coupling from an associated optical source.

Accordingly, the instant disclosure provides target waveguide devices with one or more optical inputs that are configured to couple light through free space from an optical source or sources through a high-efficiency input coupler. Such devices can optionally comprise additional features, for example further integrated waveguides, preferably in an array, and a plurality of nanowells optically coupled to the waveguide or array of waveguides. As described above, an array of nanowells in optical connection with an excitation source can be usefully employed, for example, in the performance of highly-multiplexed DNA sequencing reactions using fluorescently-labeled nucleotide reagents.

Figure 3A:
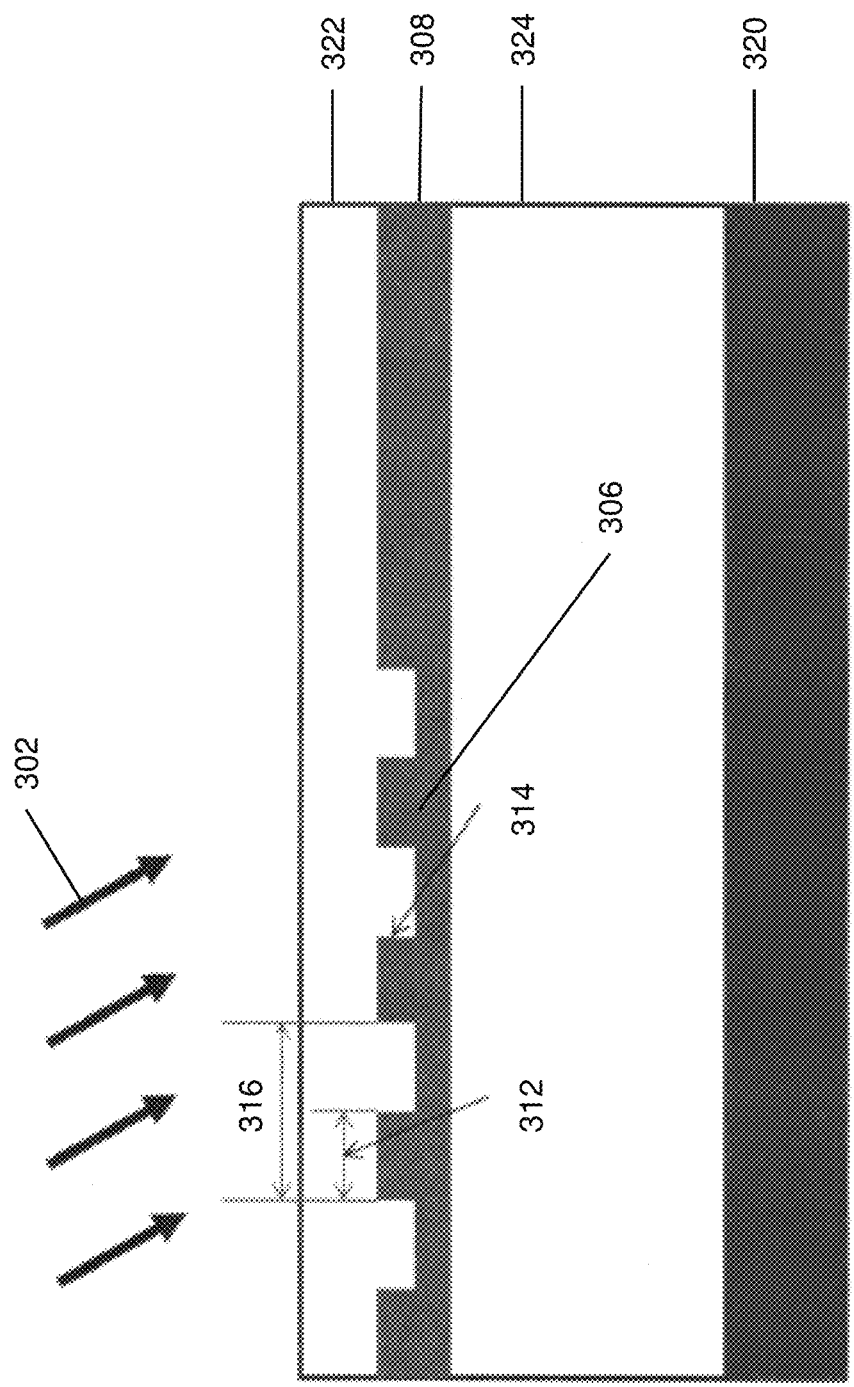
FIG. 3A shows the basic design features and structure of a standard grating coupler.
Figure 3B:
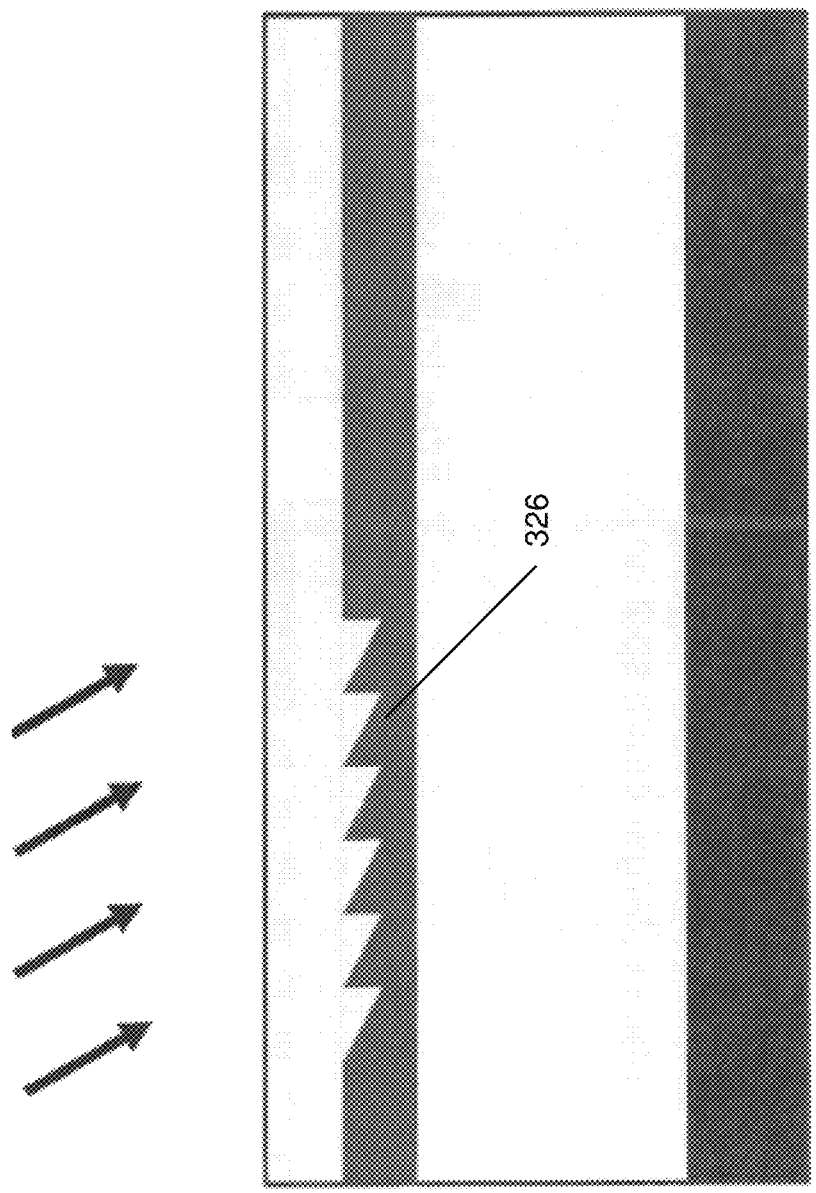
FIG. 3B shows the same for a blazed grating coupler.

The free-space coupling of optical energy into the instant target devices is preferably achieved through the use of a high-efficiency, low-NA grating coupler. An exemplary grating coupler is illustrated in FIG. 3A. Such couplers are conveniently prepared using standard semiconductor processing techniques on, for example, a silicon chip or other suitable substrate (320). The grating typically includes a bottom cladding layer (324), a waveguide core layer (308), and a top cladding layer (322), where the core layer has a higher refractive index than the cladding layers, so that light injected into the core is propagated by total internal reflection at the core/cladding boundaries. A grating structure (306) is created in the waveguide core, typically during the fabrication process, with a desired duty cycle (312), etch depth (314), and grating period (316), such that optical energy (302) incident on the surface of the grating can enter the grating and be efficiently propagated down the waveguide core. FIG. 3B shows a variant of the grating coupler of FIG. 3A, where the waveguide core is etched as shown to provide a "blazed" coupler region (326).

Figure 3C:
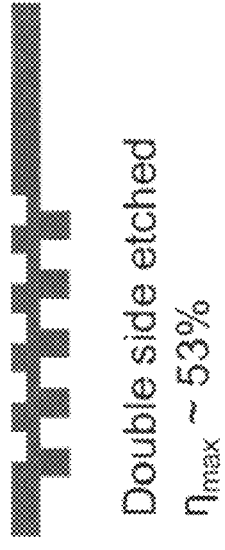
Figure 3D:
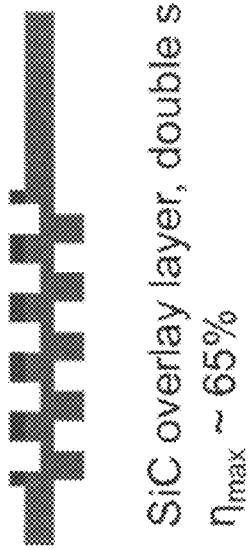
Figure 3E:
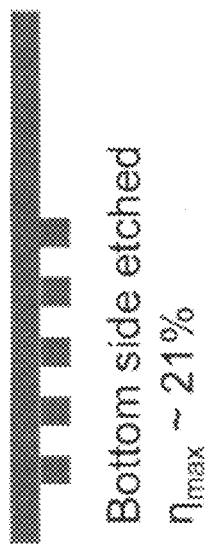
Figure 3F:
Figure 3G:
Figure 3H:

The detailed grating coupler structures and shapes can be varied in a number of ways to improve the coupling efficiency. For a simple binary grating coupler, the structure can be etched from the top only, as illustrated in FIGS. 3A, 3B, and 3E, or from the bottom only, as illustrated in FIG. 3C. Alternatively, the structure can be double-sided etched from both the top and the bottom, as illustrated in FIGS. 3D and 3F. Moreover, an overlay layer can be added to the structure to the increase the teeth height, as illustrated in the grating coupler structures of FIGS. 3E and 3F, thus further improving the coupling efficiencies of the gratings. The period of the grating coupler can be fixed as a uniform grating, or it can be "chirped" with a certain function, by fabricating the teeth with a non-uniform period, to better match the Gaussian beam profile, as illustrated in the grating coupler (346) illustrated in FIG. 3G, thus improving the coupling efficiency. Alternatively, or in addition, a bottom reflective layer (370) can be added to the structure, as illustrated in FIG. 3H, to reflect the down-coupling light and thus to improve coupling efficiency.

In some embodiments, the grating period of the instant grating couplers is in the range from 300 nm to 1000 nm. In more specific embodiments, the grating period is in the range from 300 nm to 500 nm and from 300 nm to 400 nm. In even more specific embodiments, the grating period is from 340 nm to 380 nm and can in some embodiments be approximately 355 nm. In other even more specific embodiments, the grating period is from 300 nm to 340 nm and can in some embodiments be approximately 315 nm.

In some embodiments, the etch width of the instant grating couplers is in the range from 150 nm to 500 nm. In more specific embodiments, the etch width is in the range from 150 nm to 400 nm. In even more specific embodiments, the etch width is in the range from 150 nm to 300 nm and can in some embodiments be approximately 185 nm.

In embodiments, the etch depth of the instant grating couplers is in the range from 30 nm to 200 nm, is in the range from 50 nm to 150 nm, or is in the range from 50 nm to 100 nm. Specifically, the etch depth can be approximately 68 nm.

In some embodiments, the etch depth is in the range from 30 nm to 80 nm. Specifically, the etch depth can be approximately 55 nm.

The thickness of the waveguide core of the instant grating couplers is preferably optimized for single-mode operation using light of a desired wavelength. The optimal core thickness ("d") can accordingly be estimated using the following relationship:

$$V = \frac{\pi d}{\lambda}\sqrt{n_{core}^2 - n_{clad}^2} < \frac{\pi}{2} \Rightarrow d < \frac{\lambda}{2} \cdot \frac{1}{\sqrt{n_{core}^2 - n_{clad}^2}}$$

For a typical waveguide construction, with a silicon nitride core (e.g., $n_{core} \approx 1.9085$) and a silicon dioxide cladding (e.g., $n_{clad} \approx 1.46$), a core thickness of about 217 nm is optimal for light with wavelength of 532 nm, and a core thickness of about 225 nm is optimal for light with wavelength of 552 nm. Where the refractive index of the waveguide core is increased, for example by using a titanium oxide core, or the like, optimal core thicknesses can be significantly smaller. For example, where $n_{core}=2.55$ and $n_{clad}=1.46$, optimal core thicknesses of 127 nm (@532 nm) and 132 nm (@552 nm) can be estimated. In view of the above, the waveguide core thickness of the instant grating couplers can range from about 100 nm to about 300 nm. More specifically, the waveguide core thickness can range from about 100 nm to about 150 nm, and even more specifically from about 125 nm to about 135 nm. In some embodiments, the waveguide core thickness can range from about 150 nm to about 250 nm, more specifically from about 200 nm to about 240 nm, and even more specifically from about 215 nm to about 230 nm. In some embodiments, the waveguide core thickness can be approximately 180 nm.

In embodiments, the waveguide core refractive index of the instant grating couplers is in the range from 1.9 to 3.5 and more specifically is approximately 1.9. In some embodiments, the waveguide core refractive index is in the range from about 2.4 to about 2.7, more specifically from about 2.5 to about 2.6. In embodiments, the top cladding thickness of the instant grating couplers is in the range from 250 nm to 1000 nm, more specifically is approximately 280 nm. In embodiments, the bottom cladding thickness of the instant grating couplers is in the range from 2 µm to 10 µm and more specifically is approximately 2.1 µm. In embodiments, the cladding refractive index of the instant grating couplers is in the range from 1 to 2 and is more specifically approximately 1.47. It should be understood that refractive indices are preferably specified for a given material at the wavelength of light being transmitted through the material, as would be understood by those of ordinary skill in the art.

In device embodiments comprising a reflective layer, the reflector distance (from coupler bottom to the reflector) of the devices can be in the range from 250 nm to 500 nm and can be more specifically approximately 260 nm.

As mentioned above, the NA of the instant target waveguide devices can be modulated in order to improve coupling from the optical source through free space. In embodiments, the NA of the target waveguide device is modulated to match the NA of the optical source. According to some embodiments, the optical input of the instant devices has a numerical aperture of no more than 0.1, no more than 0.08, no more than 0.05, no more than 0.03, no more than 0.02, no more than 0.01, no more than 0.005, or even lower. In some embodiments, the numerical aperture is no more than 0.05. In specific embodiments, the numerical aperture is no more than 0.015.

As should be apparent from the comparison shown in FIGS. 1A and 1B, although the NA of traditional optical sources and targets (e.g., 100 and 110) is significantly higher than that of the optical sources and targets used in the instant systems (e.g., 150 and 160), the surface area or "footprint" illuminated on the instant target devices is larger. (For example, compare the size of grating couplers 106 and 156.) As noted above, larger optical footprints can be advantageous inter alia in minimizing heating of the target device and/or in simplifying alignment of the optical source and the target device. In particular, the power intensity of the transmitted light is much lower than it would be if the light were transmitted in a more focused beam.

The exact spot size of light delivered to a target waveguide device will, of course, depend both on the NA of the optical outputs of the optical source and the free space distance between the optical source and the target device. In embodiments, the target waveguide device is designed with a coupler size that matches the spot size of illumination from the optical source. In embodiments, the coupler size of the target device is at least 100 $\mu m^2$, at least 144 $\mu m^2$, at least 225 $\mu m^2$, at least 400 $\mu m^2$, at least 625 $\mu m^2$, at least 900 $\mu m^2$, at least 1600 $\mu m^2$, at least 2500 $\mu m^2$, at least 4900 $\mu m^2$, at least 10,000 $\mu m^2$, or even larger.

In other embodiments, the coupler size of the target device is at most 250,000 $\mu m^2$, at most 62,500 $\mu m^2$, at most 22,500 $\mu m^2$, at most 10,000 $\mu m^2$, at most 6400 $\mu m^2$, at most 3600 $\mu m^2$, or at most 2500 $\mu m^2$.

In specific embodiments, the coupler size of the target device is from 100 $\mu m^2$ to 250,000 $\mu m^2$, from 225 $\mu m^2$ to 62,500 $\mu m^2$, from 400 $\mu m^2$ to 22,500 $\mu m^2$, from 625 $\mu m^2$ to 10,000 $\mu m^2$, from 900 $\mu m^2$ to 6400 $\mu m^2$, or from 1600 $\mu m^2$ to 3600 $\mu m^2$.

In embodiments, the above-described illuminations are achieved at a free-space distance between the optical source and the target device of from 1 mm to 100 mm. More specifically, the free-space distance can be from 2 mm to 90 mm, from 5 mm to 80 mm, from 10 mm to 60 mm, or even from 20 mm to 50 mm.

It also follows from the above description that the instant target waveguide devices are capable of receiving relatively high levels of optical energy from an optical source due to the relatively large spot sizes illuminated on the target device. Accordingly, in embodiments, the target device is configured to receive optical energy with power per coupler of at least 1 mW, at least 2 mW, at least 3 mW, at least 5 mW, at least 10 mW, at least 20 mW, at least 30 mW, at least 50 mW, at least 100 mW, or even higher per coupler. In specific embodiments, these power levels are achieved at a free-space distance of at least 10 mm.

According to another aspect of the disclosure, it can be desirable to modulate the design of the integrated waveguides in the target waveguide device in order to improve the coupling between the optical source and the target waveguide device. In particular, it can be desirable to modulate the composition and shape of the integrated waveguides to achieve these effects. For example, it is known in the field of optics that mismatches between the mode sizes and effective indices between the highly confined mode of an integrated optical waveguide and the large diameter mode of an optical fiber input can result in coupling losses if not addressed. It can therefore be advantageous to taper the waveguide geometry or otherwise vary the waveguide structure and/or composition in order to improve the behavior and efficiency of the device, particularly in transitions between confined and unconfined optical modes. Such variation in structure and composition can include, for example, modulation of cladding composition and geometry or modulation of core composition and geometry. In particular, core cross-sectional geometry can be modulated to improve coupling efficiencies. These and other features can be modeled and tested using widely available commercial software to predict and optimize the photonic properties of the devices prior to their fabrication.

In some applications, it can be advantageous to vary the optical power emitted from each optical output of an optical source according to the specific requirements of the target device, for example to compensate for propagation losses as the light passes through the target waveguides. Such approaches are described in co-owned U.S. Patent Application No. 62/133,965 and Ser. No. 15/072,146. Other advantageous features and designs that can optionally be included in the instant target waveguide devices are disclosed in U.S. Patent Application Publication Nos. 2014/0199016 and 2014/0287964, which are incorporated by reference herein in their entireties.

The waveguide devices and systems of the instant disclosure can be further distinguished from those typically used in transmitting optical signals in telecommunications applications. In particular, the instant target waveguide devices are designed for use with higher intensity optical energy, and they are designed to transmit that energy for much shorter distances. In addition, the wavelengths of light transmitted by these devices are suitable for use with the optically active reagents commonly used in biological assays. These wavelengths are generally significantly shorter than those used for telecommunications purposes. In particular, the optical illumination used in DNA sequencing reactions with fluorescently-labeled DNA reagents, is typically in the visible range, most commonly in the range from 450 nm to 650 nm. The waveguides and other components of the target devices and systems disclosed herein are therefore preferably designed and scaled to transmit optical energy efficiently in the visible range. In some embodiments, the wavelengths range from about 400 nm to about 700 nm. In more specific embodiments, the wavelengths range from about 450 nm to 650 nm or even from about 500 nm to about 600 nm. In some specific embodiments, the wavelengths are from about 520 nm to about 540 nm, for example, approximately 532 nm. In other specific embodiments, the wavelengths are from about 620 nm to about 660 nm, for example, approximately 635 nm or 650 nm. In still other specific embodiments, the devices are designed for optimal transmission of light having wavelengths from about 540 nm to about 560 nm, for example, approximately 552 nm. In some embodiments, multiple wavelengths of visible light can be transmitted within the devices simultaneously. A silicon nitride waveguide device, including an integrated grating coupler, for the transmission of visible wavelengths has recently been reported. Romero-Garcia et al. (2013) *Opt. Express* 21, 14036. Accordingly, in some embodiments, the waveguide core material is a silicon nitride. In other embodiments, the waveguide core material is a material having an even higher refractive index at the wavelengths used in the instant device, for example a titanium oxide, such as titanium dioxide ($TiO_2$). Such higher refractive index materials also preferably display low autofluorescence.

Figure 3I:
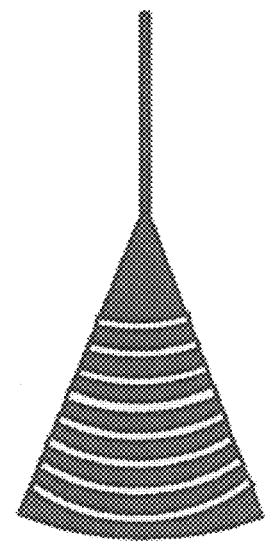

The grating couplers of the instant devices may in some embodiments be beam focusing couplers. In particular, in order to avoid the long taper associated with the reduction of mode size from the large footprint, low-NA grating couplers (where mode size can be, for example, 50 μm) to a mode size effective in illuminating nanoscale sample wells (for example, 0.5 μm), the shape of the coupler can be changed from rectangular (as viewed from the top) to tapered (as viewed from the top) to form an ultracompact focusing grating coupler. The top view of one such exemplary coupler design is illustrated in FIG. 3I.

Beam focusing couplers may bend the grating lines to be a series of confocal ellipses with the focal point located at the grating-waveguide interface. Therefore, the optical mode can be directly focused from the grating to the waveguide in a much smaller distance, in some cases on the order of several hundred microns. As illustrated in FIGS. 3J and 3K, which are also top views of the couplers, the transition region between the grating coupler and the integrated waveguide core can, for example, be a tapered waveguide (FIG. 3J) or a slab waveguide (FIG. 3K). In each case, the curved grating lines focus the light into the aperture of the integrated waveguide. Also identified in these figures are two relevant parameters—focal length and defocus—that are of importance in the design of a beam focusing coupler. Furthermore, as shown with the slab waveguide transition region of FIG. 3K, the aperture of the integrated waveguide targeted by the grating coupler can be tapered to a wider width in order to achieve optimal coupling. FIG. 3L illustrates a cross-sectional profile of an exemplary focusing grating coupler, indicating preferred chemical compositions of the various layers and exemplary dimensions of the various features.

In this regard, for some target waveguide device embodiments, where the coupler is a focusing grating coupler, the focusing coupler focal length can be in the range from 150 μm to 500 μm and can be more specifically approximately 170 μm. In some embodiments, the focusing coupler defocus of the instant grating couplers is in the range from 0 to 10 μm and is more specifically approximately 0 μm. In some embodiments, the focusing coupler aperture width is in the range from 1 μm to 5 μm and is more specifically approximately 3 μm. In some embodiments, the waveguide taper length of the focusing grating couplers is in the range from 50 μm to 200 μm and is more specifically approximately 75 μm. In some embodiments, the coupling angle of the instant grating couplers is in the range of 10 degrees+/−2 degrees. In a specific design, the coupler is a slab coupler with focal length=150 μm, defocus=0, and aperture width=3 μm.

Furthermore, the above design features and parameters of a target waveguide device can be combined, in any suitable way, to maximize the coupling efficiency. The design and fabrication of the above-described structures is within the skill of those of ordinary skill in the art. Exemplary grating couplers are described in the references provided above. Other exemplary waveguide devices with grating couplers, including focusing couplers and couplers with reflective metallic layers, have also been reported. See, e.g., Waldhäusl et al. (1997) *Applied Optics* 36, 9383; van Laere et al. (2007) *J. Lightwave Technol.* 25, 151; van Laere et al. (2007) DOI: 10.1109/OFC.2007.4348869 (Optical Fiber Communication and the National Fiber Optic Engineers Conference); U.S. Pat. No. 7,283,705. It should be understood, however, that the couplers disclosed in these references are typically designed for optimal coupling from high-NA optical sources, not from low-NA optical sources.

Target Waveguide Devices with Alignment Features

In some embodiments, the target devices and systems of the instant disclosure include features that provide free-space coupling between an optical source and a target device while maintaining alignment of the components to sub-micron accuracy in space, including angle tolerances. Disturbances communicated to the analytical system from the mounting such as shocks and vibrations may cause alignment errors that are substantial on the submicron scale. Pneumatic isolation, which has been used in some prior art analytical systems, is physically large, and expensive, in order to reject these perturbations passively. An alternative to such passive approaches is the use of an active rejection by estimation of an alignment error, and commanding a correction, and possibly iterating depending on the particular response of the physical servo system. This active rejection of vibration can be small, inexpensive, and highly effective: however, this active rejection requires an error signal. On the time scales of interest, the image correlation approaches used in some prior art instruments to estimate an error are insufficiently fast. Hill climbing based on a dither (or perturb and observe) require higher bandwidth, more expensive actuators, or are insufficiently fast.

The dynamic alignment approach disclosed herein involves one or more alignment features that can be inexpensively incorporated into a target waveguide device within an optical analytical system. Such alignment features are used in combination with an alignment detector, such as an alignment camera, within the analytical system to provide a continuous estimate of alignment error, thus enabling an inexpensive actuation and detection system.

In some embodiments, the alignment features take the form of additional grating couplers, which may or may not be the same design as the grating couplers used to couple the main pump power into the device. The grating couplers couple input optical signals into associated alignment waveguides. They can be arranged in at least one, often 2, and sometimes more locations to better estimate magnification, roll, and other errors. The alignment structures detect the light from one or more alignment or "outrigger" light beams that are directed toward the target waveguide. The alignment light beams typically emanate from the same optical source as the one or more sample excitation light beams (i.e., the light beams targeting the analytical samples), so that the position of the alignment beams can be used as a proxy for the position of the one or more sample excitation light beams.

The input couplers of the alignment waveguides direct coupled light from designated beams to designated output couplers, which may or may not be grating couplers. These output couplers should be readily distinguishable from one another, so that the output power can be uniquely estimated for each. For example, where a low NA external camera is used as a detector, the spacing can be ~150 μm.

Figure 4A:
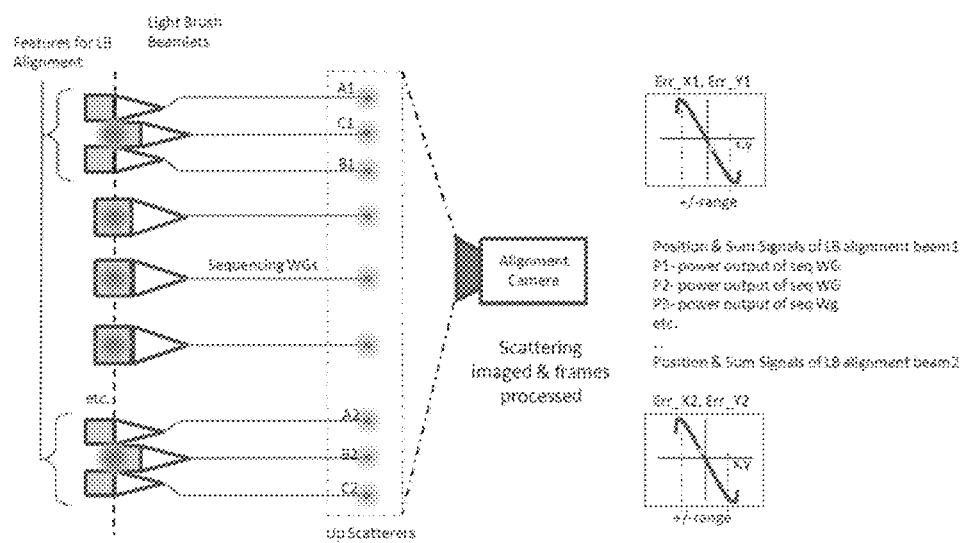
FIG. 4A shows the input coupling region of an exemplary target waveguide device with active waveguide alignment features.

The output estimated for each output device can then be combined, typically with a simple formula, to form what is designated a tracking error signal (TES). This TES, for each dimension of interest, can then be converted into a command to counter the present state of misalignment. An exemplary arrangement of alignment couplers, together with their associated alignment waveguides and output couplers, and sample excitation couplers, together with their associated sample excitation or "sequencing" waveguides, is shown in FIG. 4A. As shown, this exemplary target waveguide device includes two triads of alignment waveguides, shown as the top three coupler/waveguide combinations and the bottom three coupler/waveguide combinations in the drawing. Each triad of alignment couplers is illuminated by a single optical input, illustrated as a circular shaded region in the drawing, so that the portion of light passing through each of the waveguides depends on the alignment of the optical input with each alignment coupler. The output from the alignment waveguides, designated A1, B1, and C1 for the top triad of alignment waveguides and A2, B2, and C2 for the bottom triad of alignment waveguides, is monitored by a camera or other suitable alignment detector device to generate a TES. If the optical source and target device move relative to one another during a measurement, it is apparent that the TES generated by each trio of waveguides will change. Alignment can be maintained, and misalignment can be reversed, by monitoring the TES values. Each triad of alignment input and output couplers and their associated alignment waveguides should be considered a single alignment feature for purposes of this disclosure.

Also shown in the device of FIG. 4A are sample excitation couplers, in this case fabricated between the two triads of alignment couplers. The sample excitation couplers are used to deliver optical energy from the input beams, which are identified in FIG. 4A as circular shaded regions within each coupler, to the analytical nanoscale samples within the device, typically through a fanout region of the device. The fanout region splits the incoming excitation signal into a larger number of split waveguides for delivery to the arrays of nanoscale sample wells in the device. One or more of the sample excitation waveguides associated with each input coupler can additionally be used to monitor power levels of optical energy input into the sample excitation input coupler. These power monitoring waveguides can deliver their optical signals to an output coupler for monitoring by a power output detector. In some embodiments, for example as shown in the device of FIG. 4A, the power output monitoring couplers, identified as circular shaded regions at the end of the "sequencing WGs" in FIG. 4A, are located near the alignment waveguide output couplers. In these embodiments, a single detector, for example a single camera, can be used to monitor both the alignment waveguide signals and the sample excitation waveguide power output monitoring signals simultaneously.

Figure 4B:
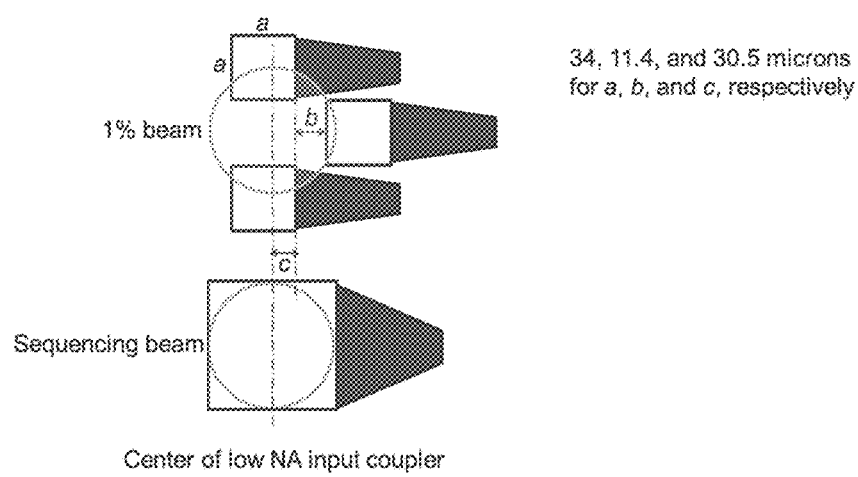
FIG. 4B shows in closer detail the two types of input couplers used in the waveguide device of FIG. 4A.

The input couplers of the alignment waveguides and the input coupler of a sample excitation waveguide (labeled as a "low NA input coupler") are shown in closer detail in FIG. 4B. The optical input for the alignment feature in this exemplary device is a 1% beam, that is, the alignment beam carries about 1% of the power of all of the combined beams reaching the device. The optical input for the sample excitation coupler is a full-power beam, also known as a "sequencing beam" or a "pump-power beam". The footprints illuminated by these beams are illustrated as shaded circles in FIG. 4A and as open circles in FIG. 4B. Approximate dimensions of the exemplary input couplers are also shown in FIG. 4B.

Figure 4C:
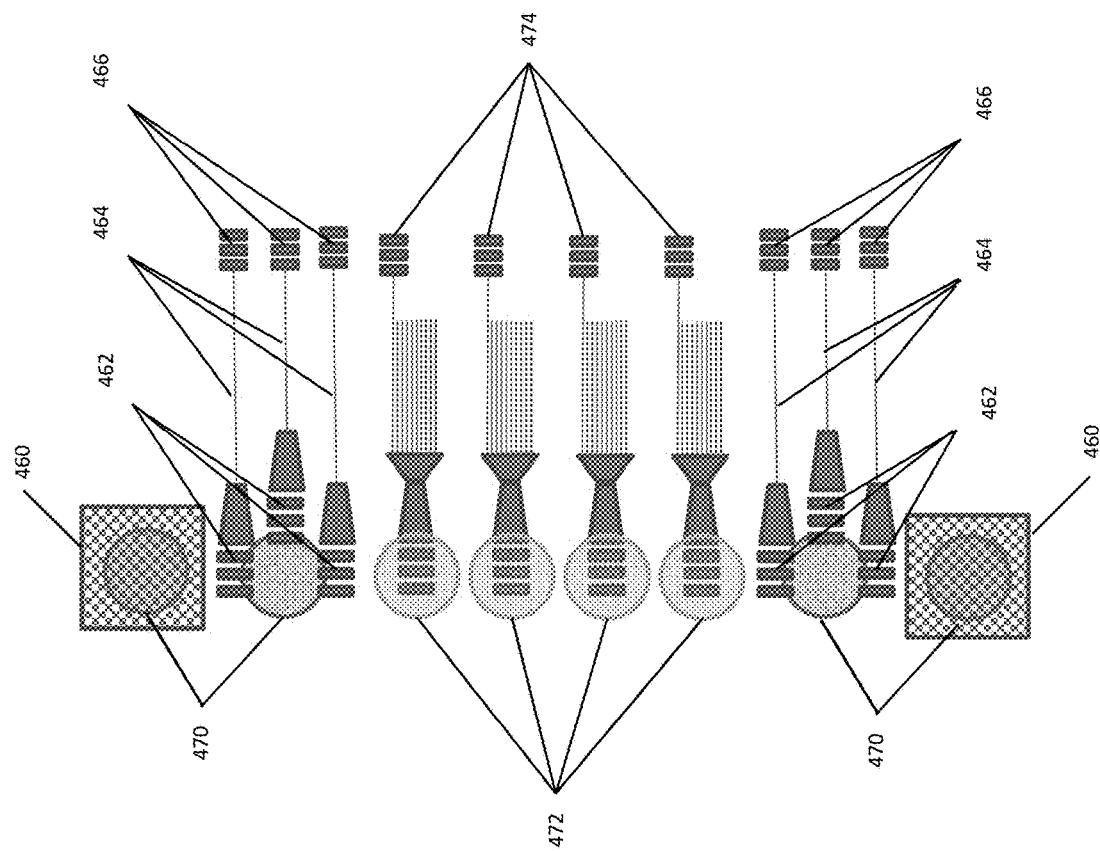
FIG. 4C shows another exemplary input coupling region that includes both waveguide alignment features and patterned region alignment features.

Another exemplary arrangement of alignment features in a target waveguide device is illustrated schematically in FIG. 4C. This device includes two "patterned", or "stipled", regions (460) that can serve as alignment features. These features can work independently of, or in addition to, the alignment features described above in FIGS. 4A and 4B and as also shown in the device of FIG. 4C. The patterned regions on the device of FIG. 4C can be illuminated by alignment beams, which are identified in the drawing as shaded circles (470). As previously mentioned, the alignment beams preferably carry approximately 1% of the power of the other beams. The illuminated patterned regions can thus be observed and monitored by a camera or other detector device within the analytical device in order to establish and/or maintain alignment of the optical source and the target waveguide. As just mentioned, the target device of FIG. 4C also includes two of the above-described alignment features, which comprise triads of alignment input couplers (462), their associated alignment waveguides (464), and their associated alignment output couplers (466). The alignment output couplers are typically high numerical aperture output couplers, which may be monitored from above by an alignment detector, such as an alignment camera, to facilitate alignment of the optical source and target waveguide device.

FIG. 4C also shows four shaded circles (472) representing the spots illuminated by sample excitation beams from an optical source. These full-power beams are coupled into the device through free space, preferably using low numerical aperture couplers, as described in detail elsewhere in the disclosure. As shown in the drawing, in this embodiment of the target device, the couplers direct the input optical energy from an optical source into tapered integrated waveguides which are directed through "fanout" regions to split the sample excitation beams into a larger number of split sample excitation waveguides, in this case 10 split waveguides for each input beam. The split waveguides ultimately deliver the input optical energy to nanoscale sample wells arrayed on the device. In the device of FIG. 4C, one of the 10 split waveguides associated with each coupler is directed to an output coupler (474) to serve as a power monitoring coupler, as described above. This coupler can be observed by an external detector, such as a detector camera, to monitor power levels passing through the excitation waveguides. The power monitoring couplers can provide immediate feedback to the system if the power output of an optical source changes during a measurement, or if alignment is lost between the optical source and the target waveguide device.

Figure 4D:
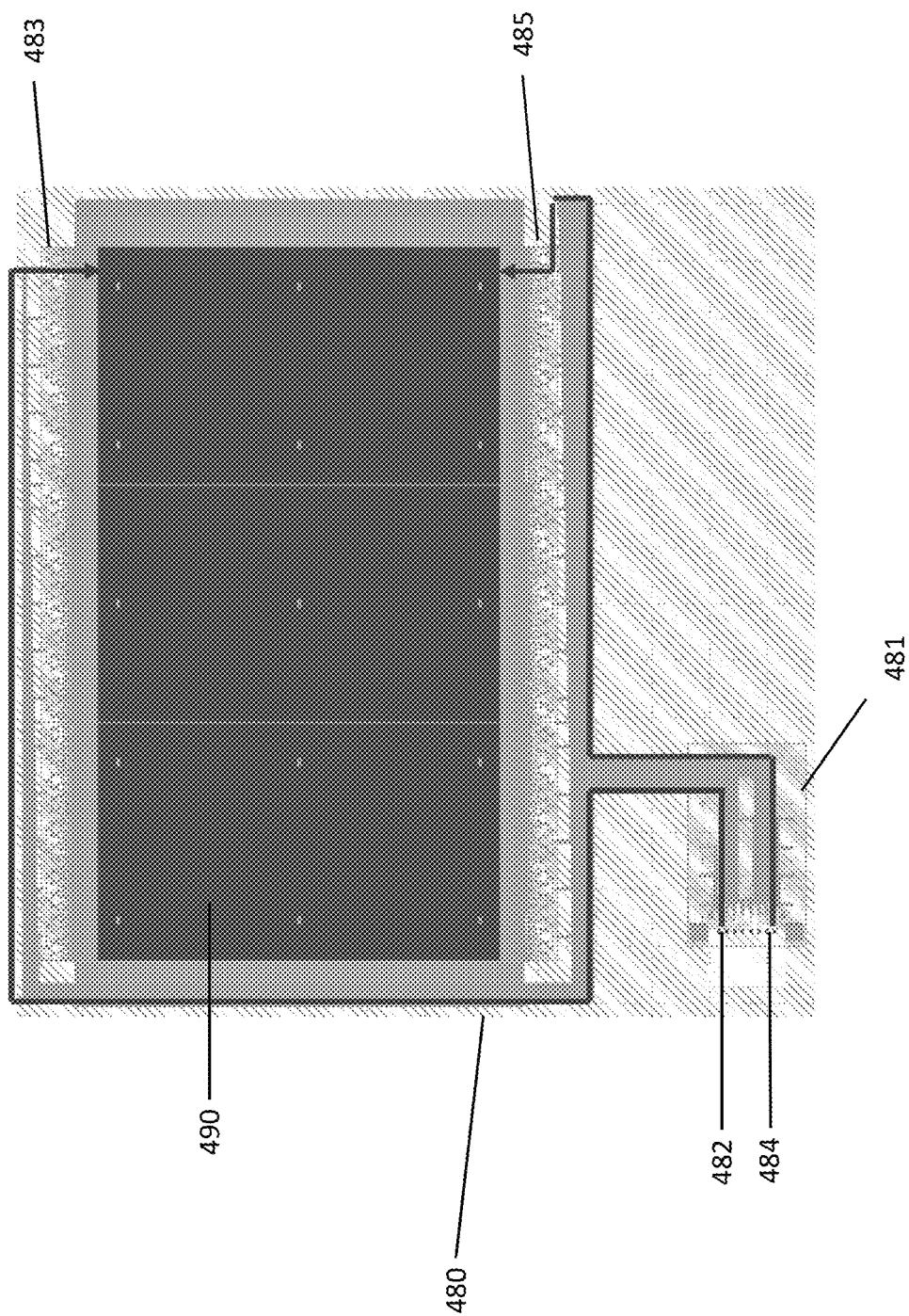
FIG. 4D shows the top view of an exemplary integrated target waveguide device, including the input coupling region, routing paths, fanout regions, and the arrayed nanoscale sample region.

FIG. 4D illustrates another exemplary target waveguide device (480). This device includes an input coupling region (481) in the lower left corner of the device and a large arrayed nanoscale sample well region (490) in the main central upper portion of the device. The input coupling region can further include alignment features, as described in detail above. FIG. 4D also illustrates two sample excitation waveguide pathways, one starting at low NA input coupler 482, and the other starting at low NA input coupler 484. Input sample excitation beams are coupled into these pathways and directed to the nanoscale sample wells either through the top fanout region (483) for input coupler 482 or through the bottom fanout region (485) for input coupler 484. Within the fanout regions, the excitation waveguides are split multiple times to create an array of split excitation waveguides to deliver optical energy to the nanoscale sample wells. As described in detail in co-owned U.S. Patent Application No. 62/133,965 and Ser. No. 15/072,146, the different path lengths encountered by optical energy that is input into the different couplers, and thus the different propagation losses suffered by the different excitation waveguide pathways, can be compensated by adjusting the power levels of optical inputs from the different couplers or by modulating the optical signals in other ways. The example of FIG. 4D also illustrates that the nanoscale samples can optionally be excited by optical energy transported through the same excitation waveguides from two different directions simultaneously. As shown in this drawing, light delivered from input coupler 482 and light delivered from input coupler 484 can be directed to the same nanoscale sample wells through their associated arrayed waveguides from opposite directions, if desired.

Figure 4E:
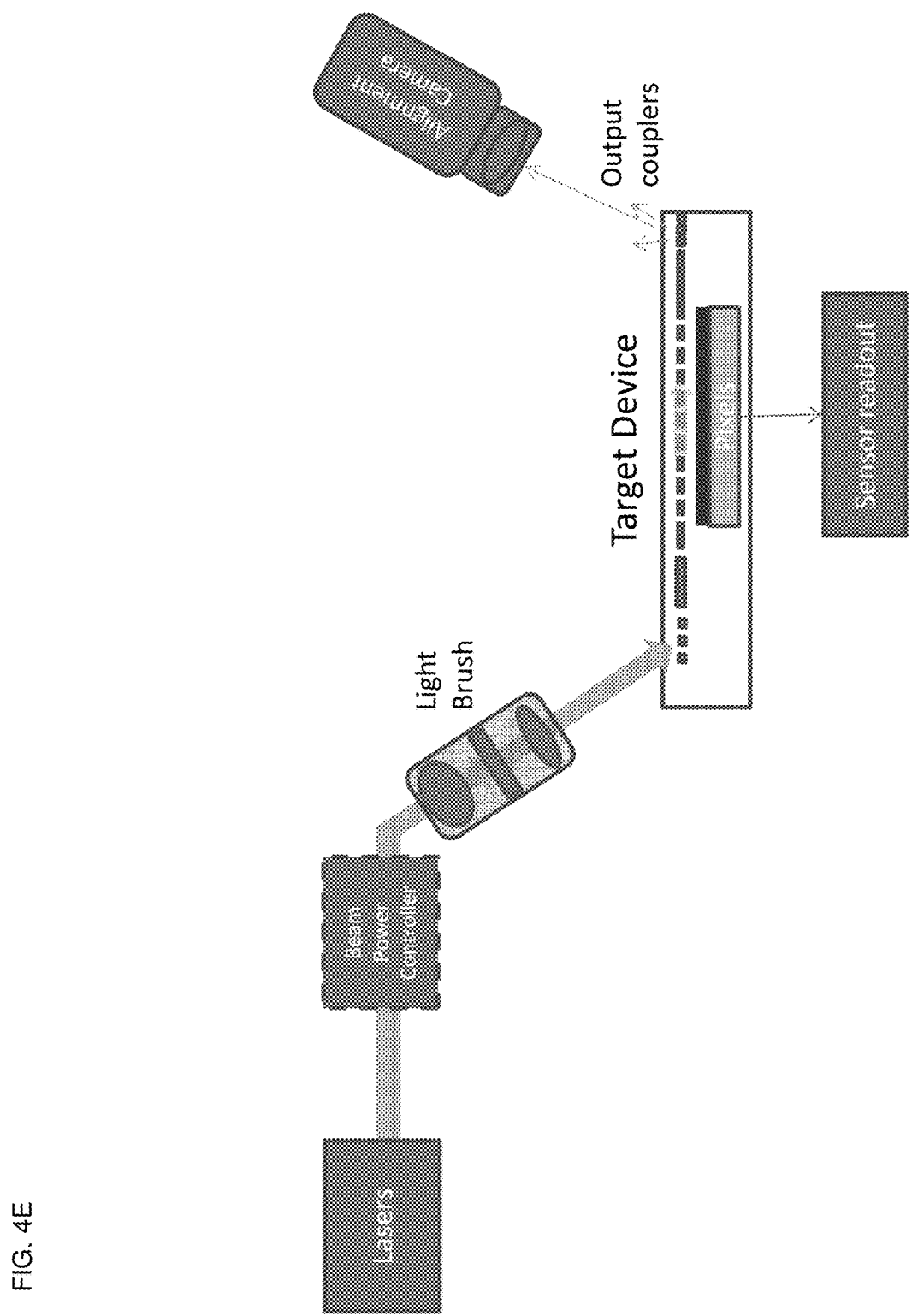
FIG. 4E shows an exemplary optical analytical system, including an optical source comprising lasers, a beam power controller, and a "light brush" to direct the optical input to the integrated target waveguide device. Also shown is an alignment camera.

FIG. 4E illustrates an optical analytical system of the instant disclosure, including a target waveguide device with at least one of the alignment features described in this section. The system comprises an optical source consisting of one or more lasers, a beam power controller, and a "light brush", which may correspond to one of the optical delivery devices of co-owned U.S. Patent Application No. 62/133,965 and Ser. No. 15/072,146. The system also comprises an alignment camera, an integrated detector component comprising an array of "pixels" for detecting optical outputs from nanoscale sample wells arrayed across the target device, and a "sensor readout" component that receives and analyzes signals from the detector. An optical beam or beams emitted by the lasers and passing through the beam power controller and light brush is represented as a thick arrow that illuminates an input coupler on the target device. The optical input is coupled into the device and is directed to one or more integrated waveguides within the device, as indicated by the smaller arrow. The optical input can optionally be directed to one or more alignment waveguides and/or one or more power monitoring waveguides. The alignment camera in this drawing is shown receiving optical outputs indicated in the drawing by even smaller arrows, from output couplers at the far end of the device. These couplers could be used to output light from the alignment waveguides and/or the power monitoring waveguides. It should also be understood that the alignment camera can, in addition or alternatively, receive optical signals from other alignment features such as one or more patterned regions, fiducials, or other reference marks on the surface of the target device. Optical energy traveling through the sample excitation waveguides illuminates samples in the arrayed nanowells, and fluorescence emitted from the samples is directed to appropriately aligned pixels in the detector layer, where the output signal is measured.

Figure 4F:
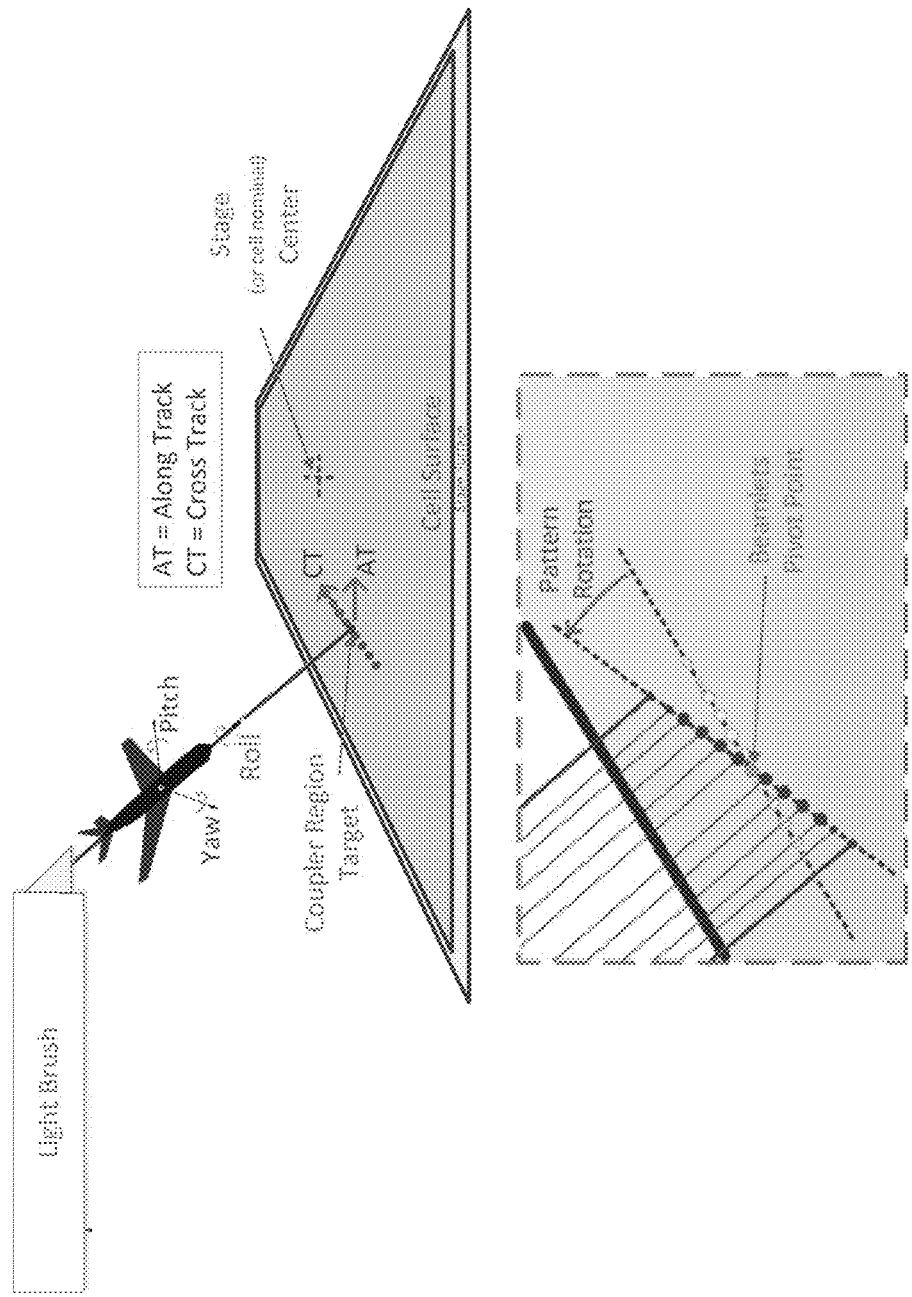
FIG. 4F shows the degrees of freedom to be controlled during the alignment of an optical source and a target device. The motions are designated along track (AT), cross track (CT), pitch, yaw, and roll (or pattern rotation). Not shown is movement in the up-down dimension.

FIG. 4F illustrates in graphic form how the light brush of FIG. 4E can be aligned with the target waveguide device that is disclosed herein, using any of the alignment features described above. Specifically, this figure illustrates the degrees of freedom that can be monitored and adjusted during the alignment of an optical source and a target device. As shown in the drawing, the airplane symbolizes three dimensions of rotation relative to the target device, and the "cell surface" corresponds to the surface of the target device. In addition to the rotational motions indicated in the drawing as pitch, yaw, and roll (or pattern rotation), the light brush and target device can move relative to one another in the x, y, and z coordinate space. Two of these motions are shown in the drawing as "along track" (AT) and "cross track" (CT) motions. Not shown in the drawing is an up and down motion to vary the distance between the light brush and target waveguide. As shown in the inset drawing, rotation on the "roll" axis causes the input beams to pivot around a particular axis. In this specific example, the light brush provides 12 separate input "beamlets". The two beamlets at each end of the illumination pattern are low-power alignment beamlets. Their targets on the device are illustrated as smaller circles in the line of input couplers on the surface of the device.

Accordingly, as described above, the alignment features of the instant disclosure can be arranged in various ways for various purposes. For example, as described above, they can be arranged to normalize for incident power. As also described above, the alignment features can be used as pump power grating couplers, at the expense of some efficiency. In addition, the output monitoring devices can be grating couplers, or can be other devices that are configured to redirect light towards an alignment detector, such as a camera.

Furthermore, the light coupled into the alignment grating couplers can be of the same wavelength as the pump power, but need not be. Likewise polarization, input (and output) angles can differ from the pump grating couplers, as desired. The light in the alignment grating couplers can be either coherent or incoherent with the pump grating couplers.

Accordingly, in some specific embodiments, the alignment feature can comprise one or more waveguides. In more specific embodiments, the alignment feature can comprise a plurality of low-power waveguide taps or a high-power beam tap. In other embodiments, the alignment feature can comprise a reference mark, for example a fiducial or other type of patterned region. The use of reference marks in the alignment of different components of an optical analytical system is well known in the art of printed circuit board manufacture and computer vision. See, for example, U.S. Pat. Nos. 5,140,646 and 7,831,098. The positional information obtained through monitoring the alignment features of the instant devices by an alignment detector can be used by the optical system to position the optical source and the target device relative to one another prior to the start of an analytical assay. The positional information can further be used during the course of an assay to maintain the position of the optical source and the target device dynamically through a feedback loop, as would be understood by those of skill in the art.

Target Waveguide Devices with Improved Power Handling

In some embodiments, the target waveguide devices of the instant disclosure comprise grating couplers with improved power handling capacity. In particular, one key factor limiting the amount of optical power that can be coupled through a grating coupler is the peak local temperature rise in the vicinity of a focused light beam of high optical power density. With parameters reasonable for optical coupling performance and typical materials and designs, the local temperature in a region below the coupler can quickly reach levels that are likely to impair performance or cause physical damage, even with moderate input power (e.g., potentially much less than 1 W).

Indeed, while various examples exist of grating couplers as an interface between free-space or fiber optic inputs and waveguides in microfabricated integrated photonic circuits, issues may arise when such couplers are used to transmit substantial amounts of optical power. While perfect coupling efficiency is unattainable, and with the best reported coupling efficiencies in the range of 50% (i.e., −3 dB), a substantial fraction of incident power is not coupled into the waveguide. Even if a substantial portion of the uncoupled power is reflected or scattered away from the vicinity of the coupler, however, some local absorption is inevitable. With increasing input power, temperature in the vicinity of local absorption for a tightly-focused beam may rise to levels that may impair coupler performance or cause physical damage.

As described herein, however, by reducing the local thermal resistance between a limited absorbing region and the bulk of the microfabricated component, higher input power can be coupled without damage or impairment of coupler performance. For a fluorescence application, this means that greater pump intensity can be utilized to improve signal-to-noise performance, and an increased area or number of sample sites can be interrogated. In addition, for the instant target devices and systems, where a plurality of input ports can be required due to thermal limitations, allowing more power per input port allows the number of input ports to be reduced, thus simplifying the optical system and the associated target device.

Accordingly, in the grating couplers of the instant target devices, a layer of material with relatively high thermal conductivity can be fabricated below the grating in order to improve the lateral heat transfer within the device and thus reduce peak temperatures.

If the design of the coupler includes a reflection layer below the grating (optionally with some bottom cladding material in between) in order to improve coupling efficiency, then the conductive layer can be located immediately below and in contact with the layer of material that forms the reflection layer interface with the bottom cladding. Depending on materials, the interface between the conductive layer and the bottom cladding below the coupler can itself form the reflection layer, e.g., in the case of an interface between $SiO_2$ and Al for visible-wavelength applications.

In order to serve as an effective heat spreader, the thermally-conductive layer should have a thickness greater than required for purely optical purposes (which can in specific embodiments be only on the order of 10 nm). In some embodiments, the heat spreading layer can be from 10 nm to 1000 nm thick. In more specific embodiments, the layer can be from 20 nm to 500 nm thick. In even more specific embodiments, the layer can be from 50 to 250 nm thick. A dielectric stack can optionally be provided above the conductive layer in order to further reduce absorption and thus peak heat load.

In particular, in some embodiments, the operating wavelength, numerical aperture/mode size, materials used for fabrication of the grating coupler and specific design of the grating coupler (e.g., binary grating, blazed grating, focusing grating, etc.) can be varied. In addition, the materials and process details for fabrication of the heat spreader can be varied—e.g., any sufficiently thermally conductive material that is appropriately process-compatible could be used for the heat spreader. For example, aluminum, tungsten, silicon carbide, copper, indium, tin, titanium nitride, or others can be used depending on the process technology. In specific embodiments, the thermally conductive material is aluminum. Additional thin film layers can be provided above the heat spreader in order to tailor optical performance (e.g., reflection and absorption for a particular wavelength, polarization, etc.).

The specific dimensions of the heat spreader (e.g., lateral extent and thickness) can be varied to suit relevant design constraints, including photonic circuit geometry, materials, and expected power. While a reflective layer below a grating coupler can be made of a material that has relatively high thermal conductivity and thus can itself act as a heat spreader to some extent, the required thickness of such a reflective layer from an optical perspective can be quite small (e.g., 10-100 nm); at such thickness, performance as a heat spreader is accordingly somewhat limited. When the layer thickness is substantially greater than required for optical purposes (e.g., 100 nm to 1 µm or more, depending on the geometry and materials used) heat spreading performance can be substantially improved.

Exemplary target waveguide structures are illustrated graphically in FIG. 5, where the structures of FIGS. 5A and 5B do not include heat spreaders, and the structures of FIGS. 5C and 5D include heat spreaders below the grating structure. The structures illustrated in FIGS. 5B and 5D further include a reflective layer below the coupler to improve efficiency of optical coupling as described above.

Typically the heat spreader will extend from the region below the grating to the edge of the chip where it is in thermal contact with the carrier that holds the chip. The contact with the carrier that holds the chip allows for heat on the chip to be transferred off of the chip for thermal management. In some cases the carrier has a heat sink that is in thermal contact with the heat spreader on the chip. In some cases, active cooling is provided to the heat sink. A heat spreader also could be used as, or used below, an absorbing interface instead of a reflecting interface below the grating coupler. This can be advantageous, for example, if process tolerances are insufficient to guarantee a desired phase relationship between the incoming beam at the grating coupler and a reflective layer below the bottom cladding. Where such tolerances are insufficient, coupling efficiency can vary undesirably due to process variation. In this case, higher absorbed heat loads would be expected for a given coupled power, and thus a means of thermal mitigation becomes even more critical.

For the sake of description, the terms "above" and "below" here refer to relative position of layers for a case in which the input beam is incident from the top of the layer stack, as commonly described. In some embodiments, however, an inverted stack can be used, in which case the beam is incident from below. In such a case, a heat spreader can still be applied to laterally disperse heat and/or aid in its extraction from the top of the layer stack.

Example 6 below demonstrates experimentally the benefit of a heat spreading layer in mitigating laser damage at power densities typical of those used in the instant devices and systems.

Active Waveguide Coupling

According to another aspect, the instant specification provides optical systems comprising an optical source and a target waveguide device, wherein the optical energy from the optical source is actively coupled to the target device. In traditional optical systems containing an optical source and a target waveguide or fiber optic device, the components are associated using either permanent coupling or connectorized coupling. For example, in systems where the target optical device is contained within an integrated optical chip, is buried underground, or is strung under the ocean in a telecommunications cable, the target device is carefully aligned to the input source or sources (e.g., a laser diode, an LED, or the like) and permanently fixed in place. This process is expensive, time consuming, and usually involves glue or other permanent adhesive. The connectorized approach is similar in that it requires the careful alignment of a connector to the target device. In addition, connectorized connections are usually made manually by a human operator.

The active coupling approach described herein differs from the conventionally coupled systems in that it involves a target waveguide device that is readily inserted and removed from the optical system. There is additionally a premium placed on fast cycle times, with the target device being coupled to the optical source as soon as possible after its insertion into the system. Although a connectorized approach is clearly more suited for this type of operation than a permanently coupled approach, even the connectorized approach typically requires human intervention to create the connection. Connectorization also adds significant cost to the system—in the case of telecommunications systems, typically $100 per connector.

An active coupling strategy is usefully applied to any of the coupled systems described herein. It typically involves a laser path that includes motorized beam steering and in some cases also motorized focus, and it also preferably includes a feedback loop. Simple feedback loops are described in co-owned U.S. Patent Application No. 62/133,965 and Ser. No. 15/072,146. For example, a waveguide tap fabricated within the target waveguide device can be used to split out a small amount of laser power from the guided mode, and the tapped power can be routed to a convenient location for collection by a camera or other detector to monitor and adjust the optical coupling through the system. Alternatively, or in addition, light does not necessarily need to be explicitly coupled out of the device in order to provide feedback. Instead, a camera oriented toward a specific waveguide region can determine the amount of light within the waveguide, in the same way that waveguide coupling losses are estimated by quantifying the scattering loss along the waveguide.

Another closed-loop feedback alternative for monitoring coupling is to integrate a detector onto the waveguide itself. Although this approach may complicate fabrication of the target device and may increase cost (for example, a hybrid flip-chip approach is common but expensive, and a monolithic approach requires wires), such integrated detectors are known in the art.

For any actively coupled system, the optical source is ideally steerable in x,y, and/or tip/tilt directions, and can additionally be focusable. It can in certain embodiments be advantageous to apply more sophisticated beam shaping to the optical source beam in response to the coupling efficiency, as measured in the closed feedback loop. Such active control over the optical input loosens instrument tolerances on placement of the target waveguide device within the instrument, on target device packaging tolerances and substrate tolerances, and also on waveguide alignment tolerances (e.g., on mask alignment). Fabrication variations in waveguide shape and size can also be loosened by an adaptive optical input with a closed-loop feedback. Finally, instrument drift tolerances can be significantly loosened with closed-loop adaptive optical coupling.

A variety of coupling methods can be used independently for inputting an optical signal into a target waveguide device. These methods can additionally or alternatively be used without limitation to couple optical signals out of the device, for example to an optical detector, detectors, or the like. The three classic approaches to coupling include transverse or endfire coupling, prism coupling, and grating coupling. Each of these techniques has certain advantages with respect its use in an optical analytical system. In particular, transverse coupling requires little or no space on the target device and provides a high level of overall coupling efficiency (70-90%). Transverse coupling, however, requires polishing of the side of the target waveguide device, can impact packaging of the device within an optical system, and can require sensitive alignment of the target device in three dimensions. Prism coupling also displays relatively high coupling efficiencies (50-80%), but it requires the incorporation of a high-index prism into the system packaging, space on the surface of the target device, and alignment of the target device with respect to prism tilt. Standard grating coupling efficiency can be relatively low, but the efficiency is significantly improved (to 90%) with specific grating profiles and incident beam energy distributions. Grating coupling also requires space on the surface of the target device and is sensitive to tilt alignment between the optical source and the target device.

As will be further described in the Examples, the overall coupling efficiency of an optical system is defined as $$\eta = \eta_{instrument} \cdot \eta_{target\ device} \cdot \eta_{optical\ source}$$

where the instrument coupling efficiency ($\eta_{instrument}$) describes the ratio of power in the guided mode to the total power delivered to the target device by the instrument. The denominator includes unused power that does not couple into the target device in the form of substrate modes or other:

$$\eta_{instrument} = \frac{\text{Power in guided mode}}{\text{Total incident power}}$$

where the target device coupling efficiency ($\eta_{target\ device}$) describes the ratio of power in the guided mode to the total power coupled into the device, and where the denominator includes power in substrate modes which must be prevented from reaching any detector elements:

$$\eta_{target\ device} = \frac{\text{Power in guided mode}}{\text{Total power in device}}$$

and where the optical source efficiency describes the fraction of light coupled into a guiding layer that can be successfully coupled into individual channel waveguides:

$$\eta_{optical\ source} = \frac{\text{Power in guided mode}}{\text{Total power planar waveguide}}$$

The values of $\eta_{target\ device}$ and $\eta_{optical\ source}$ should generally be considered more important than $\eta_{instrument}$ within an integrated system, because they represent light scattered inside the target waveguide device that can increase background signals and thus put pressure on the laser rejection filters and other background mitigation strategies. Low instrument efficiencies can be compensated for by changes in instrument design. Exemplary target waveguide design and estimation of coupling efficiency is provided below in Example 2.

Multimode Integrated Coupler

According to another aspect, the instant specification provides multimode integrated optical coupling devices and optical systems comprising such devices. As described above, target waveguide devices typically include a limited number of optical inputs that are coupled to an optical source. Optical energy entering the device is directed by waveguides to locations of interest within the device through splitters that are fabricated within "fan-out" regions of the target device. The devices disclosed in this section of the disclosure, however, include a multimode coupler element. In these devices, the role of the multimode coupler element is not to route light to individual output waveguides, but rather to distribute the light into pre-planned "hotspots" where nanoscale sample wells are located.

Figure 6:
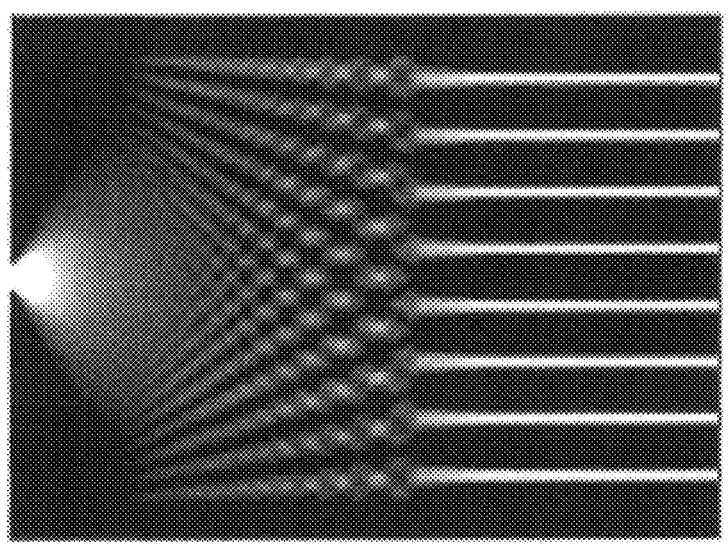
FIG. 6 illustrates "hotspots" created by a multimode coupler.

The design of the multimode coupler device allows flexibility in the spacing, location, number, and relative brightness of the hotspots. Multimode couplers are a mature technology with a great deal of process development and design approaches already in place. A photograph of an exemplary 1×8 splitter device is shown in FIG. 6, where hotspots are clearly evident in an arrayed pattern across the surface of the device. A nanowell can accordingly be placed on top of each hotspot.

The design space of such multimode devices is quite flexible, with devices designed to have different spacing and intensity. In particular, in some embodiments, the devices are designed to display more efficient use of laser power, lower propagation loss, lower autofluorescence, allow a more flexible layout of nanowells, and use less space on the chip for routing and/or splitting. In some embodiments, a specified number of waveguides are fanned out and illuminated, but the waveguides are terminated in a multimode coupler structure. In specific embodiments, the structure is square or rectangular, or it could be another structure that uses space more efficiently, for example with greater packing density. The use of a multimode coupler could partly or completely eliminate the large cascade of splitters necessary in a fan-out region to divide a single input waveguide into thousands or more separate waveguides for transmitting light to the nanoscale sample wells.

In some embodiments, the multimode couplers are designed to provide varying intensity. For example, the intensity can be programmed to compensate for scattering loss, propagation loss, loss at the nanowell, and the like.

In some embodiments, the devices are designed to provide programmable excitation. Such devices are similar to classic waveguide illumination, with optical switches implemented to switch on and off different regions of the chip. In some embodiments, the devices are designed to provide variable excitation. As is used in classic waveguide illumination, variable optical attenuators (VOAs) can be integrated into different lines to provide for adjustment of the power density at different groups of nanowells. Such variable excitation could be used in a "per chip SNR" optimization, where it could be used to adjust power output after initial results from subsections of a particular chip. It could also be used to program the chip with a diversity of excitation powers and simultaneously collect data at different optimization points on the laser titration curve.

All of the above optical features could be achieved using traditional optical trains as well as with classical waveguide illumination approaches, but they are far simpler to achieve using a multimode coupler device. In addition, a multimode coupler overcomes some of the problems that can arise with traditional optically coupled devices. For example, it is generally difficult to space output waveguides as closely together as desired because of interference between guided modes. Autofluroescence may also limit the potential SNR of a classical waveguide device. The splitters used in a classical waveguide device may additionally be problematic in that they require significant amounts of space on the device. Traditional splitters may also limit accuracy of the device, as each stage adds variability into the different branches.

Polarization Schemes for Efficient Excitation of Nanowells

According to another aspect, the instant specification provides methods and devices for optimizing the excitation of arrayed nanowells in an optical analytical device. As described above, analytical reactions, preferably immobilized single template/DNA polymerase sequencing reactions, are excited with laser light, typically near metallic nanostructures. In such systems, the polarization of the optical source is an important consideration in implementing the design. In typical systems, the input light is linearly polarized due to the properties of the optical train. In most circumstances, however, a different polarization would be more efficient. Higher efficiency results in better uniformity of excitation and lower power requirements for excitation. Better uniformity improves the quality of data generated from the analytical reaction, and lower power requirements translates into lower autofluorescence and lower heat generation.

In the above-described integrated target devices, the nanowells are illuminated by an optical source within the device, typically an excitation waveguide. The nanowells are preferably cylindrical in shape, wherein the inner walls are commonly formed from a metallic layer, and the bottom of the nanowell is commonly a glass/water interface. As is known in the art, the penetration of an evanescent electric field into a metal varies with polarization of the optical source, and there is correspondingly a strong polarization dependence for the evanescent fields exciting nanowells in such devices due to the metallic layer surrounding the nanowells. When an enzyme, such as a DNA polymerase, is immobilized at a specific location within a nanowell, the strength of the electric field from the optical source thus varies significantly depending on the position of the immobilized enzyme, and thus the fluorescent target molecule, within the nanowell.

Figure 7:
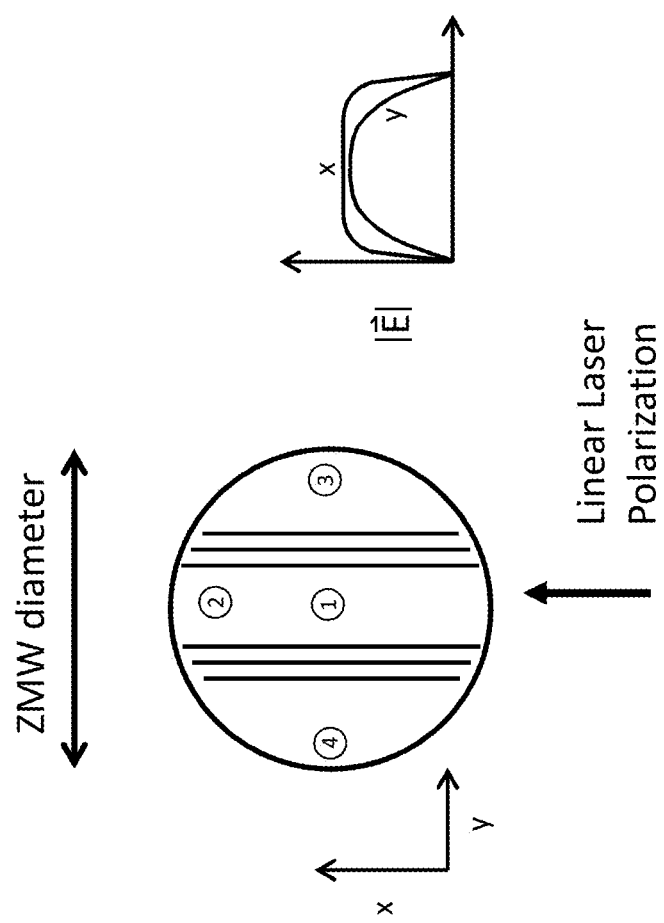
FIG. 7 shows the effect of linear polarized excitation light on targets at different locations in a nanowell/ZMW.

The instant inventors have discovered that a simple linear polarization of excitation light generally provides relatively poor field uniformity inside a metallic nanowell, but that the uniformity can be improved by an alternative approach to polarization. In particular, for some systems using linearly polarized excitation light, the falloff in excitation energy can be a factor of two between edge locations aligned with the laser linear polarization (0° and 180°), and locations orthogonal to the polarization direction (90° and 270°). For example, as illustrated in FIG. 7, target molecules positioned in a nanowell (i.e., a ZMW) at locations 1 or 2 experience high laser electric fields when excited by linear-polarized laser light, whereas those positioned at locations 3 or 4 experience significantly lower electric fields. A graph representing the estimated falloff in electric field along the x and y coordinates is also shown in FIG. 7. By comparison, circularly polarized light reduces the variability in the excitation field by half. It should be understood that the fluorescence signal varies quadratically with excitation electric field, so the impact of non-uniformity in excitation field can be significant.

Figure 8:
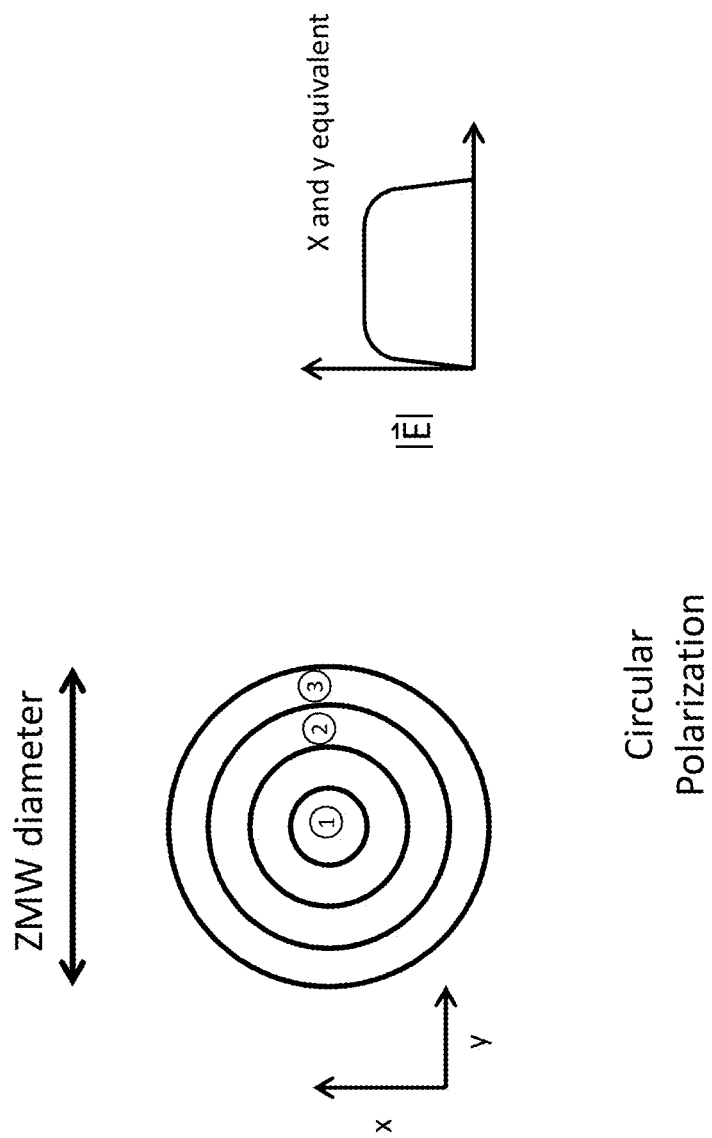
FIG. 8 shows the effect of circular polarized excitation light on targets at different locations in a nanowell/ZMW.

As an alternative, if a nanowell is excited with circularly polarized light, while there is still a falloff between the peak electric field location in the center of the nanowell compared to the edge, this falloff is radial and not as deep. Accordingly, as shown in FIG. 8, target molecules positioned in a nanowell at locations 1, 2, or 3 would experience similar electric fields when excited by circularly-polarized light. It should also be noted that other system performance metrics may be affected in different ways by the target molecule position, and an increased uniformity of excitation field is but one factor in improving performance of the system. However, converting to circularly polarized light removes a significant factor that is a function of azimuthal and radial location within the nanowell and thus reduces overall variability in the excitation level.

Depending on the particular optical system, the conversion of an excitation beamlet from linear to circular polarization may be more or less complicated. For a relatively simple case, for example where the excitation beam is provided in a traditional optical train, the conversion may be effected, for example, by the simple addition of a quarter wave plate at a collimated location in the laser path. This modification converts the light at that spot from linear polarization to circular. The ultimate polarization at the nanowell will be slightly different, however, due to reflections and asymmetric filters. The design of an appropriate waveplate or two that results in true circular polarization at the nanowell is straightforward, however, as would be understood by one of ordinary skill in the art, if the optical design details of the lenses and filters in the system are known.

For a more complex and compact optical system, for example where the optical signal is transmitted through a waveguide, and where a metal is used, as described above, to define the excitation volume and to provide enhancement of the laser field strengths, the field strength may be spatially dependent on the polarization direction. Optical waveguides are generally polarized, with two possible orientations (TE and TM) which are orthogonal to each other. A slab waveguide can combine TE and TM modes, such that the TE mode can be used to propagate one laser wavelength (532 nm) and the TM mode can be used to propagate a second wavelength (642 nm). For purposes of the instant disclosure, however, a slab waveguide can be used to create circular polarization, or an approximation of circular polarization, in the waveguide. This, or an even more complex polarization scheme, provides maximum uniformity in electric field across all possible target molecule locations in samples illuminated by such waveguides. FIG. 9 provides a schematic representation of the effect of target molecule location on excitation by different TE modes.

Furthermore, while waveguides are typically designed for transmission of either TM or TE modes, there is a third unique mode definition, TEM, that can be used to transmit optical energy to arrayed nanowells in a target device. For example, a square embedded guide with the same index in all cladding directions could simultaneously support both TE and TM transmission, and if the symmetry is perfect, or nearly perfect, both TE and TM will have identical group velocities. Similarly, a TEM mode can be used for minimal polarization anisotropy, and hybrid modes in general can be constructed quite generally to match a desired polarization configuration. FIG. 10 illustrates how these modes can be combined with different group velocities to create desired electric field patterns in a waveguide.

Multi-look and Multi-hotstart Approaches

According to yet another aspect, the instant specification provides devices and systems for highly arrayed optical analysis in which the target nanowells may not necessarily be illuminated simultaneously. In other aspects, the analytical reaction occurring within the target nanowells may not necessarily be initiated simultaneously in all of the nanowells.

In some embodiments, the instant integrated target devices involve a single sequencing experiment per chip, and all nanowells on the device are illuminated simultaneously. In other embodiments, however, only half of the nanowells are illuminated at a time. In still other embodiments, one third, one fourth, or even fewer of the nanowells are illuminated at a time.

In some embodiments, a single "hotstart" initiates polymerase activity in all of the nanowells simultaneously. In other embodiments, polymerase activity is initiated at two, three, four, or even more times on a given target device. Initiation of polymerase activity may be triggered in various ways, for example by the addition of an essential component of the enzymatic reaction, e.g., one of the four nucleotides in a DNA polymerase-catalyzed reaction, that is initially not present in the sample or that is initially present in limiting amounts. In some embodiments, polymerase activity is triggered by the release of a trapped form of an essential component or by activation of an otherwise inactive form of the component. In these embodiments, the essential component could be, for example, one of the four nucleotides required for the DNA polymerase reaction, or could be the DNA polymerase enzyme itself.

The multi-look and multi-hotstart concepts disclosed herein address some of the challenges in the use of integrated waveguide devices for the measurement of nanoscale analytical reactions. For example, autofluorescence in the waveguide core material, laser scattering light levels combined with limited design space for laser blocking filters, heating of the coupling pad due to imperfect coupling efficiency, and large laser power required can be problematic. Independent of the waveguide illumination scheme, the compute bandwidth is an important engineering problem. The figure of merit for all of these issues is divided by the number of looks in a multi-look approach (e.g., if a 10 W laser is required for single look, 5 W would be required for two-look; if the autofluorescence level is X in a single look, it would be X/2 in a two-look, and so on). Although the use of multi-look approaches decreases instrument throughput, it can also reduce the cost per analytical reaction of the device and can also simplify/reduce the cost of the instrument.

In terms of waveguide illumination, there are several ways to implement multi-look excitation. An instrument-centric approach is to include multiple optical inputs on the target waveguide device, and aim an input optical beam at one of these inputs at a time. FIG. 11 illustrates how this approach could be implemented with two basic coupling schemes. Specifically, FIG. 11A compares the single-look design (top) and a 3-look variant (bottom) in a target waveguide device containing grating couplers. With the 3-look variant, a single input optical beam is aimed at the three separate input grating couplers in sequence in order to excite samples along the "Look 1", "Look 2", and "Look 3" waveguides, respectively. FIG. 11B shows the corresponding single-look (top) and 3-look (bottom) design variants for target devices employing endfire coupling. The corresponding designs for target devices employing prism coupling are not shown but would be similar to the designs shown for the grating-coupler devices of FIG. 11A. Specifically, in the prism-coupled devices, the input grating couplers of the designs shown in FIG. 11A would be replaced with input prism couplers.

Figure 12A:
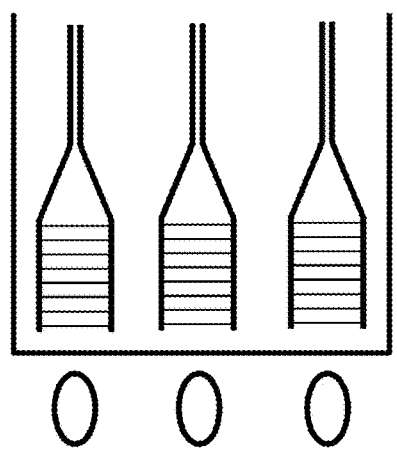
FIGS. 12A-12C illustrate single-look (A) and multi-look (B and C) devices configured for illumination by three separate input optical beams. The devices include input grating couplers (A and B) or endfire couplers (C).
Figure 12B:
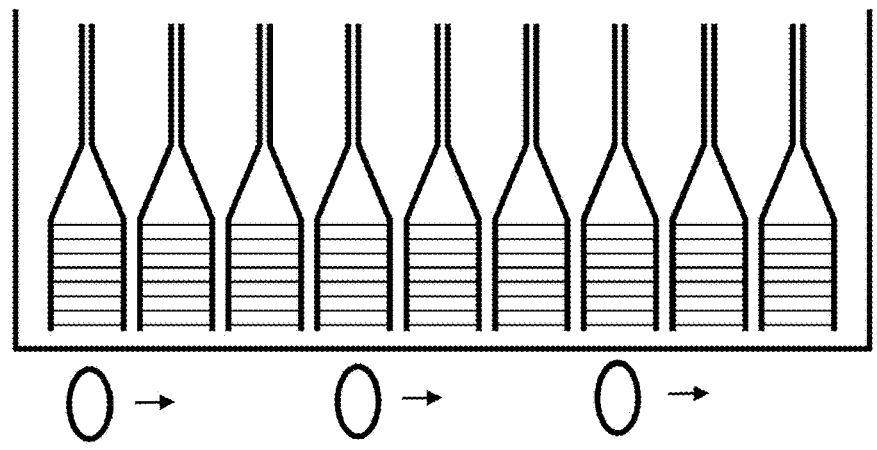
Figure 12C:
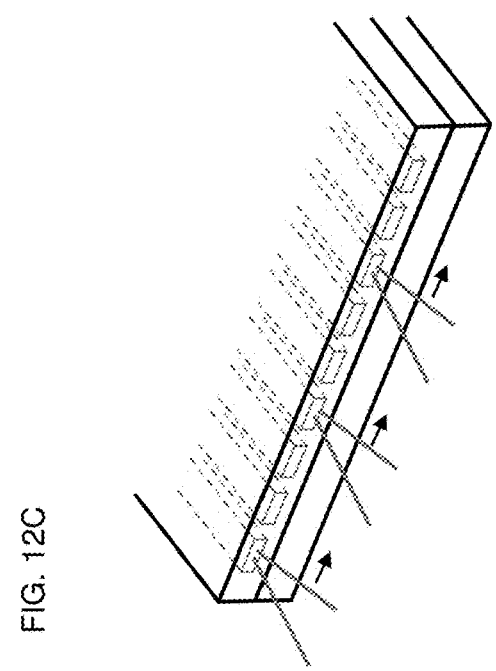

A further example of the multi-look approach, in particular where the instrument provides multiple optical beams for illumination of a target device, is illustrated graphically in FIG. 12. A single-look device with input grating couplers and designed for use with three input optical beams is shown in FIG. 12A. A corresponding 3-look device with input grating couplers and designed for use with three input optical beams is shown in FIG. 12B. In each case, the three input beams are indicated in the drawing as ovals positioned to the left of the respective devices. It should be understood, however, that these beams would, in practice, illuminate the input couplers on the devices and be launched into the integrated optical waveguides in each case. Similar designs could be prepared using prism input couplers in place of the grating input couplers. FIG. 12C shows a 3-look endfire-coupled device for use with three input beams. The input beams in this device are designated by the three pairs of convergent lines targeting the waveguides. In FIGS. 12B and 12C, movement of the three input beams from look to look is indicated by small arrows.

A variety of on-chip optical switches are also available for implementing the multilook concept. An efficient and inexpensive example is a thermally-activated Mach-Zehnder switch. Since these switches are relatively slow and display different on/off speeds, they are most suitable in instruments where switching times of one or two seconds are sufficient. It should also be noted that on-chip switching is independent of the coupling scheme. An endfire-coupled target device with a single optical input is illustrated in FIG. 13, but corresponding grating-coupled and/or prism-coupled target devices could likewise be designed. As shown in the device of FIG. 13, three Mach-Zehnder switches are used to control the excitation of four different waveguides to provide four separate "looks" in this device. A more detailed view of an individual thermal Mach-Zehnder switch is also shown in FIG. 13. Such switches are known in the art and can be readily included in the design and fabrication of an integrated waveguide device.

Figure 14B:
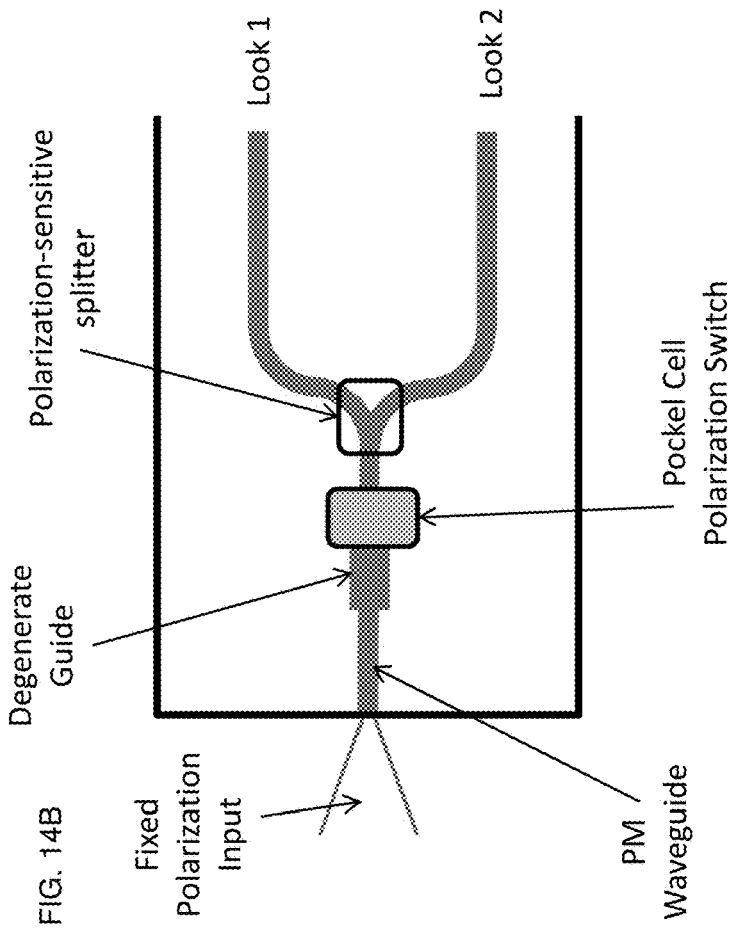
FIG. 14B shows a device-level implementation of a polarization-based 2-look system.
Figure 14A:
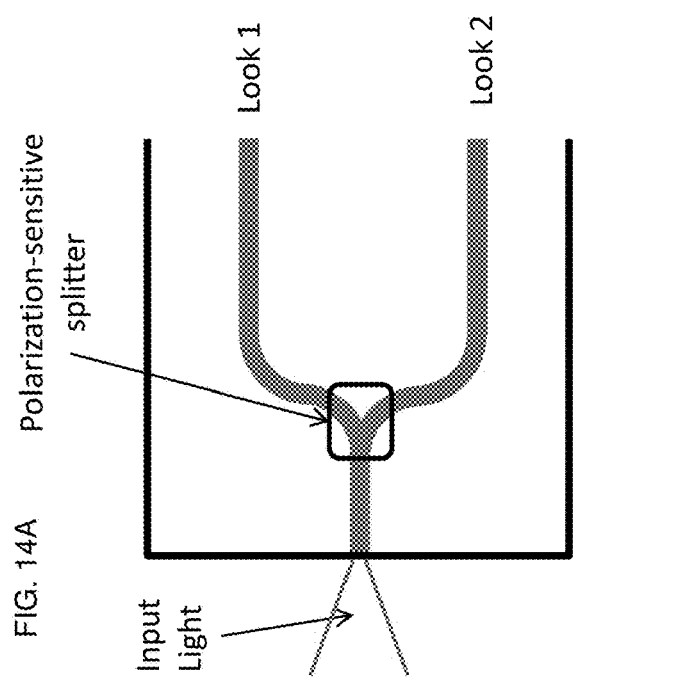
FIG. 14A shows an instrument-level implementation of a polarization-based 2-look system.

Polarization can also be used to implement a two-look scheme. The use of polarization can advantageously require fewer moving parts or smaller adjustment ranges in the instrument, and less real estate than an on-chip version. An instrument-level implementation of such an approach is depicted in FIG. 14A, and an on-chip implementation is depicted in FIG. 14B. Specifically, the target device shown in FIG. 14A includes a polarization-sensitive beam splitter that is used to route light between two different waveguides ("Look 1" and "Look 2"). The optical input is switched by the instrument between polarization states (e.g., s and p) for recognition by the beam splitter. The target device shown in FIG. 14B includes a polarization-maintaining input waveguide that leads to a degenerate guide. A Pockels cell polarization switch, or the like, is used to modulate the polarization state of light passing through the device, and a downstream polarization-sensitive beam splitter routes light between two different waveguides ("Look 1" and "Look 2") for transmission to the respective nanoscale sample wells.

Figure 15:
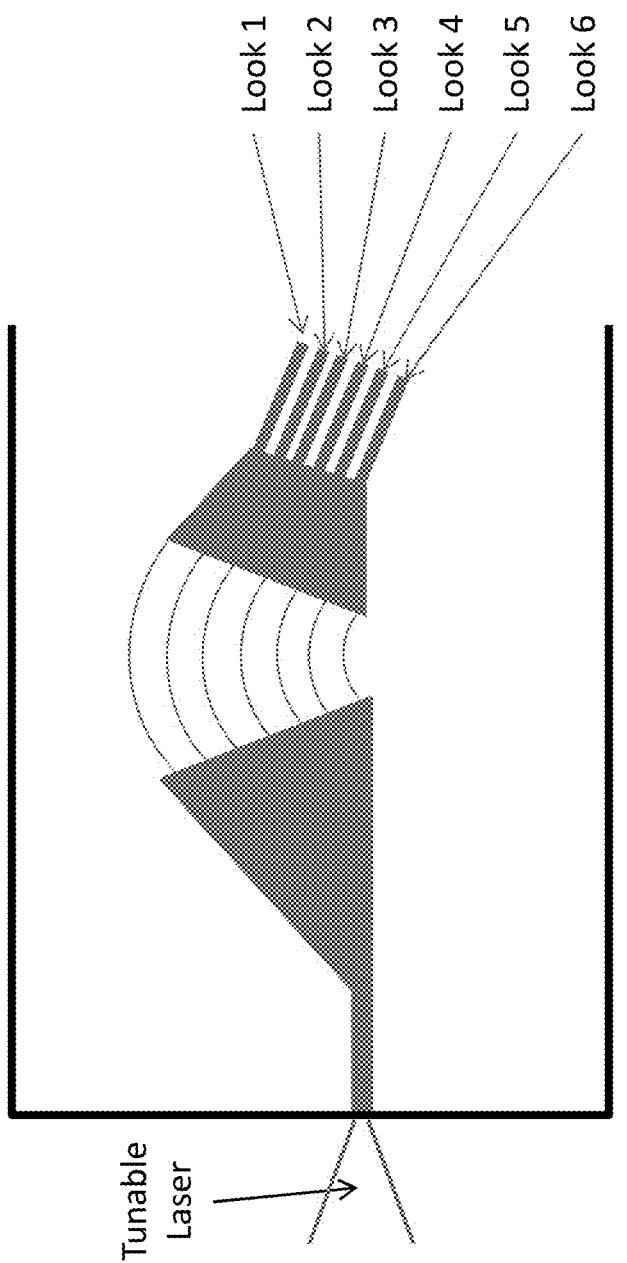
FIG. 15 illustrates the use of an arrayed waveguide grating (AWG) to tune excitation wavelengths for multi-look reactions.

Wavelength tuning can also be used for implementing the multilook concept. In this approach the laser in the instrument is a tunable laser, and the optical input is routed through the device according to the wavelength. A basic arrayed waveguide grating (AWG) device could be used here, with a large number of looks enabled according to established AWG technology. An exemplary AWG-implemented target device with six output waveguides is shown in FIG. 15. Note that the excitation source could be tuned, for example in 25 nm increments, with each increment being directed to a different "Look". Alternatively, a broadband source (e.g., an LED) could be used along with a tunable filter that would select one wavelength at a time. The wavelength step size should be chosen to be small enough that the differences would not have a significant impact on excitation of the subject analytical reaction.

Fiber Spacing Concentrators and Fiber Alignment

According to yet another aspect, the instant specification provides fiber spacing concentrators with reduced loss and improved channel-to-channel uniformity.

Multi-channel microfabricated optical devices are of use in telecommunications applications, for high-speed optical interconnects in computing, and potentially for bioanalytical applications. Optical fibers are typically used to transmit signals at the macro scale, and various means can be used to couple the signal between a microfabricated structure and an optical fiber. However, there is a large mismatch between the minimum pitch of coupling structures on a microfabricated component (which structures can be roughly the size of the optical fiber mode and thus spaced on this scale) and the minimum pitch of an array of optical fibers (limited by the fiber cladding or coating diameters, which can be 30× the mode diameter or more). From a practical standpoint, this means that more area—and thus more cost—must be devoted to coupling structures on the chip than required from an optical perspective.

A fiber spacing concentrator (FSC) is a planar microfabricated passive optical component used to provide well-defined spacing of multiple individual optical channels with a fixed pitch that can be made much tighter than the spacing between optical fibers in a fiber array. Embodiments of such FSCs are available commercially. See, e.g., fiber spacing concentrators from Teem Photonics, Meylan, France (http://www.teem-photonics.com/fiber-spacing-concentrator.html).

Use of an FSC for optical coupling allows for much tighter spacing of couplers on the target microfabricated optical device, thus reducing the required area and cost for a given number of channels. However, this benefit comes at the cost of some loss of optical transmission, which can be non-uniform across the array. Additional power and potentially additional degrees of freedom for power control can be required to compensate for such non-uniform losses, which ultimately add to system cost.

From a physical perspective, the FSC consists of three key components: a microfabricated part in which waveguides are defined, a mechanical assembly for holding an array of fibers, and the fiber array itself. The fiber array can be fixed (e.g., bonded) in the mechanical assembly before subsequent alignment of the mechanical assembly and bonding to the waveguide component.

A large fraction of the losses in an FSC assembly likely arise from the spatial mismatch between the waveguide structures in the microfabricated component and the locations of the cores of the individual fibers in the array. While the main component of the FSC is lithographically patterned to nanometer-scale accuracy, the array of spots from the fiber array is mechanically defined. Errors in spot position can arise from manufacturing tolerances in the array of V-grooves used to hold the fibers, which can be sub-micron for a part also made lithographically, as well as from core-cladding concentricity errors of the individual fibers, which can be substantial on the scale of the spot diameter (e.g. 1 µm concentricity error with 3.4 µm mode field diameter for a single-mode fiber in a visible wavelength). Exemplary V-groove assemblies, and their alternatives, are described in U.S. Pat. No. 7,058,275.

To reduce the loss of optical throughput in the FSC, as well as to improve uniformity among channels in the FSC, it would be advantageous to better control the spacing of the fiber modes at the interface between the fiber array and the waveguide structure. This might be done with active control of individual fiber position at assembly, but the challenges of simultaneously fixturing many small fibers for active alignment and subsequent bonding in place in a very restricted volume (with fiber spacing on the order of the fiber diameter) are difficult.

Figure 16:
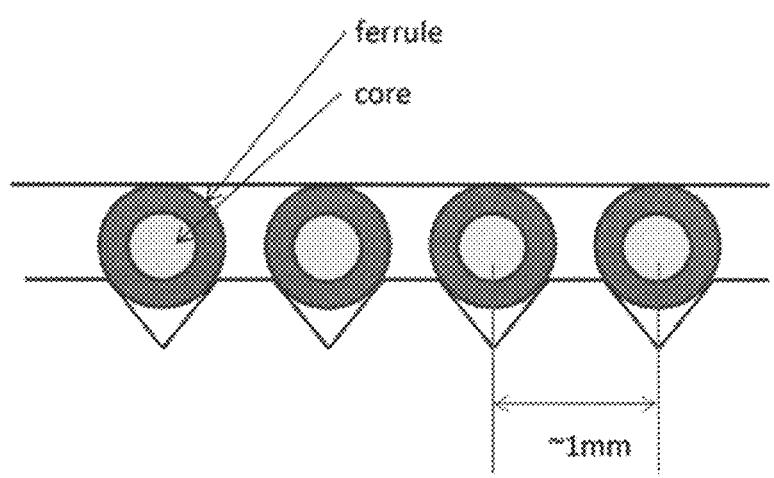
FIG. 16 shows a novel fiber spacing concentrator with active core alignment.

To improve uniformity and reduce losses in an FSC assembly, the bare fibers in the mechanical assembly (for example in a V-groove array) can be replaced with pre-aligned fiber and ferrule assemblies that can offer much tighter concentricity. See FIG. 16. Active alignment of individual fibers to ferrules is an existing process capable of providing very low loss in fiber-to-fiber links. Concentricity tolerances can be reduced from ~1 µm for bare fiber to ~125 nm between the core and a precision-polished ferrule. Suitable ferrules and core alignment technologies are available commercially, for example, from Diamond SA, Losone, Switzerland. This approach substantially reduces the overall alignment error between fiber core and waveguides in the FSC, resulting in improved uniformity and lower transmission losses.

Various aspects of the devices can be varied including:
The operating wavelength, fiber mode field diameter, and type.
Number of inputs to the FSC—this approach is readily applicable to an FSC with arbitrary channel count.
Details of the active alignment technique for individual inputs in the FSC. Commercial products are available with a pre-aligned ferrules that are readily incorporated into an integrated solution with only minor changes to V-groove geometry/spacing.

Design of the microfabricated portion of the FSC.

Removal of the microfabricated portion of the FSC, leaving the V-groove array with pre-aligned fibers. This alternative provides an accurately spaced array of spots on a large pitch for any application where it is appropriate.

Materials of the V-groove array (glass or silicon or otherwise), and methods of assembly (e.g., adhesive bonding or mechanical fastening).

Fiber spacing concentrators are available commercially, where losses are on the order of 1 dB for applications in typical telecom wavelengths in the near IR. Losses would increase for visible wavelengths using existing devices, as the sensitivity to a given degree of mechanical misalignment increases with decreasing spot size/MFD. The approaches described here improve the throughput losses and non-uniformity of existing FSCs.

According to yet another aspect, the instant specification further provides innovative approaches to the alignment and connection of optical fibers. In particular, these approaches relate to the use of an active actuator to complete the interconnection. Such approaches can be low cost and easy to use.

As is known, low power and low power density fiber modes can be effectively coupled through precision ferrules and passive mating sleeves. High power, high power density, and small mode field diameter fibers are more challenging for passive interconnection, however, owing both to risk of damage from contamination and tight tolerances.

Passive free space interconnects have been used in order to couple with low risk of damage. These interconnects are, however, typically expensive and time consuming to use. Passive physical contact interconnections are well known for telecommunication applications. The physical contact interconnects are not well suited for high power visible light applications, for which even minute contamination can lead to a runaway that causes destruction of the fiber (aka fiber fuse), or may result in less catastrophic but still substantial reductions in transmission.

High power fibers use end caps, a fused unguided section to expand the mode and increase the threshold against damage from contamination. Unfortunately, this end cap also precludes the use of efficient physical contact connectors for the same reason.

Free space interconnections for fibers with end caps are available commercially. Such devices can be based, for example, on mechanical actuation driven by manual lead screws. The aligned optic can be, for example, a pair of mirrors. While such approaches can be effective, they are expensive and require skilled labor time to align at each fiber insertion.

An alternative is the use of an active optical element to match the expanded modes between two such single mode devices. This can make use of optics to create multiple beams to guide the alignment (e.g., diffractive optical elements (DOEs)) or other servo features. A device such as the Varioptic Baltic 617 or similar can be effective in matching modes to ensure an efficient, low cost interconnect with good tolerance to contamination.

The active optical device can be based on different actuation methods (EAP, VCM, PZTs, etc.). The device can be based on scanning prisms (e.g., Risley pair), though these may be more costly. Methods based on diffraction gratings, real time or not, can also be used.

Integrated System-On-Chip

In another aspect, the instant specification provides waveguide devices that include an integrated optical source, where the optical source is either fabricated within the waveguide device itself or is attached to the device after fabrication. The previously described optical analytical systems typically comprise an optical source (or sources) (e.g., a PLC) that is physically separate from the target waveguide device. Optical energy emitted from the source is therefore coupled to the target device through free space, as described in detail above. In some circumstances, however, it may be advantageous for the optical source to be integrated into the target device package, for example using a multichip module or system in a package (SIP) approach. Such approaches are well known in the electronics industry but have not previously been applied to integrated waveguide devices such as those used in multiplexed DNA sequencing chips. By integrating a laser, or other suitable optical source, directly into the chip package, each cell becomes a self-contained optical bench capable of illuminating and viewing target molecules within an array of optically coupled nanowells.

Conventional SIP approaches can accordingly be adapted for use in the instant integrated systems, for example by modifying a waveguide device using flip-chip assembly techniques, or the like, for example to mount a laser diode chip or other compact optical source directly on the waveguide device. Flip-chip bonding techniques have been used extensively in the electronics industry, including their more recent application to optoelectronics components. See, e.g., Han et al. (1998) J. Electron. Mater. 27:985; Li et al. (2004) P. Elecr. C. 2:1925. Advantageously, flip-chip techniques can make use of solder bumps for mounting components on interconnects. Solder bumps may, upon reflowing, pull the components into position due to the surface tension of the molten solder, thus facilitating the alignment of optical components during assembly. The choice of optical source will depend on the needs of the system. Although traditional laser diodes are edge emitters and may therefore require more complex assembly arrangements, newer technologies, such as, for example, vertical cavity surface emitting laser (VCSEL) technologies, enable more direct optical coupling from the source to the waveguide device.

It will be readily apparent to one of ordinary skill in the relevant arts that other suitable modifications and adaptations to the devices and systems described herein can be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

Example 1

Binary Grating Couplers with Low Numerical Aperture

Figure 17A:
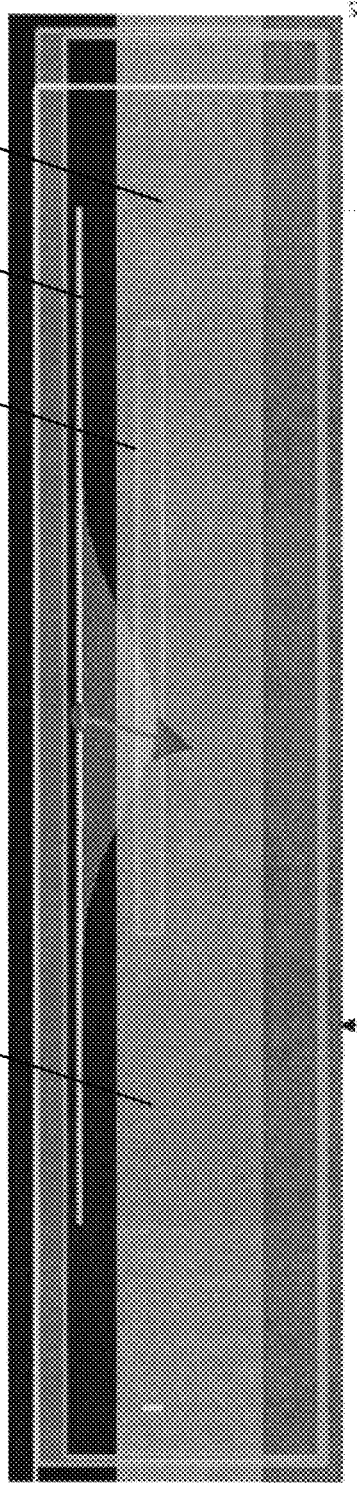
FIG. 17A illustrates a 2-dimensional low-NA grating coupler model.

This example describes the design, optimization, and modeling of various binary grating couplers having low NA. The coupling of optical energy through free space to a 2-dimensional grating coupler can be modeled using finite-difference time-domain (FDTD) numerical analysis of the Maxwell equations, for example using computer software from Lumerical (www.lumerical.com) or the like. An example of such modeling is shown in FIG. 17A, where the 2-dimensional Gaussian light source (1702) is shown in light shading above the device model. The arrow shown within the light source represents a coupling angle of 10 degrees.

Figure 17B:
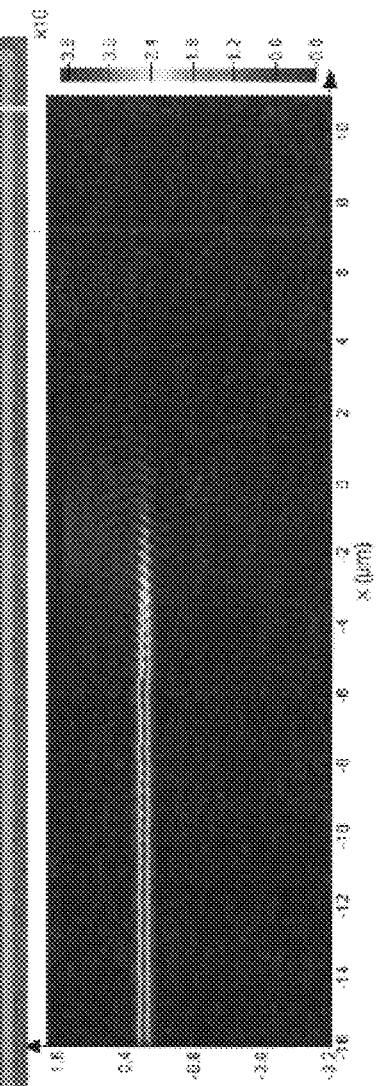
FIG. 17B illustrates the modeled optical energy coupled through the device into an integrated waveguide, where the optical energy is directed from the middle of the device towards the left side of the device.

The arrow is shown intersecting a rectangular box that represents the grating coupler structure (1704). The oxide cladding (1706) is the solid layer surrounding the coupler. The waveguide core (1708) is represented as a thin line extending to the left from the coupler. Optical energy is coupled from above the structure through the grating coupler into the waveguide core. FIG. 17B shows the results of the FDTD simulation, showing the light (in power units) coupling through the grating and propagating to the left down the waveguide core.

FIG. 18 summarizes the structural features of various binary grating coupler designs and compares the FDTD-modeled coupling efficiencies for those designs. The designs correspond to those described in FIGS. 3C-F. FIG. 19 shows the results of FDTD modeling of grating couplers having structures corresponding to that of FIG. 3A with different numerical apertures (NA). Beam sizes and grating sizes were varied in the models to be consistent with the numerical apertures.

Figure 20:
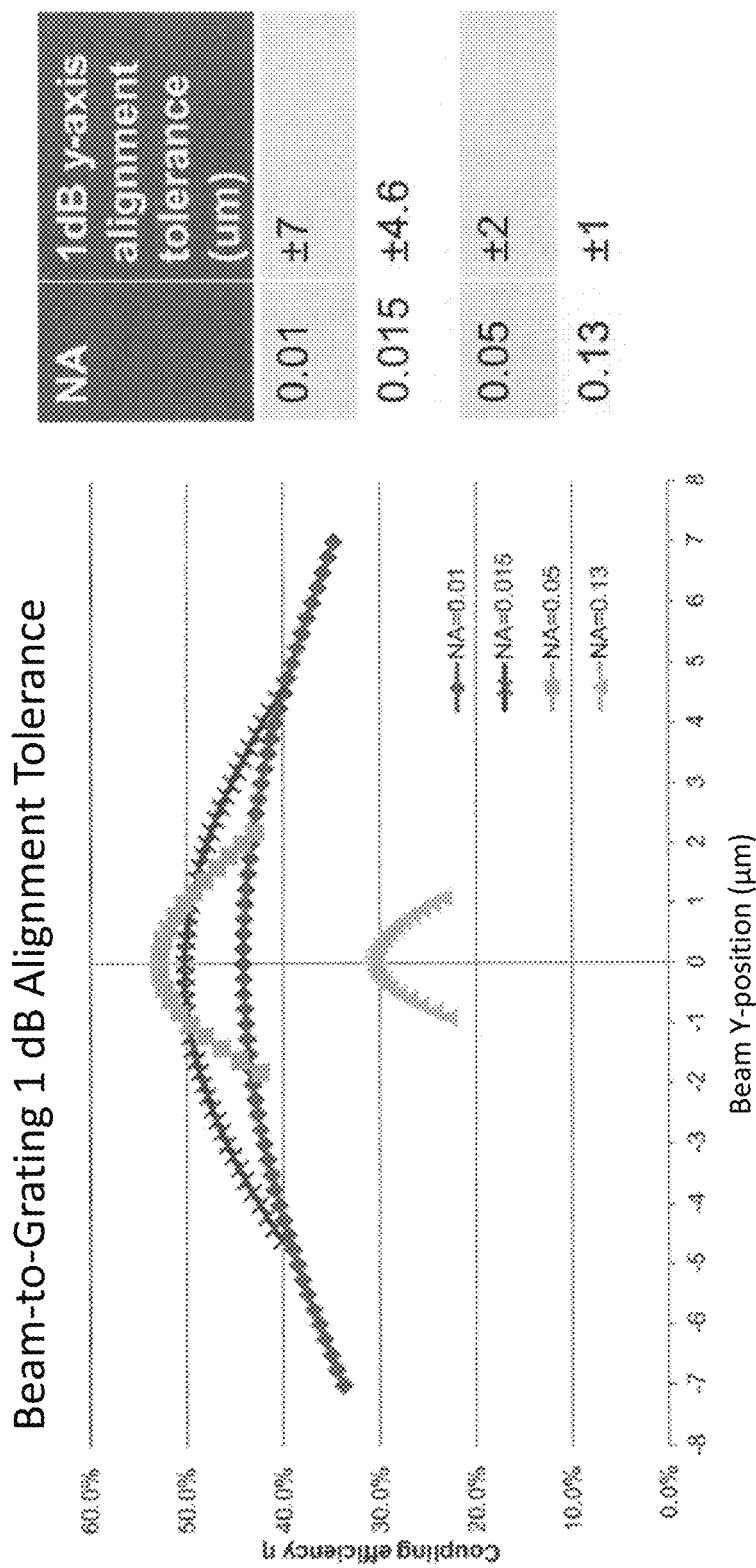
FIG. 20 illustrates fiber-to-grating alignment tolerances at various numerical aperture values.

FIG. 20 illustrates the impact of numerical aperture on the alignment tolerances for beam and grating pairs. As is clear from the models, the efficiency of coupling for the low NA couplers is much less sensitive to alignment between the optical source and the grating coupler compared to coupling for the high NA couplers.

FIG. 21 compares the modeled effects of grating period (A), buried oxide thickness (B), duty cycle (C), and etch depth (D) on efficiency of coupling. As shown in FIG. 21A, the coupling efficiency is sensitive to changes in the grating coupler period, and when the numerical aperture is decreased, the coupling efficiency becomes even more sensitive to variations in the period. Since the period is mainly determined by the accuracy of lithography and masking during chip fabrication, however, these variations can be well controlled. It should also be noted that the sensitivity of coupling efficiency on period also shows angular tolerance. Smaller numerical apertures correspond to tighter angular tolerance.

Figure 21A:
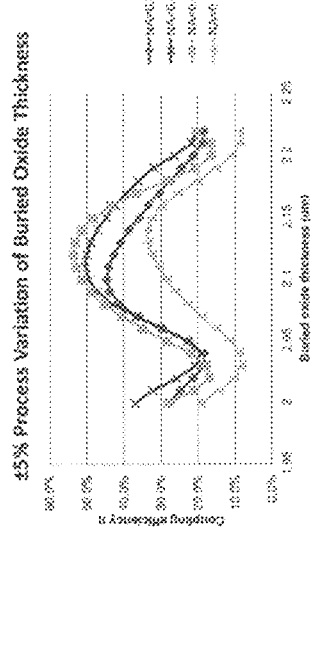
FIGS. 21A-21D illustrate the impact of grating period (A), buried oxide cladding thickness (B), duty cycle (C), and etch depth (D) on coupling efficiency at various numerical aperture values.
Figure 21C:
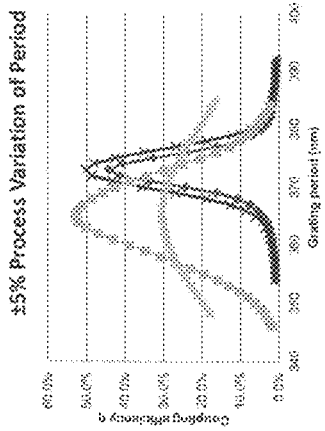
Figure 21B:
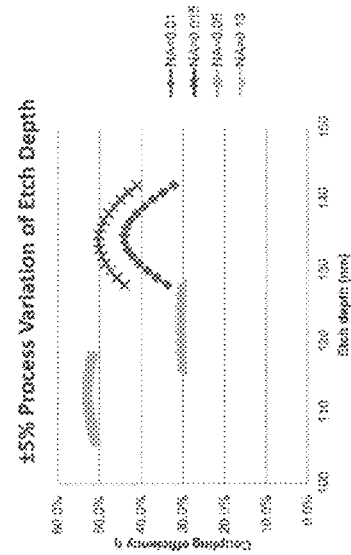

FIG. 21B demonstrates that coupling efficiency is very dependent on the thickness of the bottom oxide cladding. This dependence on bottom oxide cladding thickness is observed at all values of numerical aperture. Without intending to be bound by theory, it is believed that this dependence results from reflection of optical energy from the silicon substrate.

Figure 21D:
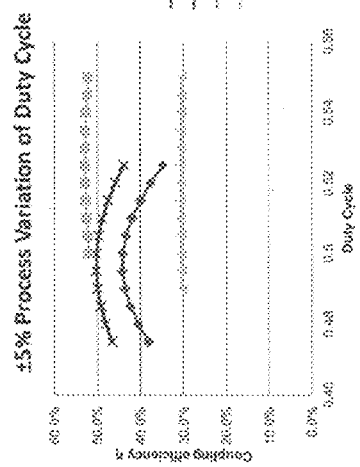

FIG. 21C shows that coupling efficiency is relatively insensitive to changes of grating coupler duty cycle for couplers with high numerical aperture, but the coupling efficiency becomes more sensitive to changes in duty cycle as the numerical aperture is decreased. Likewise, as shown in FIG. 21D, coupling efficiency is relatively insensitive to changes of grating coupler etch depth at high numerical aperture, but the sensitivity to etch depth variation increases for lower numerical apertures.

FIG. 22 summarizes simulations for couplers designed using parameters obtained from the simulations of FIG. 19. The bottom three rows show results using these parameters in simulations using an etch depth of 115 nm. The optimal bottom oxide thicknesses are as shown in the bottom row of the figure.

Example 2

Estimation of Coupling Efficiencies into Model Target Waveguide Device

This example provides estimated coupling efficiencies for a waveguide device with an $Si_3N_4$ core with dimensions roughly 0.600×0.050 μm, surrounded by $SiO_2$ cladding, and supporting a single $TM_0$ mode.

Coupling efficiency:

$$\eta_{target\ device} = \frac{Power\ in\ guided\ mode}{Total\ power\ in\ device}$$

Waveguide effective index:

$$n_e = \frac{\beta}{k} = 1.9$$

Figure 23A:
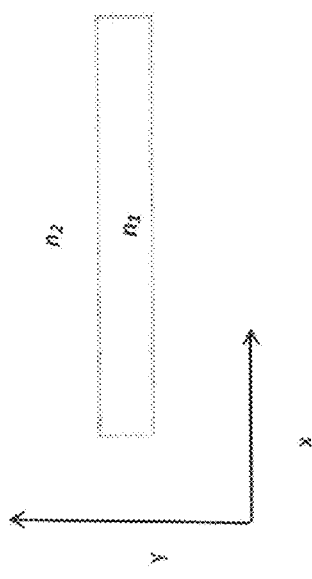
FIG. 23A shows the cross section of an exemplary waveguide of the instant target devices.
Figure 23B:
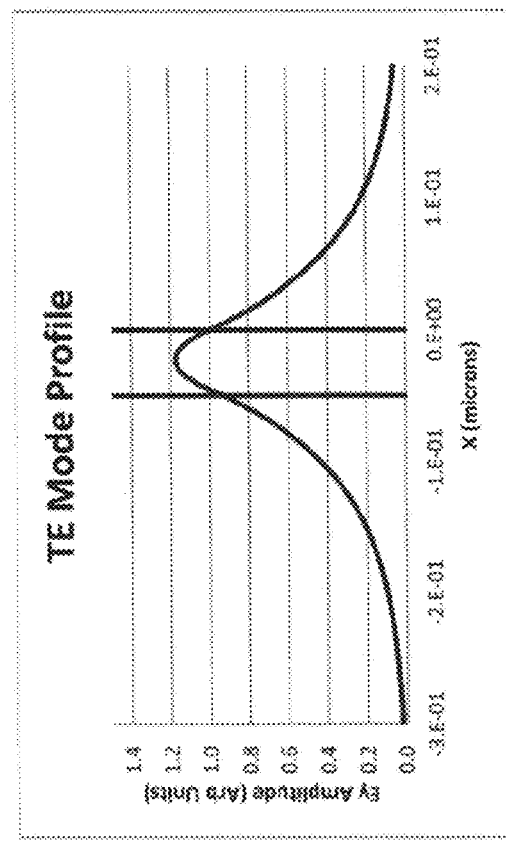
FIG. 23B shows the electric field intensity through the center of the waveguide.

$\lambda$=532 nm, k=1.18×10$^{-9}$ cm$^{-1}$
$\beta$=1.87×10$^5$ cm$^{-1}$
κ=coupling coefficient (mode overlap integral)
Maximum condition: κL=π/2
Requirement for minimum radius of curvature: 0.9 mm
Radiative loss per bend: 0.5 dB A not-to-scale representation of the exemplary waveguide cross-section is shown in FIG. 23A. Estimates of coupling efficiency are based on a calculation of the overlap integral between the desired mode profile and the excitation field. An analytics solution of the fields for this geometry is not known, but the basic mode profile of the $TE_0$ mode of this waveguide can be approximated (Schlosser and Unger, based on assumption of large aspect ratio). The electric field intensity through the center of the waveguide is plotted in FIG. 23B (Schlosser approximation).

Example 3

Theoretical Transverse Coupling into Waveguide Device with a Polished Facet

The overall coupling efficiency of a device with a polished facet is the product of reflectance loss and mode overlap, where reflection loss for free-space coupling is larger than for an incident plane wave: 9.6%. Perfect coupling would require an incident energy distribution that is exactly the inverse of the far-field distribution of light exiting the guide. A more accurate calculation of the reflectance loss, however, would require integration over these angles. The result of integrating over the high NA dimension only is 12.4%. The best-case insertion loss of the device under a straightforward approach is $\eta_{instrument}$=0.876

The efficiency could be improved by applying an AR coating. The efficiency could also be improved by including a very small air gap—on the order of the light wavelength—between the target device and the exit facet of the illumination source.

Efficiencies are determined by the mode overlap integral:

$$\eta = \frac{\left[\int\int A(x,y)B^*(x,y)dxdy\right]^2}{\int A(x,y)A^*(x,y)dx\int B(x,y)B^*(x,y)dxdy}$$

Figure 24:
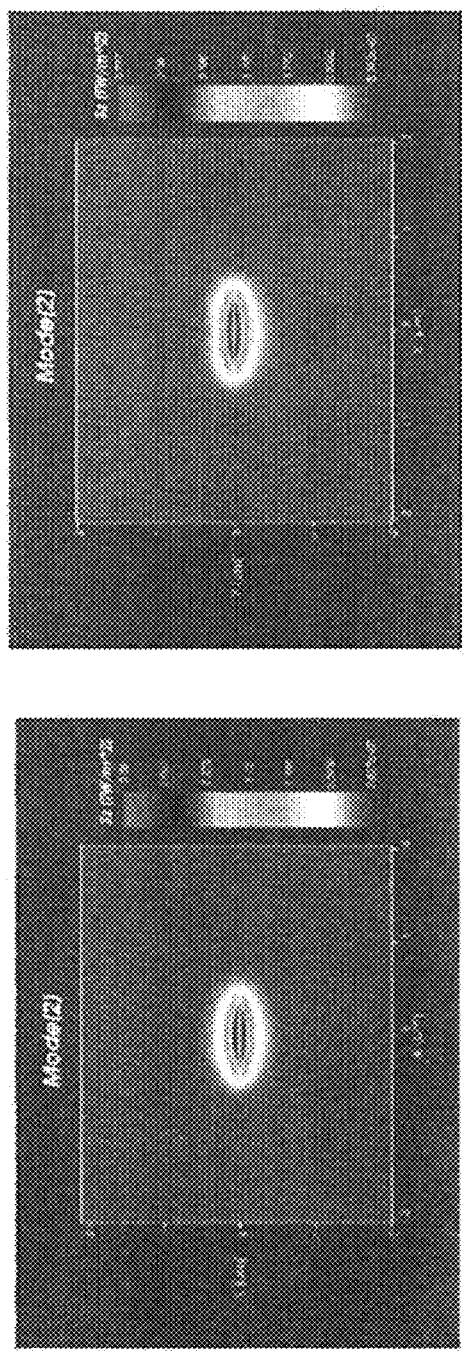
FIG. 24 shows mode profiles for prototype coupled waveguide devices.

Simulations for prototype coupled waveguide devices are shown in FIG. 24, where the left panel shows a mode profile for a simple channel guide, and the right panel shows the same channel guide with an added nanohole is added. A small perturbation to the field profile is noticeable at the center top edge, but this perturbation was ignored for coupling estimates.

In principle, an input optical beam can be created with very good match to the mode profile. As a limiting case, it can be assumed that the overlap integral is perfect for perfect alignment. In this case the sensitivity to alignment can be estimated by a calculation of the overlap integral as a function of beam displacement. Since the degree of confinement in the y direction is much stronger than in x, only y misalignment can be considered. Specifically, the spatial scale of y misalignment impact is roughly 5× larger than for x misalignment, and it is easier to mitigate with in-plane tapering of the guide input section.

Figure 25:
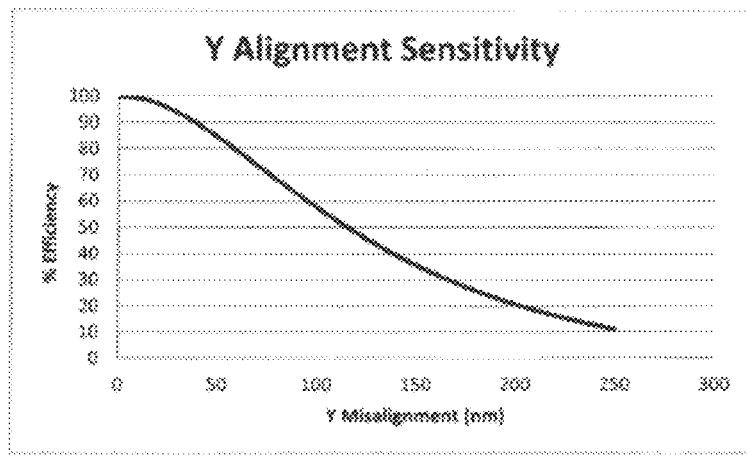
FIG. 25 illustrates the impact of y misalignment on the efficiency of coupling.

The impact of y misalignment is calculated from the mode overlap integral and illustrated in FIG. 25. At 100 nm misalignment, the power drops by roughly half. If high device efficiency is needed, or if a low drift in intensity at measurement locations on the target device is needed, active alignment may be necessary. It may also be worth considering increasing the beam size in order to loosen the mechanical requirements for achieving a certain minimal field intensity at the measurement locations on the target device, but an increased beam size will not change the ratio below, nor will it change the tolerance on a given power stability requirement. A flattop intensity profile could be considered; in such a configuration a gradual drop in intensity is avoided at the expense of a rapid falloff at the edge of a "safe" range.

Example 4

Theoretical Coupling into Waveguide Device Using a Prism Coupler

An optical waveguide confines light in the x and y dimensions; the confinement requires total internal reflection and a cladding with lower index than the core. Coupling into a target waveguide device by simple refraction is not possible. The geometry of coupling is constrained by phase-matching between the free-space optical source beam and the guided mode according to:

$$\beta_m = \frac{2\pi n_p}{\lambda} \sin\theta_m$$

Assuming a perfectly collimated input beam with diameter W, $\theta_m$ is the incident angle of the input beam inside the prism. The coupling coefficient, κ, is determined by mode overlap similar to the description in Example 2. The coupling efficiency, η, is determined by κ and the interaction length, L. Finally, weakly coupled modes are assumed.

It is theoretically possible to achieve 100% coupling efficiency in this arrangement with a perfectly controlled air gap and waveguide tolerances and with a flattop incident beam. In practice, however, coupling efficiencies of 90% have been demonstrated in the laboratory. Such efficiencies have required a non-Gaussian beam and a tapered air gap. In a straightforward approach with a uniform air gap and a Gaussian beam, efficiencies very close to the 81% theoretical limit have been demonstrated. The tolerances required for this approach in this example are as follows:
Air gap: 30 nm
Air gap variation=0
z alignment accuracy: 50 nm y alignment accuracy: 50 nm* cos $\theta_m$.

For perfect geometry complete coupling occurs at an interaction length, $$L = \frac{W}{\cos\theta_m} = \frac{\pi}{2\kappa}$$

It should be understood that misalignment in the z direction will prevent complete coupling. Furthermore, complete coupling can only occur for a flattop beam, whereas a Gaussian beam is theoretically limited to 80% efficiency, even for a perfect geometry. If the efficiency requirement is relaxed to 60%, the tolerances become much looser. Accordingly, for the instant example, $$\eta_{instrument} \cdot \eta_{device} = 0.6, \text{ with } \eta_{device} = 0.80.$$

Figure 26:
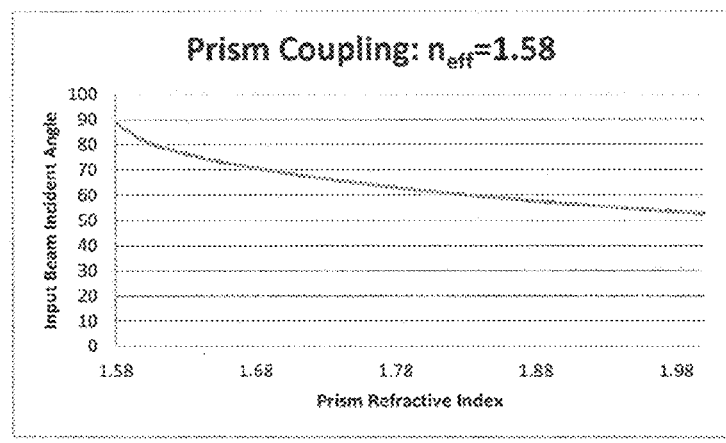
FIG. 26 illustrates the relationship between the prism refractive index and the input incident angle for a prism-coupled device.

It has been noted that the prism must have a higher refractive index than the cladding material. This requirement is very general, but maximum coupling efficiencies and instrument configurations are dependent on the prism index selected. A higher index implies a lower incident angle, which is convenient for flexibility in instrument and device packaging, and higher theoretical coupling efficiencies. For example, FIG. 26 illustrates the relationship between prism refractive index and the input incident angle for a prism-coupled device, where the effective refractive index of the device is 1.58.

Example 5

Theoretical Coupling into Waveguide Device Using a Grating Coupler

The efficiency of a grating-coupled target device is fundamentally lower than for a transverse-coupled or prism-coupled device—typically 10% for a simple grating structure. Significantly, a grating coupler lacks the chief advantage of prism coupling, which allows the incident energy to be largely confined to a single mode. In particular, zero order energy passes directly into the substrate with a grating coupler, as do many of the nonzero orders. Additionally, no total internal reflectance means strong coupling, each waveguide mode has a complete set of spatial harmonics underneath the grating, and the grating itself has higher orders. The efficiency of a grating coupler can be improved by fabricating complicated grating profiles. For example, high efficiency can be put into one order to improve the coupling. Furthermore, the z and y mechanical tolerances are very similar to the prism coupling case, with the difference being that light is more quickly coupled into substrate modes in the grating case as the beam is misaligned.

The basic phase-matching condition for a grating of period d is $$\beta = \frac{2\pi}{\lambda}\cos\theta - \frac{2\pi}{d}$$

Figure 27:
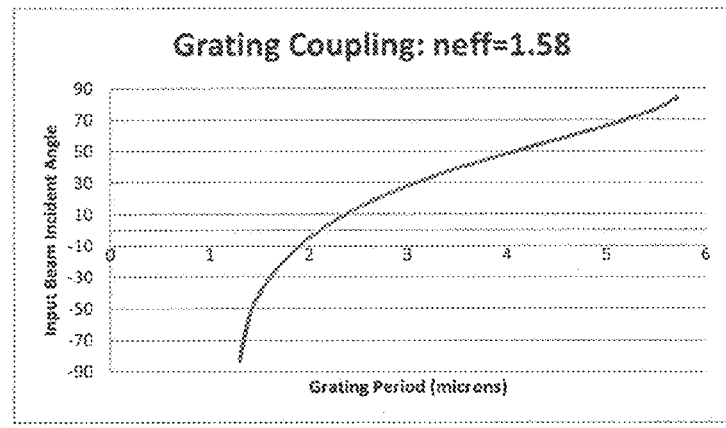
FIG. 27 illustrates the relationship between the grating period and the input incident angle for a grating-coupled device.

Phase-matching can be achieved over a wide range of angles and grating periods, so strictly speaking there is flexibility in choice of grating period. Instrument considerations argue for larger incident angles, however, whereas target device space considerations argue for smaller incident angles. FIG. 27 illustrates the relationship between the grating period and the input incident angle for a device of this example, where the effective refractive index of the device is 1.58.

TABLE 2

Summary of the best-case coupling parameters for three exemplary coupling approaches.

|  | Transverse | Prism | Grating |
|---|---|---|---|
| $\eta_{device}$ | 1.0 | 0.80 |  |
| $\eta_{optical\ source}$ | 0.68 | 0.68 | 0.68 |
| $\eta_{instrument}$ | 0.88 | 0.96 |  |
| y misalignment (3 dB) | 110 nm |  |  |
| X misalignment (3 dB) | 670 nm |  |  |

Example 6

Laser-Induced Damage Due to Heating on a Target Waveguide Device

As described above, target waveguide devices may be susceptible to thermal damage due to the high intensities of excitation energy needed to illuminate the large numbers of nanoscale reactions being analyzed in a high-density waveguide array. This example demonstrates the protective effect of including a heat spreading layer within the target device.

Figure 28:
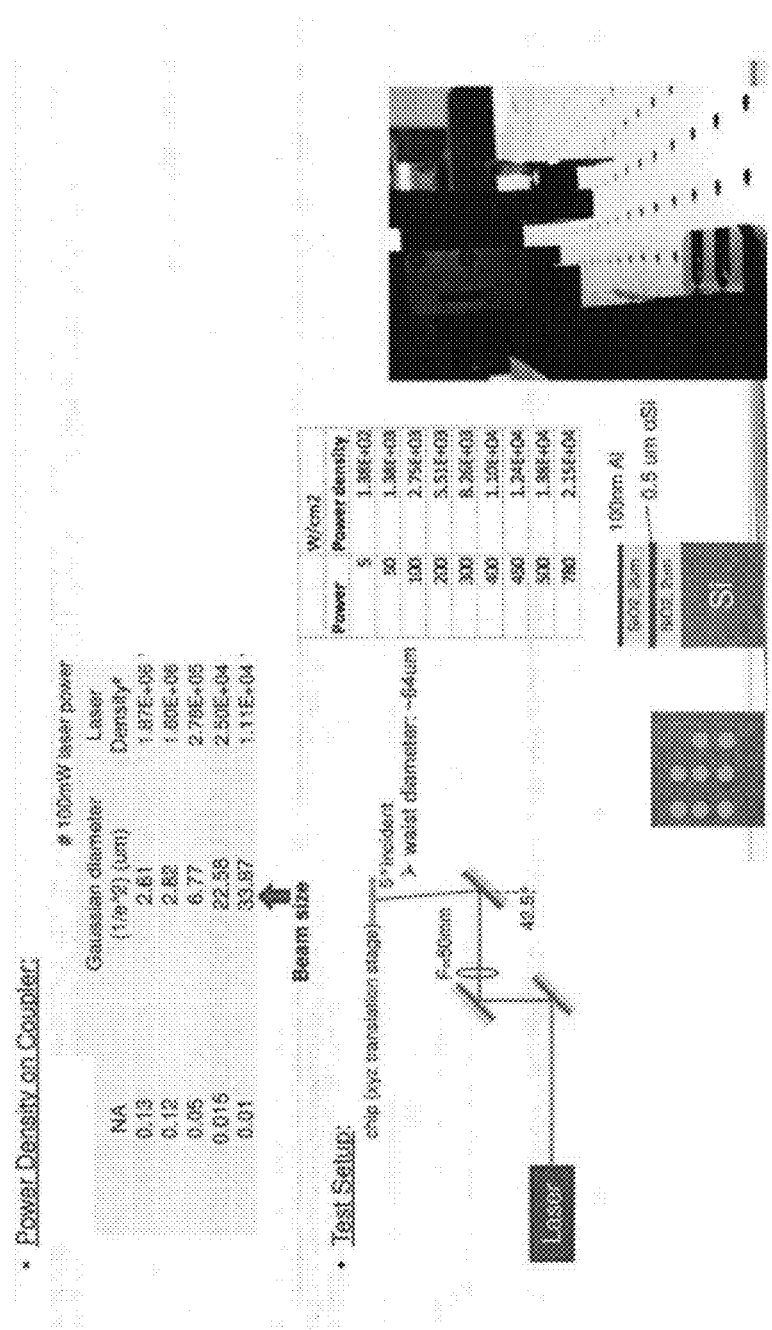
FIG. 28 shows the experimental setup used to test the effectiveness of a heat-spreading layer in mitigating laser-induced thermal damage.

FIG. 28 illustrates the test setup and shows the power densities of lasers with various numerical apertures. As is apparent in this figure, even with a low numerical aperture (e.g, 0.01) and large beam size (e.g., 33.87 µm), a 100 mW laser will still have a relatively high power density (e.g., $1.11 \times 10^4$ W/cm$^2$). The power densities used in the test setup were therefore chosen to simulate this range (e.g., 5 to 780 mW laser power; corresponding to $1.38 \times 10^2$ to $2.15 \times 10^4$ W/cm$^2$). The figure also illustrates from below and in cross-section the sample used in these tests. Specifically, the Si substrate was coated with a 2 µm layer of SiO$_2$, a 0.5 µm layer of amorphous Si, another 2 µm layer of SiO$_2$, and finally a 100 nm layer of Al. The sample also included 8 windows etched through the Si layer. For reference, the thermal conductivities of SiO$_2$, Si, and Al are 1.4, 149, and 240, respectively.

Figure 29E:
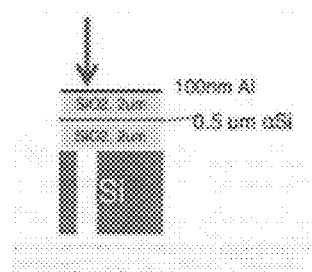
Figure 29F:
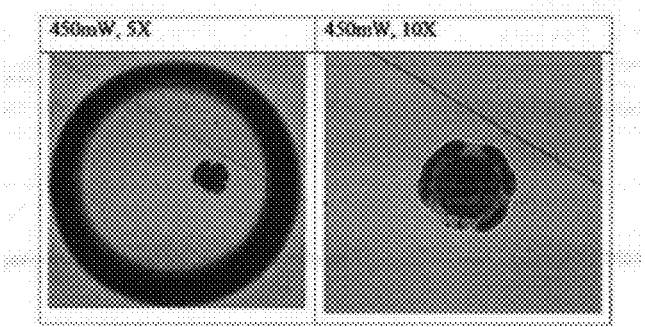
Figure 29G:
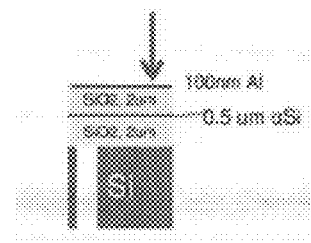

Both surfaces of the samples were visually inspected under a microscope prior to illumination with various intensities of laser energy. In the first experiment, the laser was directed through the window in the Si layer to target the SiO$_2$ layer, as indicated by the arrow the structural diagram of FIG. 29A. Illuminating the sample for 5 minutes at either 5 mW of power or 50 mW of power caused no damage, but the sample was instantly damaged upon illumination with 100 mW of laser power. The SiO$_2$ sides of the three samples are shown in the top row of FIG. 29B, and the damage to the Al side of the 100 mW sample is shown in the bottom row of the figure. In the second experiment, the laser was directed to the Al side of the sample in the region of the etched window, as indicated by the arrow in the structural diagram of FIG. 29C. In this experiment, a 5 minute illumination at 100 mW laser power caused no damage, whereas damage was observed instantly at 500 mW laser power. These samples are shown in FIG. 29D. A third experiment was similar to the second, where the laser was directed to the Al side of the sample in the region of an etched window, as indicated by the arrow in the structural diagram of FIG. 29E. Laser outputs of 200 mW, 300 mW, and 400 mW were applied to the sample with no visible damage. Illumination of the same with 450 mW of laser power, however, resulted in damage within 3 seconds. This sample is shown in FIG. 29F. A final experiment was run, where the Al side of the sample was illuminated by the laser in a region at a distance from a window through the Si substrate, as indicated by the arrow in the structural diagram of FIG. 29G. In this experiment, no damage was observed at either 500 mW or 780 mW laser power.

Example 7

Simulation of Optimal Waveguide Dimensions for Single-Mode Operation

Figure 30:
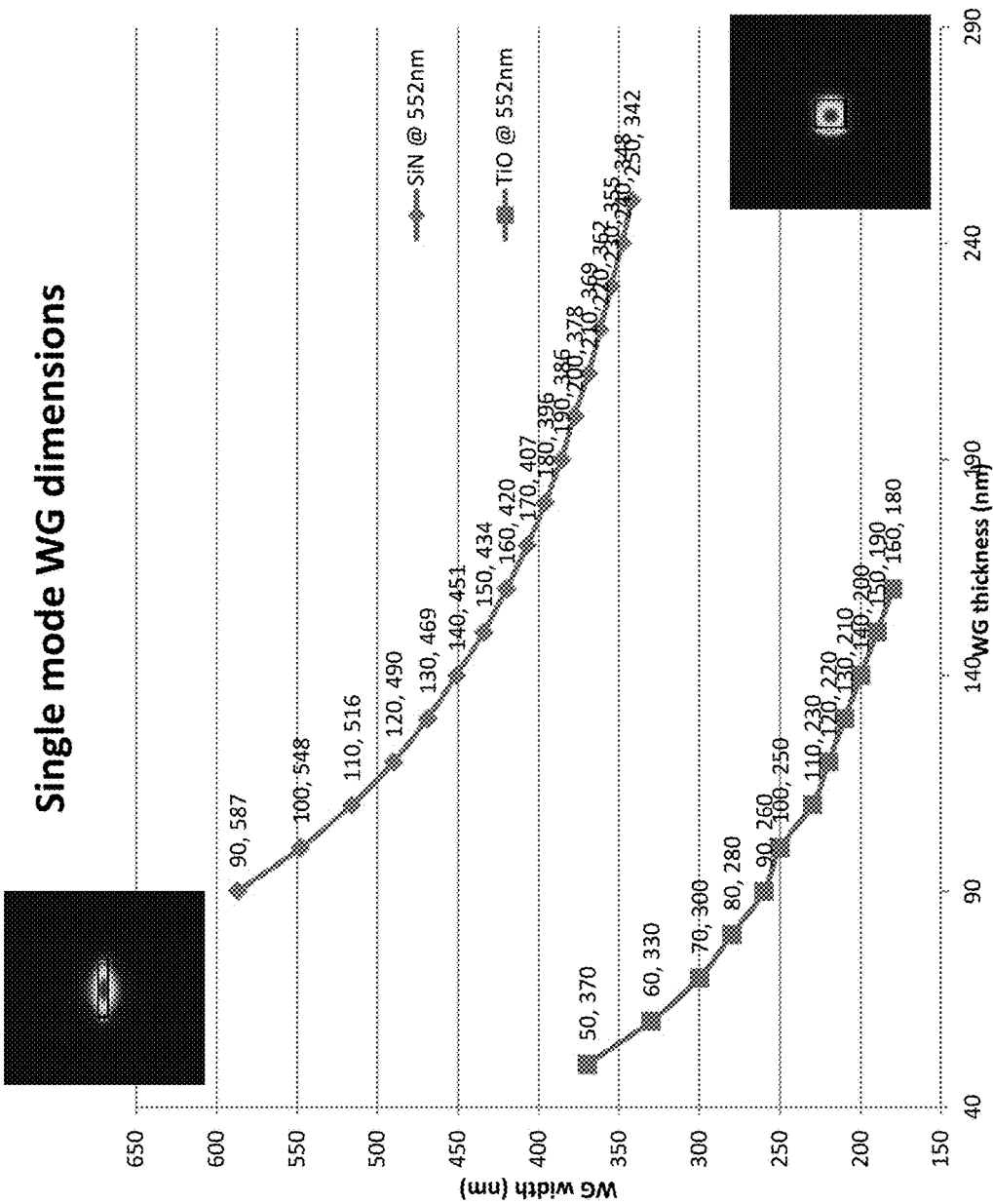
FIG. 30 shows simulations of optimized waveguide dimensions for single-mode operation in two different waveguide cores with 552 nm light.
Figure 32A:
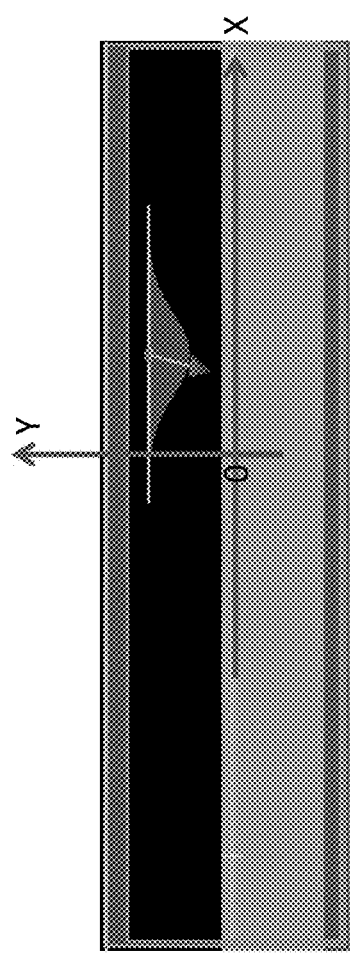
FIGS. 32A-32B illustrate a 2-dimensional grating coupler model for a target waveguide device and the modeled optical energy coupled through the device into an integrated waveguide.
Figure 32B:
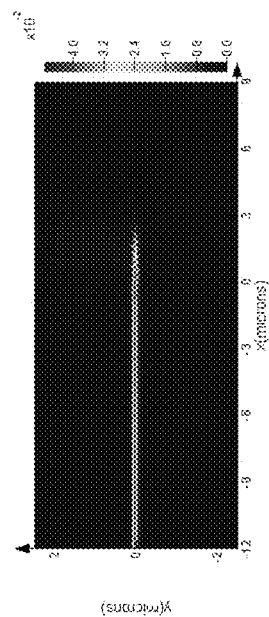

FIG. 30 shows a simulation of waveguide dimensions meeting single-mode conditions for two different core materials (SiN, top; TiO, bottom) at 552 nm. The upper left and lower right insets show FDTD simulation results for a thin and wide waveguide and a thick and narrow waveguide, respectively. The Lumerical 2D simulation setup is illustrated in FIG. 32A, and the power coupling simulation results are shown in FIG. 32B.

Example 8

Simulation of Grating Coupler Designs with Titanium Oxide Core

Figure 31:
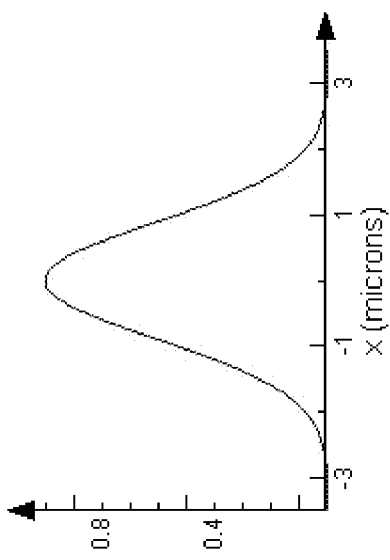
FIG. 31 shows the Gaussian profile for a simulated input beam source.

A grating coupler with a titanium oxide core and high numerical aperture (NA=0.13) but otherwise similar in design to the grating coupler described in Example 1 and modeled in FIG. 17A has been simulated by FDTD numerical analysis at two wavelengths. The input beam (at either 532 nm or 552 nm) has a beam waist of 1.75 µm (beam MFD=3.5 µm), a source size of 7 µm, and a fiber coupling angle of 10 degrees (with no angle tuning during the optimizations). The Gaussian profile for the input beam is illustrated in FIG. 31. Geometrical, mechanical, and optical specifications for a corresponding single-mode fiber (460 HP) are available, for example, from Thorlabs, Inc., Newton, N.J., USA (www.thorlabs.us). The setup for the FDTD 2D simulation using Lumerical software is shown in FIG. 32A, and the simulated power coupling results are shown in FIG. 32B.

Figure 33:
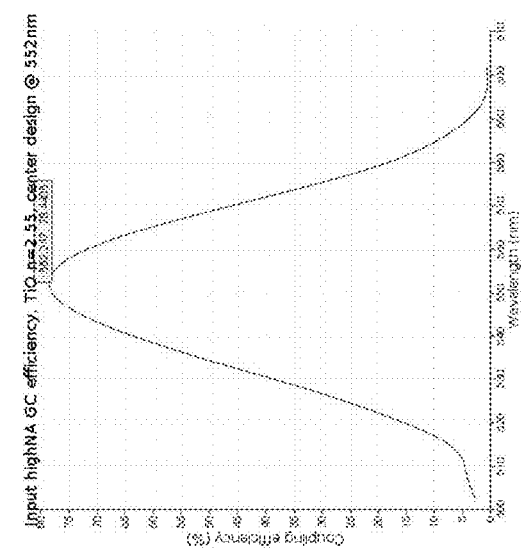
FIG. 33 illustrates effects of wavelength on modeled coupling efficiency for a high NA grating coupler design with a titanium dioxide core.

Modeling of the coupling efficiency for a high NA grating coupler center design with a titanium dioxide waveguide core at various wavelengths of input light is shown in FIG. 33. In this simulation, the coupler was modeled using the parameters listed in the second column of Table 3.

TABLE 3

High NA grating coupler center design features for simulations at 552 nm and 532 nm.

|  | Parameters for 552 nm simulations | Parameters for 532 nm simulations |
|---|---|---|
| Waveguide core | TiO$_2$ (n = 2.55) | TiO$_2$ (n = 2.55) |
| Waveguide cladding | SiO$_2$ (n = 1.46) | SiO$_2$ (n = 1.46) |
| Waveguide thickness | 100 nm | 100 nm |
| Grating coupler number of periods | 20 | 20 |
| Al reflector thickness | 100 nm | 100 nm |
| Top cladding thickness | 220 nm | 200 nm |
| Grating coupler period | 315 nm | 300 nm |
| Grating coupler teeth width | 157 nm (duty cycle = 50%) | 150 nm (duty cycle = 50%) |
| Grating coupler etch depth | 55 nm | 55 nm |
| Reflector distance | 320 nm | 290 nm |
| Optimal coupling efficiency | 78.4% (−1.06 dB) | 78% (−1.08 dB) |

TABLE 3-continued

High NA grating coupler center design features
for simulations at 552 nm and 532 nm.

|  | Parameters for 552 nm simulations | Parameters for 532 nm simulations |
| --- | --- | --- |
| Fiber x position | 1.6 µm | 1.8 µm |
| Fiber y position | 1.2 µm | 2 µm |

Figure 34B:
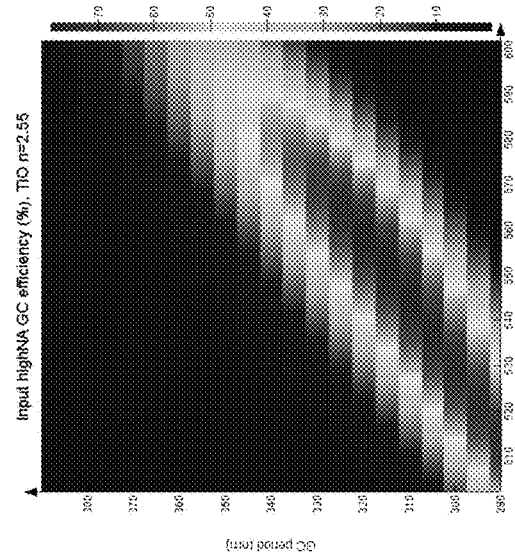
FIGS. 34A-34B illustrate effects of grating coupler period on modeled coupling efficiency for a high NA grating coupler design with a titanium dioxide core and a 552 nm input source.
Figure 34A:
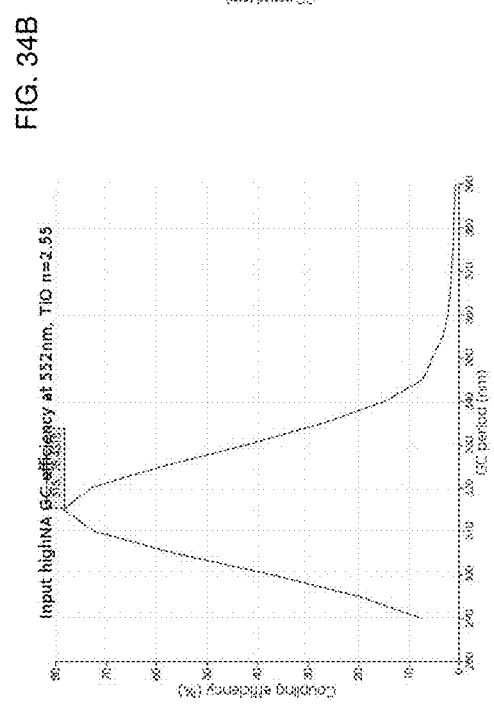

FIG. 34A illustrates the relationship between coupling efficiency and the grating coupler period at an input wavelength of 552 nm, and FIG. 34B illustrates changes in coupling efficiency as a function of grating coupler period and input wavelength for the simulated design.

Figure 35A:
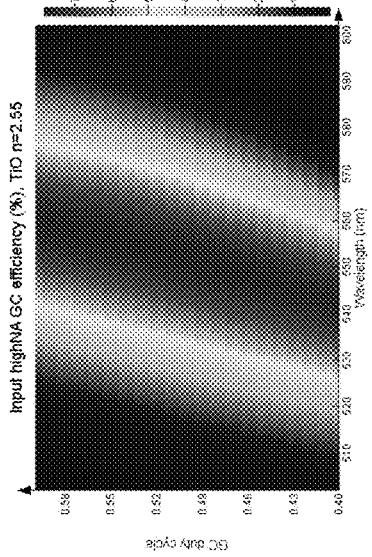
FIGS. 35A-35B illustrate effects of grating coupler duty cycle on modeled coupling efficiency for a high NA grating coupler design with a titanium dioxide core and a 552 nm input source.
Figure 35B:
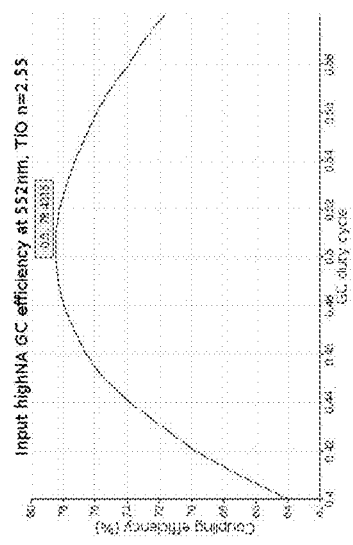

FIG. 35A illustrates the relationship between coupling efficiency and the grating coupler duty cycle at an input wavelength of 552 nm, and FIG. 35B illustrates changes in coupling efficiency as a function of grating coupler duty cycle and input wavelength for the simulated design.

Figure 36A:
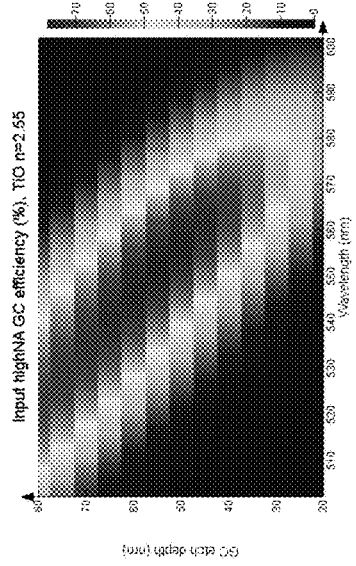
FIGS. 36A-36B illustrate effects of grating coupler etch depth on modeled coupling efficiency for a high NA grating coupler design with a titanium dioxide core and a 552 nm input source.
Figure 36B:
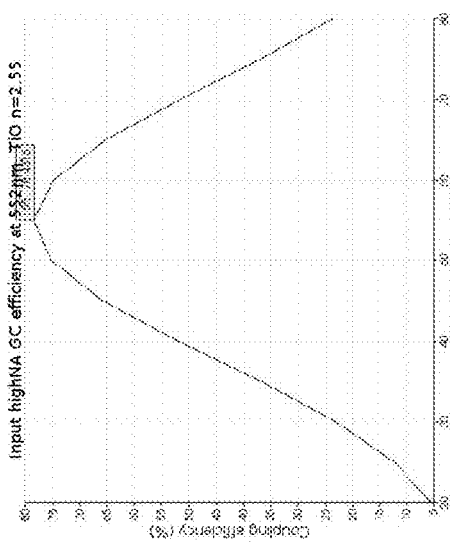

FIG. 36A illustrates the relationship between coupling efficiency and the grating coupler etch depth at an input wavelength of 552 nm, and FIG. 36B illustrates changes in coupling efficiency as a function of grating coupler etch depth and input wavelength for the simulated design.

Figure 37A:
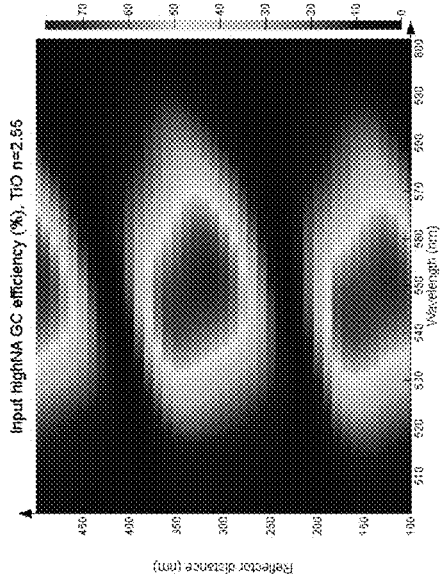
FIGS. 37A-37B illustrate effects of reflector distance on modeled coupling efficiency for a high NA grating coupler design with a titanium dioxide core and a 552 nm input source.
Figure 37B:
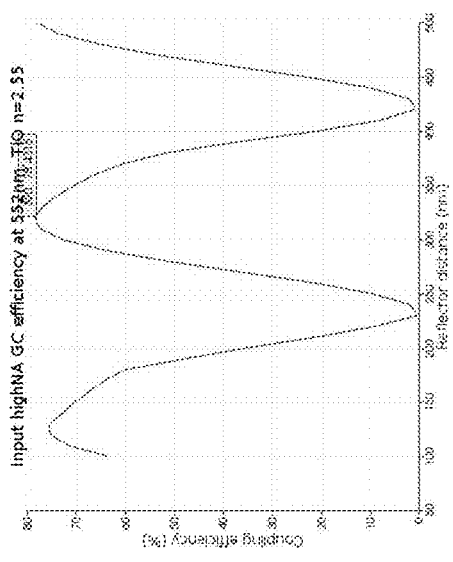

FIG. 37A illustrates the relationship between coupling efficiency and the reflector distance at an input wavelength of 552 nm, and FIG. 37B illustrates changes in coupling efficiency as a function of reflector distance and input wavelength for the simulated design.

Figure 38A:
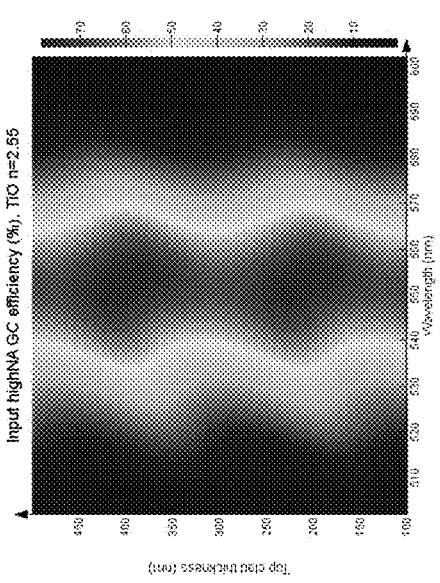
FIGS. 38A-38B illustrate effects of top clad thickness on modeled coupling efficiency for a high NA grating coupler design with a titanium dioxide core and a 552 nm input source.
Figure 38B:
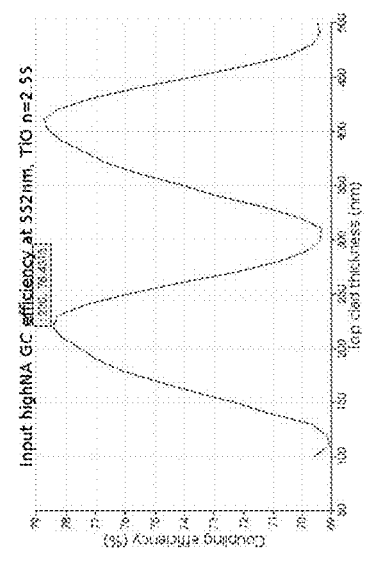

FIG. 38A illustrates the relationship between coupling efficiency and the top cladding thickness at an input wavelength of 552 nm, and FIG. 38B illustrates changes in coupling efficiency as a function of top cladding thickness and input wavelength for the simulated design.

Figure 39B:
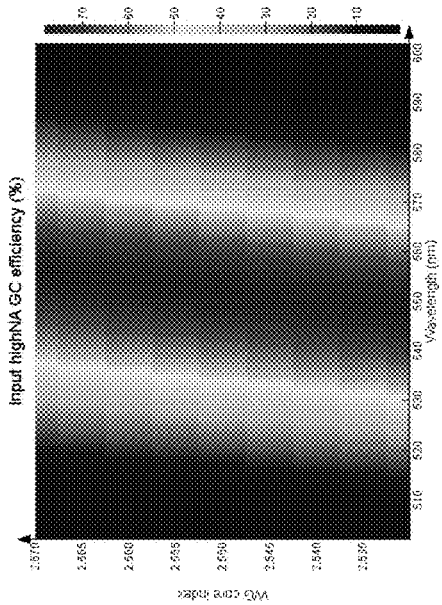
FIGS. 39A-39B illustrate effects of waveguide core index on modeled coupling efficiency for a high NA grating coupler design with a titanium dioxide core and a 552 nm input source.
Figure 39A:
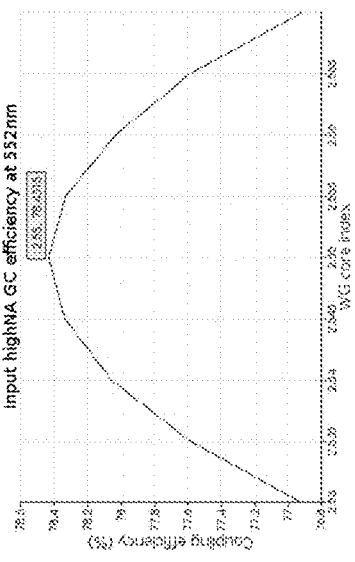

FIG. 39A illustrates the relationship between coupling efficiency and the waveguide core refractive index at an input wavelength of 552 nm, and FIG. 39B illustrates changes in coupling efficiency as a function of waveguide core refractive index and input wavelength for the simulated design.

Figure 40:
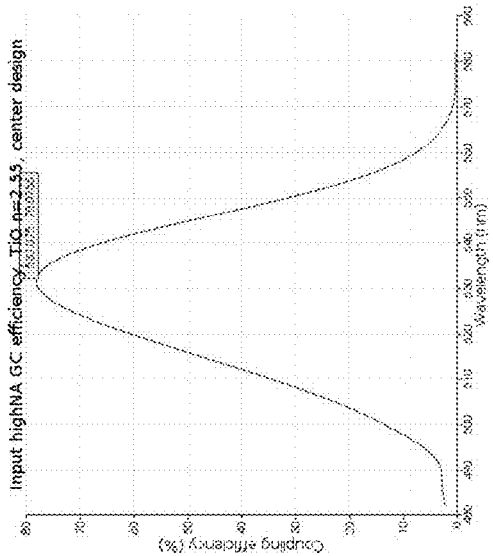
FIG. 40 plots modeled coupling efficiency for a high NA grating coupler design with a titanium dioxide core and a 532 nm input source.

Modeling of the coupling efficiency for a high NA grating coupler center design with a titanium dioxide waveguide core using 532 nm input light is shown in FIG. 40. In this simulation, the coupler was modeled using the parameters listed in the third column of Table 3.

Figure 41B:
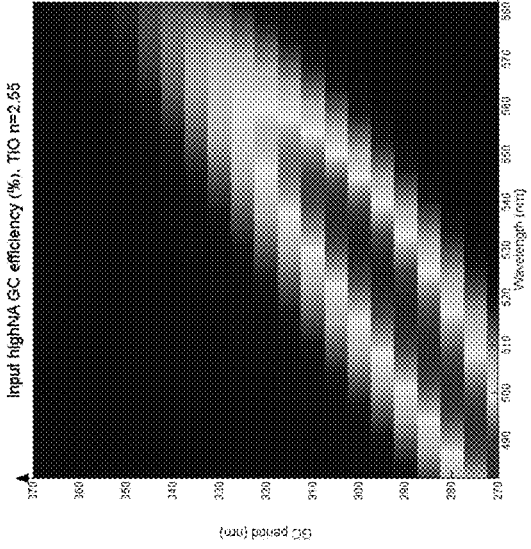
FIGS. 41A-41B illustrate effects of grating coupler period on modeled coupling efficiency for a high NA grating coupler design with a titanium dioxide core and a 532 nm input source.
Figure 41A:
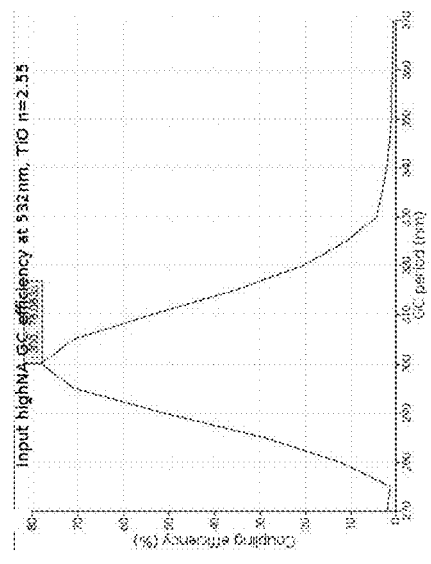

FIG. 41A illustrates the relationship between coupling efficiency and the grating coupler period at an input wavelength of 532 nm, and FIG. 41B illustrates changes in coupling efficiency as a function of grating coupler period and input wavelength for the simulated design.

Figure 42B:
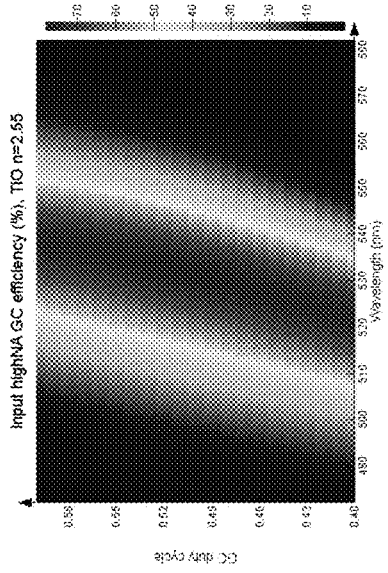
FIGS. 42A-42B illustrate effects of grating coupler duty cycle on modeled coupling efficiency for a high NA grating coupler design with a titanium dioxide core and a 532 nm input source.
Figure 42A:
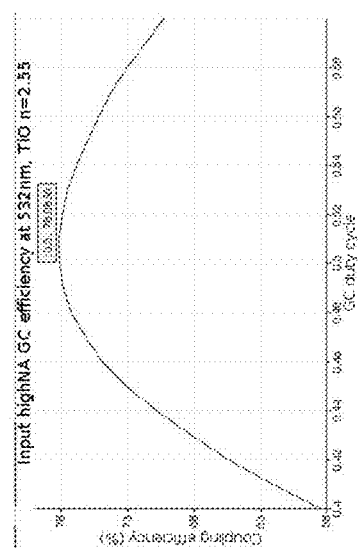

FIG. 42A illustrates the relationship between coupling efficiency and the grating coupler duty cycle at an input wavelength of 532 nm, and FIG. 42B illustrates changes in coupling efficiency as a function of grating coupler duty cycle and input wavelength for the simulated design.

Figure 43A:
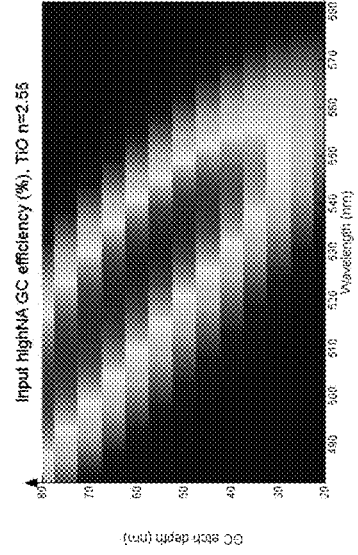
FIGS. 43A-43B illustrate effects of grating coupler etch depth on modeled coupling efficiency for a high NA grating coupler design with a titanium dioxide core and a 532 nm input source.
Figure 43B:
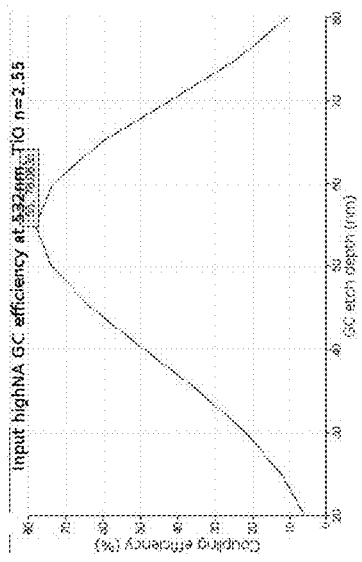

FIG. 43A illustrates the relationship between coupling efficiency and the grating coupler etch depth at an input wavelength of 532 nm, and FIG. 43B illustrates changes in coupling efficiency as a function of grating coupler etch depth and input wavelength for the simulated design.

Figure 44A:
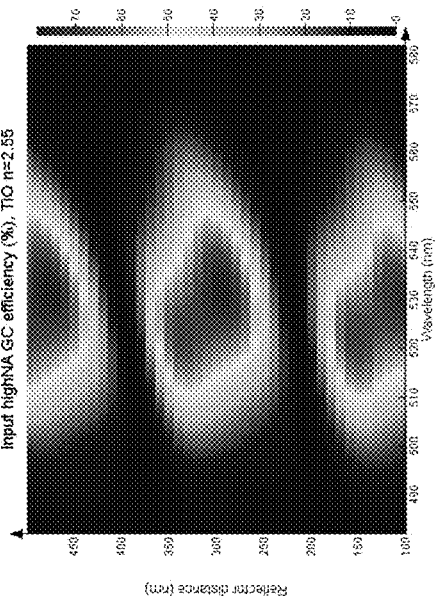
FIGS. 44A-44B illustrate effects of reflector distance on modeled coupling efficiency for a high NA grating coupler design with a titanium dioxide core and a 532 nm input source.
Figure 44B:
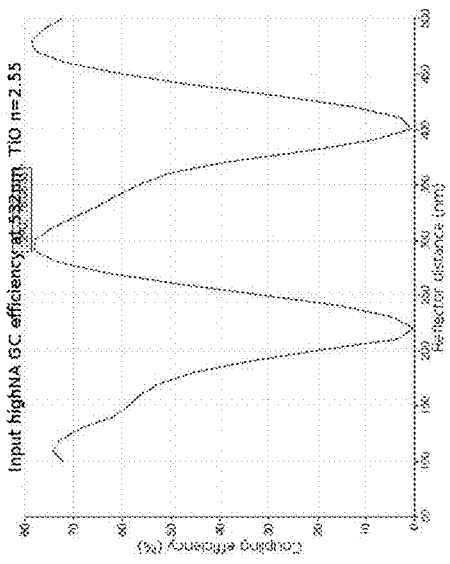

FIG. 44A illustrates the relationship between coupling efficiency and the reflector distance at an input wavelength of 532 nm, and FIG. 44B illustrates changes in coupling efficiency as a function of reflector distance and input wavelength for the simulated design.

Figure 45B:
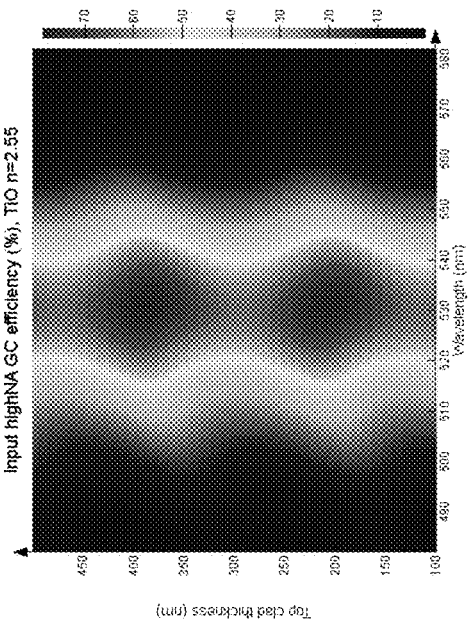
FIGS. 45A-45B illustrate effects of top clad thickness on modeled coupling efficiency for a high NA grating coupler design with a titanium dioxide core and a 532 nm input source.
Figure 45A:
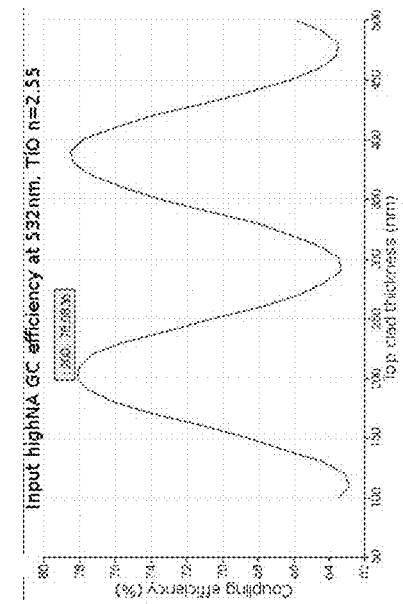

FIG. 45A illustrates the relationship between coupling efficiency and the top cladding thickness at an input wavelength of 532 nm, and FIG. 45B illustrates changes in coupling efficiency as a function of top cladding thickness and input wavelength for the simulated design.

The above simulations demonstrate that grating couplers having waveguide cores with relatively higher refractive indices (e.g., $n_{core} \geq$ about 1.9) are suitable for the efficient coupling of an input light beam into a target waveguide device at wavelengths above 532 nm. In particular, the design features of the grating couplers in such target devices can be modulated in in order to maximize coupling efficiencies of optical beams with wavelengths where fluorescent DNA sequencing reagents have maximal absorbance (e.g., about 552 nm). The simulations can also be performed using input beams and input grating couplers having lower NA values, as would be understood by those of ordinary skill in the art.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. An optical analytical system comprising:
an optical source; and
an integrated target waveguide device comprising
a low numerical aperture optical coupler of at least 100 µm² in size; and
an integrated waveguide optically coupled to the optical coupler;
wherein the optical source provides light of wavelength in the range from 400 nm to 700 nm;
wherein the optical source is optically coupled to the optical coupler of the target waveguide device through free space at a distance of at least 1 mm, and
wherein the integrated target waveguide device is removeable.

2. The optical analytical system of claim 1, wherein the optical source has a numerical aperture of no more than 0.1.

3. The optical analytical system of claim 1, wherein the optical source is configured to illuminate a spot on the target waveguide device with a surface area per spot of at least 100 µm².

4. The optical analytical system of claim 1, wherein the optical source is configured to illuminate a spot on the target waveguide device with a surface area per spot of at most 250,000 µm².

5. The optical analytical system of claim 1, wherein the optical source is configured to illuminate a spot on the target waveguide device with a surface area per spot of from 100 µm² to 250,000 µm².

6. The optical analytical system of claim 5, wherein the optical source is configured to illuminate the spot on the target waveguide device at a distance of from 1 mm to 100 mm.

7. The optical analytical system of claim 1, wherein the optical source is configured to illuminate a spot on the target waveguide device with a power per spot of at least 1 mW.

8. The optical analytical system of claim 7, wherein the optical source is configured to illuminate the spot on the target waveguide device at a distance of from 1 mm to 100 mm.

9. The optical analytical system of claim 1, wherein the optical source emits a plurality of light beams.

10. The optical analytical system of claim 9, wherein the optical source emits at least four light beams.

11. The optical analytical system of claim 9, wherein the optical source emits at least one sample excitation beam and at least one alignment beam.

12. The optical analytical system of claim 11, wherein the alignment beam has an alignment beam output power and the sample excitation beam has a sample beam output power, and wherein the alignment beam output power is lower than the sample excitation beam output power.

13. The optical analytical system of claim 12, wherein the alignment beam output power is no more than 10% of the sample excitation beam output power.

14. The optical analytical system of claim 11, further comprising an alignment detector.

15. The optical analytical system of claim 14, wherein the alignment detector is a camera.

16. The optical analytical system of claim 1, wherein the optical source comprises a planar lightwave circuit.

17. The optical analytical system of claim 1, wherein the optical source provides light of wavelength in the range from 450 nm to 650 nm.

18. The optical analytical system of claim 1, further comprising a heat sink.

19. The optical analytical system of claim 1, further comprising an optical element, wherein the optical element is positioned between the optical source and the target waveguide device.

20. The optical analytical system of claim 19, wherein the optical element modulates the focus of an optical beam transmitted from the optical source to the target waveguide device.

21. The optical analytical system of claim 19, wherein the optical element modulates the size of an optical beam transmitted from the optical source to the target waveguide device.

22. The optical analytical system of claim 1, wherein the optical coupler of the target waveguide device has a numerical aperture of no more than 0.10.

23. The optical analytical system of claim 1, wherein the optical coupler of the target waveguide device is a grating coupler.

24. The optical analytical system of claim 1, wherein the target waveguide device further comprises a reflective layer positioned below the optical coupler.

25. The optical analytical system of claim 1, wherein the target waveguide device further comprises a heat spreading layer in thermal contact with the optical coupler.

26. The optical analytical system of claim 1, wherein the target waveguide device further comprises an alignment feature.

27. The optical analytical system of claim 1, wherein the target waveguide device comprises a plurality of optical couplers and a plurality of integrated waveguides optically coupled to the plurality of optical couplers.

28. The optical analytical system of claim 1, wherein the target waveguide device further comprises a plurality of nanoscale sample wells optically coupled to the integrated waveguide.

* * * * *